United States Patent

Jonas et al.

[11] Patent Number: 5,859,008
[45] Date of Patent: Jan. 12, 1999

[54] ARYLALKYL DIAZINONES

[75] Inventors: Rochus Jonas; Michael Wolf, both of Darmstadt; Norbert Beier, Reinheim, all of Germany

[73] Assignee: Merck Patent Gesellschaft mit Beschrankter Haftung, Germany

[21] Appl. No.: 714,796

[22] Filed: Sep. 13, 1996

[30] Foreign Application Priority Data

Sep. 14, 1995 [DE] Germany .......... 195 33 975.4

[51] Int. Cl.⁶ .......... A61K 31/54; A61K 31/535; C07D 285/16; C07D 273/00
[52] U.S. Cl. .......... 514/222.5; 514/229.2; 514/252; 544/8; 544/66; 544/240
[58] Field of Search .......... 514/252, 222.5, 514/229.2; 544/240, 8, 66

[56] References Cited

U.S. PATENT DOCUMENTS

| | | | |
|---|---|---|---|
| 4,916,128 | 4/1990 | Jonas et al. | 514/213 |
| 5,026,705 | 6/1991 | Prücher et al. | 516/253 |
| 5,039,675 | 8/1991 | Mörsdorf et al. | 514/252 |
| 5,276,027 | 1/1994 | Jonas et al. | 514/222.5 |
| 5,344,925 | 9/1994 | Goulet et al. | 540/456 |
| 5,434,149 | 7/1995 | Jonas et al. | 514/222.5 |
| 5,454,149 | 10/1995 | Jonas et al. | 514/222.5 |

FOREIGN PATENT DOCUMENTS

| | | |
|---|---|---|
| 351 213 | 1/1990 | European Pat. Off. . |
| 351213 | 9/1990 | European Pat. Off. . |
| 618201 | 10/1994 | European Pat. Off. . |
| 721950 | 1/1996 | European Pat. Off. . |
| 723962 | 1/1996 | European Pat. Off. . |
| 738715 | 4/1996 | European Pat. Off. . |
| 723962 | 7/1996 | European Pat. Off. . |
| 2243667 | 3/1973 | Germany . |

OTHER PUBLICATIONS

Klemm et al., "Effect of rolipram in a murine model of acute inflammation. . . ", Eur. J. of Pharmacol., 281 (1995) pp. 69–74.

*Primary Examiner*—Mukund J. Shah
*Assistant Examiner*—Tamthom T. Ngo
*Attorney, Agent, or Firm*—Millen, White, Zelano & Branigan, P.C.

[57] ABSTRACT

Arylalkyl diazinone derivatives of the formula I

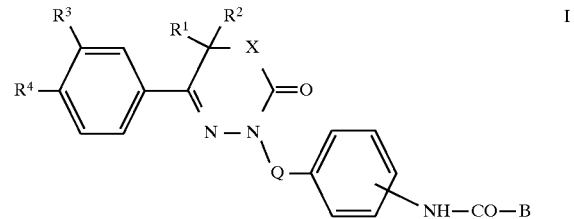

and their physiologically acceptable salts, in which $R^1$, $R^2$, $R^3$, $R^4$, B, Q and X have the meanings indicated in claim 1, exhibit phosphodiesterase IV inhibition and can be employed for the treatment of inflammatory processes and also of allergies, asthma and autoimmune disorders.

18 Claims, No Drawings

ARYLALKYL DIAZINONES

SUMMARY OF THE INVENTION

The invention relates to arylalkyl diazinone derivatives of the formula I

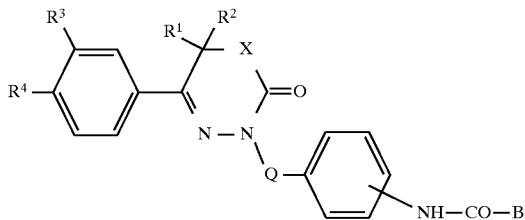

in which

B is an aromatic heterocycle having 1 to 4 N, O and/or S atoms, bonded via N or C, which can be unsubstituted or mono-, di- or trisubstituted by Hal, A and/or OA, and can also be fused to a benzene or pyridine ring,
Q is absent or is alkylene having 1–6 C atoms,
X is $CH_2$, S or O,
$R^1$ and $R^2$ in each case independently of one another are H or A,
$R^3$ and $R^4$ in each case independently of one another are —OH, $OR^5$, —S—$R^5$, —SO—$R^5$, —$SO_2$—$R^5$, Hal, methylenedioxy, —$NO_2$, —$NH_2$, —$NHR^5$ or —$NR^5R^6$,
$R^5$ and $R^6$ in each case independently of one another are A, cycloalkyl having 3–7 C atoms, methylenecycloalkyl having 4–8 C atoms or alkenyl having 2–8 C atoms,
A is alkyl having 1 to 10 C atoms, which can be substituted by 1 to 5 F and/or Cl atoms and
Hal is F, Cl, Br or I and their physiologically acceptable salts.

Thiadiazinone derivatives have been disclosed, for example, in DE 41 34 893, equivalent to U.S. Pat. No. 5,276,027.

It has been found that the compounds of the formula I and their salts have very useful pharmacological properties, combined with good tolerability, and can be used for the production of medicaments.

In particular, they all exhibit an inhibition of phosphodiesterase IV and can therefore be employed for the treatment of asthmatic disorders. The antiasthmatic action can be determined, for example, according to the method of T. Olsson, Acta allergologica 26, 438–447 (1971).

The compounds additionally exhibit an inhibitory action on the formation of TNF (tumour necrosis factor) and are therefore suitable for the treatment of allergic and inflammatory diseases, autoimmune diseases and transplant rejection reactions. They can furthermore be employed for the treatment of memory disorders.

The inhibitory action of PDEIV inhibitors on the formation of TNF (tumor necrosis factor) can be determined, e.g., according to P. Klemm et al., European Journal of Pharmacology 281, 69–74 (1995).

The compounds of the formula I can be employed as pharmaceutically active compounds in human and veterinary medicine. They can furthermore be employed as intermediates for the preparation of further pharmaceutically active compounds.

The invention accordingly relates to the compounds of the formula I and to a process for the preparation of compounds of the formula I and their salts, characterized in that a compound of the formula II

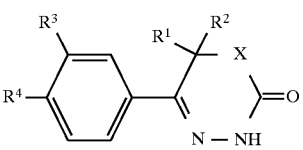

in which $R^1$, $R^2$, $R^3$, $R^4$ and X have the meanings indicated, is reacted with a compound of the formula III

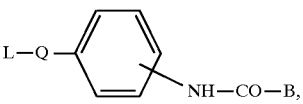

in which

B and Q have the meanings indicated, and
L is Cl, Br, OH or a reactive esterified OH group, or in that a compound of the formula IV

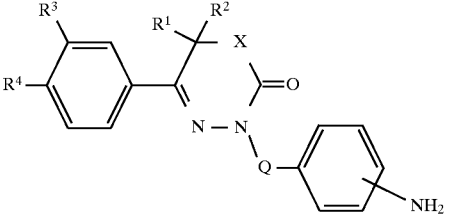

in which $R^1$, $R^2$, $R^3$, $R^4$, Q and X have the meanings indicated, is reacted with a compound of the formula V L-CO-B  V in which B has the meaning indicated, and
L is Cl, Br, OH or a reactive esterified OH group, and/or in that a basic compound of the formula I is converted into one of its salts by treating with an acid.

Above and below, the radicals $R^1$, $R^2$, $R^3$, $R^4$, B, Q and X have the meanings indicated in the formulae I, II, III, IV and V, if not expressly stated otherwise.

A is preferably alkyl, further alkyl preferably substituted by 1 to 5 fluorine and/or chlorine atoms.

In the above formulae, alkyl is preferably unbranched and has 1, 2, 3, 4, 5, 6, 7, 8, 9 or 10 C atoms, preferably 1, 2, 3, 4 or 5 C atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl or isopentyl.

Cycloalkyl preferably has 3–7 C atoms and is preferably cyclopropyl or cyclobutyl, furthermore preferably cyclopentyl or cyclohexyl, furthermore also cycloheptyl.

Methylenecycloalkyl preferably has 4–8 C atoms and is preferably methylenecyclopropyl or methylenecyclobutyl, furthermore preferably methylenecyclopentyl or methylenecyclohexyl, furthermore also methylenecycloheptyl.

Alkenyl is preferably vinyl, 1- or 2-propenyl, 1-butenyl, isobutenyl, sec-butenyl, and furthermore is preferably 1-pentenyl, isopentenyl or 1-hexenyl.

Alkylene is preferably unbranched and is preferably methylene or ethylene, furthermore preferably propylene or butylene.

Of the radicals $R^1$ and $R^2$, one is preferably H, while the other is preferably propyl or butyl, but particularly preferably ethyl or methyl. Furthermore, $R^1$ and $R^2$ together are also preferably each hydrogen.

Hal is preferably F, Cl or Br, but also I.

The radicals $R^3$ and $R^4$ can be identical or different and are in the 3- or 4-position of the phenyl ring. They are, for example, independently of one another hydroxyl, —S—$CH_3$, —SO—$CH_3$, —$SO_2CH_3$, F, Cl, Br or I or together methylenedioxy. Particularly preferably, however, they are each methoxy, ethoxy, propoxy, cyclopentoxy, or else fluoro-, difluoro-, or trifluoromethoxy, 1-fluoro-, 2-fluoro-, 1,2-difluoro-, 2,2-difluoro-, 1,2,2-trifluoro- or 2,2,2-trifluoroethoxy.

The radical B preferably contains 5–6 atoms, and is preferably monocyclic or not fused to rings other than benzene or pyridine. B is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

It applies to the entire invention that all radicals which occur several times can be identical or different, i.e. are independent of one another.

The invention accordingly relates in particular to those compounds of the formula I in which at least one of the radicals mentioned has one of the preferred meanings indicated above. Some preferred groups of compounds can be expressed by the following subformulae Ia to If, which correspond to the formula I and in which the radicals not described in greater detail have the meaning indicated in formula I, but in which in Ia
$R^1$ is H,
$R^2$ is H or A,
I
$R^3$ is OA and
X is S;
in Ib
$R^1$ is H,
$R^2$ is methyl or ethyl,
$R^3$ and $R^4$ in each case independently of one another are OA and
X is S;
in Ic
$R^1$ is H,
$R^2$ is methyl or ethyl
$R^3$ is OA
$R^4$ is mono-, di- or trifluoro-substituted alkyl having 1 to 6 C atoms and
X is S;
in Id
$R^1$ is H,
$R^2$ is methyl or ethyl,
$R^3$ and $R^4$ in each case independently of one another are $OR^5$ and
B is a pyridyl radical;
in Ie
$R^1$ and $R^2$ are H,
$R^3$ and $R^4$ in each case independently of one another are OA
B is a pyridyl radical and
X is S or $CH_2$.

The compounds of the formula I and also the starting substances for their preparation are otherwise prepared by methods known per se, such as are described in the literature (e.g. in the standard works such as Houben-Weyl, Methoden der organischen Chemie [Methods of organic chemistry], Georg-Thieme-Verlag, Stuttgart; but in particular in DE 19502699.3), under reaction conditions which are known and are suitable for the reactions mentioned. In this case, use can also be made of variants which are known per se but not mentioned here in greater detail.

In the compounds of the formulae II and IV, $R^1$, $R^2$, $R^3$ and $R^4$ have the meanings indicated, in particular the preferred meanings indicated.

In the compounds of the formulae III and IV, Q is preferably methylene or ethylene, furthermore preferably propylene or butylene.

B in the compounds of the formulae III and V has the preferred meanings indicated, while L is Cl, Br, OH or a reactive esterified OH group.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, furthermore also 2-naphthalenesulfonyloxy).

The starting substances, if desired, can also be formed in situ such that they are not isolated from the reaction mixture, but immediately reacted further to give the compounds of the formula I. On the other hand, it is possible to carry out the reaction stepwise.

The compounds of the formula I can preferably be obtained by reacting compounds of the formula II with compounds of the formula III.

The starting substances of the formulae II and III are known in some cases. If they are not known, they can be prepared by methods known per se.

Pyridazinones of the formula II are described, for example, in Eur. J. Med. Chem. - Chim. Therapeut. 9, 644–650 (1977).

Thiadiazinones of the formula II and their preparation are described, for example, in German Patent Application P 41 34 893.

6-Ethyl-1,3,4-oxadiazin-2-ones of the formula II can be obtained, for example, starting from butyroveratrone, in a bromination via α-bromobutyroveratrone, a substitution of the Br atom by an OH group with the aid of potassium formate in methanol, subsequent reaction with carbomethoxyhydrazine to give the corresponding hydrazone derivative, and cyclization with the aid of potassium carbonate in toluene.

In detail, the reaction of the compounds of the formula II with the compounds of the formula III is carried out in the presence or absence of an inert solvent at temperatures between approximately −20° and approximately 150°, preferably between 20° and 100°.

Suitable inert solvents are, for example, hydrocarbons, such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, or mixtures of the solvents mentioned.

Compounds of the formula I can furthermore be obtained by reacting compounds of the formula IV with compounds of the formula V. The starting compounds of the formulae IV and V are generally known. If they are not known, they can be prepared by methods known per se. Compounds of the formula IV are known in particular from DE 19502699 and DE 19514568.

In the compounds of the formula V, the radical —CO-L is a preactivated carboxylic acid, preferably a carbonyl halide.

The reaction of the compounds of the formula IV with compounds of the formula V is carried out under the same conditions, concerning the reaction time, temperature and solvent, as is described for the reaction of the compounds of the formula II with compounds of the formula III.

A base of the formula I can be converted into the associated acid addition salt using an acid, for example by reaction of equivalent amounts of the base and of the acid in an inert solvent such as ethanol and subsequent concentration by evaporation. Suitable acids for this reaction are in particular those which yield physiologically acceptable salts. Inorganic acids can thus be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, for example picrates, can be used for isolating and/or purifying the compounds of the formula I.

On the other hand, if desired, the free bases of the formula I can be liberated from their salts using bases (e.g. sodium or potassium hydroxide or carbonate).

Compounds of the formula I can contain one or more centers of asymmetry. In this case, they usually exist in racemic form. Racemates which are obtained can be separated into their enantiomers mechanically or chemically by methods known per se. Preferably, diastereomers are formed from the racemic mixture by reaction with an optically active resolving agent.

Of course, it is also possible to obtain optically active compounds of the formula I according to the methods described above by using starting compounds which are already optically active.

The formula I embraces all stereoisomers and their mixtures, e.g. the racemates.

The invention furthermore relates to the use of compounds of the formula I and/or their physiologically acceptable salts for the production of pharmaceutical preparations, in particular by a non-chemical route. In this context, they can be brought into a suitable dose form together with at least one solid, liquid and/or semiliquid excipient or auxiliary and, if appropriate, in combination with one or more further active compounds.

The invention also relates to medicaments of the formula I and their physiologically acceptable salts as phosphodiesterase IV inhibitors.

The invention furthermore relates to pharmaceutical preparations, comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. Tablets, pills, coated tablets, capsules, powders, granules, syrups, juices or drops are used in particular for oral administration, suppositories are used for rectal administration, solutions, preferably oily or aqueous solutions, furthermore suspensions, emulsions or implants, are used for parenteral administration and ointments, creams or powders are used for topical application. The novel compounds can also be lyophilized and the lyophilisates obtained used, for example, for the production of injection preparations. The preparations indicated can be sterilized and/or contain auxiliaries such as glidants, preservatives, stabilizers and/or wetting agents, emulsifiers, salts for influencing the osmotic pressure, buffer substances, colorants, flavorings and/or one or more further active compounds, e.g., one or more vitamins.

The compounds of the formula I and their physiologically acceptable salts can be employed in the control of illnesses in which an increase in the cAMP (cyclic adenosine monophosphate) level leads to inhibition or prevention of inflammation and muscle relaxation. The compounds according to the invention can particularly be used in the treatment of allergies, asthma, chronic bronchitis, multiple sclerosis, rheumatoid arthritis, transplant rejections, atopic dermatitis, psoriasis and other skin diseases and autoimmune disorders, e.g., acquired immune deficiency syndrome, analogously to rolipram, as disclosed in WO 92/19594.

In the following examples "customary working up" means: if necessary, water is added, the mixture is adjusted, if necessary, to a pH of between 2 and 10 depending on the constitution of the final product, and extracted with ethylacetate or dichloromethane, the organic phase is separated off, dried over sodium sulfate and evaporated, and the residue is purified by chromatography on silica gel and/or by crystallization.

Mass spectrometry (MS): EI (electron impact ionization) $M^+$
FAB (fast atom bombardment) $(M+H)^+$ Without further elaboration, it is believed that one skilled in the art can, using the preceding description, utilize the present invention to its fullest extent. The following prefered specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application DE 195 33 975.4, are hereby incorporated by reference.

EXAMPLE 1

A suspension of 4.70 g of 6-(3,4-dimethoxyphenyl)-2,3,4,5-tetrahydropyridazin-3-one ("A") in 150 ml of THF is treated with 2.24 g of potassium tert-butoxide and the mixture is stirred for 30 minutes. 7.32 g of 4-nicotinoylaminobenzyl chloride is added and the mixture is subsequently stirred at room temperature for 10 hours. The solvent is removed and the residue is worked up in the customary manner. 2-(4-nicotinoylaminobenzyl)-6-(3,4-dimethoxyphenyl)-2,3,4,5-tetrahydropyridazin-3-one is obtained.

The following is obtained analogously by reaction of "A"

with 4-isonicotinoylaminobenzyl chloride: 2-(4-isonicotinoylaminobenzyl)-6-(3,4-dimethoxyphenyl)-2,3,4,5-tetrahydropyradizin-3-one.

EXAMPLE 2

A solution of 3.4 g of 2-(4-aminobenzyl)-6-(3,4-dimethoxyphenyl)-2,3,4,5-tetrahydropyridazin-3-one, m.p. 184°, and 0.75 ml of pyridine in 100 ml of dichloromethane is treated with 1.4 g of nicotinoyl chloride and subsequently stirred for 1 hour. The solvent is removed and the mixture is worked up in the customary manner. After recrystallization, 2-(4-nicotinoylaminobenzyl)-6-(3,4-dimethoxyphenyl)-2,3,4,5-tetrahydropyridazin-3-one is obtained.

Analogously, by reaction of the "amine derivatives" below 2-(3-aminobenzyl)-6-(3,4-dimethoxyphenyl)-2,3,4,5-tetrahydropyridazin-3-one, m.p. 140°
2-(2-aminobenzyl)-6-(3,4-dimethoxyphenyl)-2,3,4,5-tetrahydropyridazin-3-one
2-(4-aminobenzyl)-6-(3,4-dimethoxyphenyl)-5-ethyl-2,3,4,5-tetrahydropyridazin-3-one;
2-(3-aminobenzyl)-6-(3,4-dimethoxyphenyl)-5-ethyl-2,3,4,5-tetrahydropyridazin-3-one, m.p. 49°
2-(2-aminobenzyl)-6-(3,4-dimethoxyphenyl)-5-ethyl-2,3,4,5-tetrahydropyridazin-3-one
2-(4-aminobenzyl)-6-(3-methoxy-4-trifluoromethoxyphenyl)-5-ethyl-2,3,4,5-tetrahydropyridazin-3-one
2-(4-aminobenzyl)-6-(3-methoxy-4-difluoromethoxyphenyl)-5-ethyl-2,3,4,5-tetrahydropyridazin-3-one
2-(4-aminobenzyl)-6-(3-methoxy-4-fluoromethoxyphenyl)-5-ethyl-2,3,4,5-tetrahydropyridazin-3-one
2-(4-aminobenzyl)-6-(3-difluoromethoxy-4-methoxyphenyl)-5-ethyl-2,3,4,5-tetrahydropyridazin-3-one
2-(4-aminobenzyl)-6-(3-trifluoromethoxy-4-methoxyphenyl)-5-ethyl-2,3,4,5-tetrahydropyridazin-3-one
2-(4-aminobenzyl)-6-(3-fluoromethoxy-4-methoxyphenyl)-5-ethyl-2,3,4,5-tetrahydropyridazin-3-one
2-(4-aminobenzyl)-6-(3-methoxy-4-ethoxyphenyl)-5-ethyl-2,3,4,5-tetrahydropyridazin-3-one
2-(4-aminobenzyl)-6-(3-ethoxy-4-methoxyphenyl)-5-ethyl-2,3,4,5-tetrahydropyridazin-3-one
2-(4-aminobenzyl)-6-(3-hydroxy-4-methoxyphenyl)-5-ethyl-2,3,4,5-tetrahydropyridazin-3-one
2-(4-aminobenzyl)-6-(4-methylsulfonylphenyl)-5-ethyl-2,3,4,5-tetrahydropyridazin-3-one
2-(4-aminobenzyl)-6-(4-methyleneoxyphenyl)-5-ethyl-2,3,4,5-tetrahydropyridazin-3-one
2-(4-aminobenzyl)-6-(3-cyclopentyloxy-4-methoxyphenyl)-5-ethyl-2,3,4,5-tetrahydropyridazin-3-one
2-(3-aminobenzyl)-6-(3-cyclopentyloxy-4-methoxyphenyl)-5-ethyl-2,3,4,5-tetrahydropyridazin-3-one, m.p. 109°
2-(4-aminophenethyl)-6-(3,4-dimethoxyphenyl)2,3,4,5-tetrahydropyridazin-3-one
2-(4-aminophenethyl)-6-(3,4-dimethoxyphenyl)-5-ethyl-2,3,4,5-tetrahydropyridazin-3-one
3-(4-aminobenzyl)-5-(3,4-dimethoxyphenyl)-3,6-dihydro-1,3,4-thiadiazin-2-one
3-(3-aminobenzyl)-5-(3,4-dimethoxyphenyl)-3,6-dihydro-1,3,4-thiadiazin-2-one
3-(2-aminobenzyl)-5-(3,4-dimethoxyphenyl)-3,6-dihydro-1,3,4-thiadiazin-2-one
3-(4-aminobenzyl)-5-(3,4-dimethoxyphenyl)-6-ethyl-3,6-dihydro-1,3,4-thiadiazin-2-one, m.p. 105°
3-(3-aminobenzyl)-5-(3,4-dimethoxyphenyl)-6-ethyl-3,6-dihydro-1,3,4-thiadiazin-2-one m.p. 112°
3-(2-aminobenzyl)-5-(3,4-dimethoxyphenyl)-6-ethyl-3,6-dihydro-1,3,4-thiadiazin-2-one
3-(4-aminobenzyl)-5-(3-methoxy-4-trifluoromethoxyphenyl)-6-ethyl-3,6-dihydro-1,3,4-thiadiazin-2-one
3-(4-aminobenzyl)-5-(3-methoxy-4-difluoromethoxyphenyl)-6-ethyl-3,6-dihydro-1,3,4-thiadiazin-2-one
3-(4-aminobenzyl)-5-(3-methoxy-4-fluoromethoxyphenyl)-6-ethyl-3,6-dihydro-1,3,4-thiadiazin-2-one
3-(4-aminobenzyl)-5-(3-difluoromethoxy-4-methoxyphenyl)-6-ethyl-3,6-dihydro-1,3,4-thiadiazin-2-one
3-(4-aminobenzyl)-5-(3-trifluoromethoxy-4-methoxyphenyl)-6-ethyl-3,6-dihydro-1,3,4-thiadiazin-2-one
3-(4-aminobenzyl)-5-(3-fluoromethoxy-4-methoxyphenyl)-6-ethyl-3,6-dihydro-1,3,4-thiadiazin-2-one
3-(4-aminobenzyl)-5-(3-methoxy-4-ethoxyphenyl)-6-ethyl-3,6-dihydro-1,3,4-thiadiazin-2-one
3-(4-aminobenzyl)-5-(3-ethoxy-4-methoxyphenyl)-6-ethyl-3,6-dihydro-1,3,4-thiadiazin-2-one
3-(4-aminobenzyl)-5-(3-hydroxy-4-methoxyphenyl)-6-ethyl-3,6-dihydro-1,3,4-thiadiazin-2-one
3-(4-aminobenzyl)-5-(4-methylsulfonylphenyl)-6-ethyl-3,6-dihydro-1,3,4-thiadiazin-2-one
3-(4-aminobenzyl)-5-(4-methyleneoxyphenyl)-6-ethyl-3,6-dihydro-1,3,4-thiadiazin-2-one
3-(4-aminobenzyl)-5-(3-cyclopentyloxy-4-methoxyphenyl)-6-ethyl-3,6-dihydro-1,3,4-thiadiazin-2-one, m.p. 132°
3-(3-aminobenzyl)-5-(3-cyclopentyloxy-4-methoxyphenyl)-6-ethyl-3,6-dihydro-1,3,4-thiadiazin-2-one
3-(4-aminophenethyl)-5-(3,4-dimethoxyphenyl)-3,6-dihydro-1,3,4-thiadiazin-2-one
3-(4-aminophenethyl)-5-(3,4-dimethoxyphenyl)-6-ethyl-3,6-dihydro-1,3,4-thiadiazin-2-one
3-(4-aminobenzyl)-5-(3,4-dimethoxyphenyl)-3,6-dihydro-1,3,4-oxadiazin-2-one
3-(3-aminobenzyl)-5-(3,4-dimethoxyphenyl)-3,6-dihydro-1,3,4-oxadiazin-2-one 3-(2-aminobenzyl)-5-(3,4-dimethoxyphenyl)-3,6-dihydro-1,3,4-oxadiazin-2-one
3-(4-aminobenzyl)-5-(3,4-dimethoxyphenyl)-6-ethyl-3,6-dihydro-1,3,4-oxadiazin-2-one
3-(3-aminobenzyl)-5-(3,4-dimethoxyphenyl)-6-ethyl-3,6-dihydro-1,3,4-oxadiazin-2-one
3-(2-aminobenzyl)-5-(3,4-dimethoxyphenyl)-6-ethyl-3,6-dihydro-1,3,4-oxadiazin-2-one
3-(4-aminobenzyl)-5-(3-methoxy-4-trifluoromethoxyphenyl)-6-ethyl-3,6-dihydro-1,3,4-oxadiazin-2-one
3-(4-aminobenzyl)-5-(3-methoxy-4-difluoromethoxyphenyl)-6-ethyl-3,6--dihydro-1,3,4-oxadiazin-2-one
3-(4-aminobenzyl)-5-(3-methoxy-4-fluoromethoxyphenyl)-6-ethyl-3,6-dihydro-1,3,4-oxadiazin-2-one
3-(4-aminobenzyl)-5-(3-difluoromethoxy-4-methoxyphenyl)-6-ethyl-3,6-dihydro-1,3,4-oxadiazin-2-one
3-(4-aminobenzyl)-5-(3-trifluoromethoxy-4-methoxyphenyl)-6-ethyl-3,6-dihydro-1,3,4-oxadiazin-2-one
3-(4-aminobenzyl)-5-(3-fluoromethoxy-4-methoxyphenyl)-6-ethyl-3,6-dihydro-1,3,4-oxadiazin-2-one
3-(4-aminobenzyl)-5-(3-methoxy-4-ethoxyphenyl)-6-ethyl-3,6-dihydro-1,3,4-oxadiazin-2-one
3-(4-aminobenzyl)-5-(3-ethoxy-4-methoxyphenyl)-6-ethyl-3,6-dihydro-1,3,4-oxadiazin-2-one
3-(4-aminobenzyl)-5-(3-hydroxy-4-methoxyphenyl)-6-ethyl-3,6-dihydro-1,3,4-oxadiazin-2-one
3-(4-aminobenzyl)-5-(4-methysulfonylphenyl)-6-ethyl-3,6-dihydro-1,3,4-oxadiazin-2-one
3-(4-aminobenzyl)-5-(4-methyleneoxyphenyl)-6-ethyl-3,6-dihydro-1,3,4-oxadiazin-2-one
3-(4-aminobenzyl)-5-(3-cyclopentyloxy-4-methoxyphenyl)-6-ethyl-3,6-dihydro-1,3,4-oxadiazin-2-one
3-(3-aminobenzyl)-5-(3-cyclopentyloxy-4-methoxyphenyl)-6-ethyl-3,6-dihydro-1,3,4-oxadiazin-2-one
3-(4-aminophenethyl)-5-(3,4-dimethoxyphenyl)-3,6-dihydro-1,3,4-oxadiazin-2-one
3-(4-aminophenethyl)-5-(3,4-dimethoxyphenyl)-6-ethyl-3,6-dihydro-1,3,4-oxadiazin-2-one with nicotinoyl chloride the compounds below are obtained 2-(3-nicotinoylaminobenzyl)-6-(3,4-dimethoxyphenyl)-2,3,4,5-tetrahydropyridazin-3-one
2-(2-nicotinoylaminobenzyl)-6-(3,4-dimethoxyphenyl)-2,3,4,5-tetrahydropyridazin-3-one
2-(4-nicotinoylaminobenzyl)-6-(3,4-dimethoxyphenyl)-5-ethyl-2,3,4,5-tetrahydropyridazin-3-one;
2-(3-nicotinoylaminobenzyl)-6-(3,4-dimethoxyphenyl)-5-ethyl-2,3,4,5-tetrahydropyridazin-3-one
2-(2-nicotinoylaminobenzyl)-6-(3,4-dimethoxyphenyl)-5-ethyl-2,3,4,5-tetrahydropyridazin-3-one
2-(4-nicotinoylaminobenzyl)-6-(3-methoxy-4-trifluoromethoxyphenyl)-5-ethyl-2,3,4,5-tetrahydropyridazin-3-one
2-(4-nicotinoylaminobenzyl)-6-(3-methoxy-4-difluoromethoxyphenyl)-5-ethyl-2,3,4,5-tetrahydropyridazin-3-one
2-(4-nicotinoylaminobenzyl)-6-(3-methoxy-4-fluoromethoxyphenyl)-5-ethyl-2,3,4,5-tetrahydropyridazin-3-one
2-(4-nicotinoylaminobenzyl)-6-(3-difluoromethoxy-4-methoxyphenyl)-5-ethyl-2,3,4,5-tetrahydropyridazin-3-one
2-(4-nicotinoylaminobenzyl)-6-(3-trifluoromethoxy-4-methoxyphenyl)-5-ethyl-2,3,4,5-tetrahydropyridazin-3-one
2-(4-nicotinoylaminobenzyl)-6-(3-fluoromethoxy-4-methoxyphenyl)-5-ethyl-2,3,4,5-tetrahydropyridazin-3-one
2-(4-nicotinoylaminobenzyl)-6-(3-methoxy-4-ethoxyphenyl)-5-ethyl-2,3,4,5-tetrahydropyridazin-3-one
2-(4-nicotinoylaminobenzyl)-6-(3-ethoxy-4-methoxyphenyl)-5-ethyl-2,3,4,5-tetrahydropyridazin-3-one
2-(4-nicotinoylaminobenzyl)-6-(3-hydroxy-4-methoxyphenyl)-5-ethyl-2,3,4,5-tetrahydropyridazin-3-one
2-(4-nicotinoylaminobenzyl)-6-(4-methylsulfonylphenyl)-5-ethyl-2,3,4,5-tetrahydropyridazin-3-one
2-(4-nicotinoylaminobenzyl)-6-(4-methyleneoxyphenyl)-5-ethyl-2,3,4,5-tetrahydropyridazin-3-one
2-(4-nicotinoylaminobenzyl)-6-(3-cyclopentyloxy-4-methoxyphenyl)-5-ethyl-2,3,4,5-tetrahydropyridazin-3-one
2-(3-nicotinoylaminobenzyl)-6-(3-cyclopentyloxy-4-methoxyphenyl)-5-ethyl-2,3,4,5-tetrahydropyridazin-3-one
2-(4-nicotinoylaminophenethyl)-6-(3,4-dimethoxyphenyl)-2,3,4,5-tetrahydropyridazin-3-one
2-(4-nicotinoylaminophenethyl)-6-(3,4-dimethoxyphenyl)-5-ethyl-2,3,4,5-tetrahydropyridazin-3-one
3-(4-nicotinoylaminobenzyl)-5-(3,4-dimethoxyphenyl)-3,6-dihydro-1,3,4-thiadiazin-2-one
3-(3-nicotinoylaminobenzyl)-5-(3,4-dimethoxyphenyl)-3,6-dihydro-1,3,4-thiadiazin-2-one
3-(2-nicotinoylaminobenzyl)-5-(3,4-dimethoxyphenyl)-3,6-dihydro-1,3,4-thiadiazin-2-one
3-(4-nicotinoylaminobenzyl)-5-(3,4-dimethoxyphenyl)-6-ethyl-3,6-dihydro-1,3,4-thiadiazin-2-one
3-(3-nicotinoylaminobenzyl)-5-(3,4-dimethoxyphenyl)-6-ethyl-3,6-dihydro-1,3,4-thiadiazin-2-one
3-(2-nicotinoylaminobenzyl)-5-(3,4-dimethoxyphenyl)-6-ethyl-3,6-dihydro-1,3,4-thiadiazin-2-one
3-(4-nicotinoylaminobenzyl)-5-(3-methoxy-4-trifluoromethoxyphenyl)-6-ethyl-3,6-dihydro-1,3,4-thiadiazin-2-one
3-(4-nicotinoylaminobenzyl)-5-(3-methoxy-4-difluoromethoxyphenyl)-6-ethyl-3,6-dihydro-1,3,4-thiadiazin-2-one
3-(4-nicotinoylaminobenzyl)-5-(3-methoxy-4-fluoromethoxyphenyl)-6-ethyl-3,6-dihydro-1,3,4-thiadiazin-2-one
3-(4-nicotinoylaminobenzyl)-5-(3-difluoromethoxy-4-methoxyphenyl)-6-ethyl-3,6-dihydro-1,3,4-thiadiazin-2-one
3-(4-nicotinoylaminobenzyl)-5-(3-trifluoromethoxy-4-methoxyphenyl)-6-ethyl-3,6-dihydro-1,3,4-thiadiazin-2-one
3-(4-nicotinoylaminobenzyl)-5-(3-fluoromethoxy-4-methoxyphenyl)-6-ethyl-3,6-dihydro-1,3,4-thiadiazin-2-one
3-(4-nicotinoylaminobenzyl)-5-(3-methoxy-4-ethoxyphenyl)-6-ethyl-3,6-dihydro-1,3,4-thiadiazin-2-one
3-(4-nicotinoylaminobenzyl)-5-(3-ethoxy-4-methoxyphenyl)-6-ethyl-3,6-dihydro-1,3,4-thiadiazin-2-one
3-(4-nicotinoylaminobenzyl)-5-(3-hydroxy-4-methoxyphenyl)-6-ethyl-3,6-dihydro-1,3,4-thiadiazin-2-one 3-(4-nicotinoylaminobenzyl)-5-(4-methysulfonylphenyl)-6-ethyl-3,6-dihydro-1,3,4-thiadiazin-2-one
3-(4-nicotinoylaminobenzyl)-5-(4-methyleneoxyphenyl)-6-ethyl-3,6-dihydro-1,3,4-thiadiazin-2-one
3-(4-nicotinoylaminobenzyl)-5-(3-cyclopentyloxy-4-methoxyphenyl)-6-ethyl-3,6-dihydro-1,3,4-thiadiazin-2-one
3-(3-nicotinoylaminobenzyl)-5-(3-cyclopentyloxy-4-methoxyphenyl)-6-ethyl-3,6-dihydro-1,3,4-thiadiazin-2-one
3-(4-nicotinoylaminophenethyl)-5-(3,4-dimethoxyphenyl)-3,6-dihydro-1,3,4-thiadiazin-2-one
3-(4-nicotinoylaminophenethyl)-5-(3,4-dimethoxyphenyl)-6-ethyl-3,6-dihydro-1,3,4-thiadiazin-2-one
3-(4-nicotinoylaminobenzyl)-5-(3,4-dimethoxyphenyl)-3,6-dihydro-1,3,4-oxadiazin-2-one
3-(3-nicotinoylaminobenzyl)-5-(3,4-dimethoxyphenyl)-3,6-dihydro-1,3,4-oxadiazin-2-one
3-(2-nicotinoylaminobenzyl)-5-(3,4-dimethoxyphenyl)-3,6-dihydro-1,3,4-oxadiazin-2-one
3-(4-nicotinoylaminobenzyl)-5-(3,4-dimethoxyphenyl)-6-ethyl-3,6-dihydro-1,3,4-oxadiazin-2-one
3-(3-nicotinoylaminobenzyl)-5-(3,4-dimethoxyphenyl)-6-ethyl-3,6-dihydro-1,3,4-oxadiazin-2-one
3-(2-nicotinoylaminobenzyl)-5-(3,4-dimethoxyphenyl)-6-ethyl-3,6-dihydro-1,3,4-oxadiazin-2-one
3-(4-nicotinoylaminobenzyl)-5-(3-methoxy-4-trifluoromethoxyphenyl)-6-ethyl-3,6-dihydro-1,3,4-oxadiazin-2-one
3-(4-nicotinoylaminobenzyl)-5-(3-methoxy-4-difluoromethoxyphenyl)-6-ethyl-3,6-dihydro-1,3,4-oxadiazin-2-one
3-(4-nicotinoylaminobenzyl)-5-(3-methoxy-4-fluoromethoxyphenyl)-6-ethyl-3,6-dihydro-1,3,4-oxadiazin-2-one
3-(4-nicotinoylaminobenzyl)-5-(3-difluoromethoxy-4-methoxyphenyl)-6-ethyl-3,6-dihydro-1,3,4-oxadiazin-2-one
3-(4-nicotinoylaminobenzyl)-5-(3-trifluoromethoxy-4-methoxyphenyl)-6-ethyl-3,6-dihydro-1,3,4-oxadiazin-2-one
3-(4-nicotinoylaminobenzyl)-5-(3-fluoromethoxy-4-methoxyphenyl)-6-ethyl-3,6-dihydro-1,3,4-oxadiazin-2-one
3-(4-nicotinoylaminobenzyl)-5-(3-methoxy-4-ethoxyphenyl)-6-ethyl-3,6-dihydro-1,3,4-oxadiazin-2-one
3-(4-nicotinoylaminobenzyl)-5-(3-ethoxy-4-methoxyphenyl)-6-ethyl-3,6-dihydro-1,3,4-oxadiazin-2-one
3-(4-nicotinoylaminobenzyl)-5-(3-hydroxy-4-methoxyphenyl)-6-ethyl-3,6-dihydro-1,3,4-oxadiazin-2-one
3-(4-nicotinoylaminobenzyl)-5-(4-methylsulfonylphenyl)-6-ethyl-3,6-dihydro-1,3,4-oxadiazin-2-one
3-(4-nicotinoylaminobenzyl)-5-(4-methyleneoxyphenyl)-6-ethyl-3,6-dihydro-1,3,4-oxadiazin-2-one
3-(4-nicotinoylaminobenzyl)-5-(3-cyclopentyloxy-4-methoxyphenyl)-6-ethyl-3,6-dihydro-1,3,4-oxadiazin-2-one
3-(3-nicotinoylaminobenzyl)-5-(3-cyclopentyloxy-4-methoxyphenyl)-6-ethyl-3,6-dihydro-1,3,4-oxadiazin-2-one
3-(4-nicotinoylaminophenethyl)-5-(3,4-dimethoxyphenyl)-3,6-dihydro-1,3,4-oxadiazin-2-one
3-(4-nicotinoylaminophenethyl)-5-(3,4-dimethoxyphenyl)-6-ethyl-3,6-dihydro-1,3,4-oxadiazin-2-one.

Analogously, by reaction of the abovementioned "amine derivatives" with isonicotinoyl chloride, the compounds below are obtained 2-(4-isonicotinoylaminobenzyl)-6-(3,4-dimethoxyphenyl)-2,3,4,5-tetrahydropyridazin-3-one
2-(3-isonicotinoylaminobenzyl)-6-(3,4-dimethoxyphenyl)-2,3,4,5-tetrahydropyridazin-3-one
2-(2-isonicotinoylaminobenzyl)-6-(3,4-dimethoxyphenyl)-2,3,4,5-tetrahydropyridazin-3-one
2-(4-isonicotinoylaminobenzyl)-6-(3,4-dimethoxyphenyl)-5-ethyl-2,3,4,5-tetrahydropyridazin-3-one;
2-(3-isonicotinoylaminobenzyl)-6-(3,4-dimethoxyphenyl)-5-ethyl-2,3,4,5-tetrahydropyridazin-3-one
2-(2-isonicotinoylaminobenzyl)-6-(3,4-dimethoxyphenyl)-5-ethyl-2,3,4,5-tetrahydropyridazin-3-one
2-(4-isonicotinoylaminobenzyl)-6-(3-methoxy-4-trifluoromethoxyphenyl)-5-ethyl-2,3,4,5-tetrahydropyridazin-3-one
2-(4-isonicotinoylaminobenzyl)-6-(3-methoxy-4-difluoromethoxyphenyl)-5-ethyl-2,3,4,5-tetrahydropyridazin-3-one
2-(4-isonicotinoylaminobenzyl)-6-(3-methoxy-4-fluoromethoxyphenyl)-5-ethyl-2,3,4,5-tetrahydropyridazin-3-one
2-(4-isonicotinoylaminobenzyl)-6-(3-difluoromethoxy-4-methoxyphenyl)-5-ethyl-2,3,4,5-tetrahydropyridazin-3-one
2-(4-isonicotinoylaminobenzyl)-6-(3-trifluoromethoxy-4-methoxyphenyl)-5-ethyl-2,3,4,5-tetrahydropyridazin-3-one
2-(4-isonicotinoylaminobenzyl)-6-(3-fluoromethoxy-4-methoxyphenyl)-5-ethyl-2,3,4,5-tetrahydropyridazin-3-one
2-(4-isonicotinoylaminobenzyl)-6-(3-methoxy-4-ethoxyphenyl)-5-ethyl-2,3,4,5-tetrahydropyridazin-3-one
2-(4-isonicotinoylaminobenzyl)-6-(3-ethoxy-4-methoxyphenyl)-5-ethyl-2,3,4,5-tetrahydropyridazin-3-one
2-(4-isonicotinoylaminobenzyl)-6-(3-hydroxy-4-methoxyphenyl)-5-ethyl-2,3,4,5-tetrahydropyridazin-3-one
2-(4-isonicotinoylaminobenzyl)-6-(4-methylsulfonylphenyl)-5-ethyl-2,3,4,5-tetrahydropyridazin-3-one
2-(4-isonicotinoylaminobenzyl)-6-(4-methyleneoxyphenyl)-5-ethyl-2,3,4,5-tetrahydropyridazin-3-one
2-(4-isonicotinoylaminobenzyl)-6-(3-cyclopentyloxy-4-methoxyphenyl)-5-ethyl-2,3,4,5-tetrahydropyridazin-3-one
2-(3-isonicotinoylaminobenzyl)-6-(3-cyclopentyloxy-4-methoxyphenyl)-5-ethyl-2,3,4,5-tetrahydropyridazin-3-one
2-(4-isonicotinoylaminophenethyl)-6-(3,4-dimethoxyphenyl)-2,3,4,5-tetrahydropyridazin-3-one
2-(4-isonicotinoylaminophenethyl)-6-(3,4-dimethoxyphenyl)-5-ethyl-2,3,4,5-tetrahydropyridazin-3-one
3-(4-isonicotinoylaminobenzyl)-5-(3,4-dimethoxyphenyl)-3,6-dihydro-1,3,4-thiadiazin-2-one
3-(3-isonicotinoylaminobenzyl)-5-(3,4-dimethoxyphenyl)-3,6-dihydro-1,3,4-thiadiazin-2-one
3-(2-isonicotinoylaminobenzyl)-5-(3,4-dimethoxyphenyl)-3,6-dihydro-1,3,4-thiadiazin-2-one
3-(4-isonicotinoylaminobenzyl)-5-(3,4-dimethoxyphenyl)-6-ethyl-3,6-dihydro-1,3,4-thiadiazin-2-one 3-(3-isonicotinoylaminobenzyl)-5-(3,4-dimethoxyphenyl)-6-ethyl-3,6-dihydro-1,3,4-thiadiazin-2-one
3-(2-isonicotinoylaminobenzyl)-5-(3,4-dimethoxyphenyl)-6-ethyl-3,6-dihydro-1,3,4-thiadiazin-2-one
3-(4-isonicotinoylaminobenzyl)-5-(3-methoxy-4-trifluoromethoxyphenyl)-6-ethyl-3,6-dihydro-1,3,4-thiadiazin-2-one
3-(4-isonicotinoylaminobenzyl)-5-(3-methoxy-4-difluoromethoxyphenyl)-6-ethyl-3,6-dihydro-1,3,4-thiadiazin-2-one
3-(4-isonicotinoylaminobenzyl)-5-(3-methoxy-4-fluoromethoxyphenyl)-6-ethyl-3,6-dihydro-1,3,4-thiadiazin-2-one
3-(4-isonicotinoylaminobenzyl)-5-(3-difluoromethoxy-4-methoxyphenyl)-6-ethyl-3,6-dihydro-1,3,4-thiadiazin-2-one
3-(4-isonicotinoylaminobenzyl)-5-(3-trifluoromethoxy-4-methoxyphenyl)-6-ethyl-3,6-dihydro-1,3,4-thiadiazin-2-one
3-(4-isonicotinoylaminobenzyl)-5-(3-fluoromethoxy-4-methoxyphenyl)-6-ethyl-3,6-dihydro-1,3,4-thiadiazin-2-one
3-(4-isonicotinoylaminobenzyl)-5-(3-methoxy-4-ethoxyphenyl)-6-ethyl-3,6-dihydro-1,3,4-thiadiazin-2-one
3-(4-isonicotinoylaminobenzyl)-5-(3-ethoxy-4-methoxyphenyl)-6-ethyl-3,6-dihydro-1,3,4-thiadiazin-2-one
3-(4-isonicotinoylaminobenzyl)-5-(3-hydroxy-4-methoxyphenyl)-6-ethyl-3,6-dihydro-1,3,4-thiadiazin-2-one
3-(4-isonicotinoylaminobenzyl)-5-(4-methylsulfonylphenyl)-6-ethyl-3,6-dihydro-1,3,4-thiadiazin-2-one
3-(4-isonicotinoylaminobenzyl)-5-(4-methyleneoxyphenyl)-6-ethyl-3,6-dihydro-1,3,4-thiadiazin-2-one
3-(4-isonicotinoylaminobenzyl)-5-(3-cylcopentyloxy-4-methoxyphenyl)-6-ethyl-3,6-dihydro-1,3,4-thiadiazin-2-one
3-(3-isonicotinoylaminobenzyl)-5-(3-cyclopentyloxy-4-methoxyphenyl)-6-ethyl-3,6-dihydro-1,3,4-thiadiazin-2-one
3-(4-isonicotinoylaminophenethyl)-5-(3,4-dimethoxyphenyl)-3,6-dihydro-1,3,4-thiadiazin-2-one
3-(4-isonicotinoylaminophenethyl)-5-(3,4-dimethoxyphenyl)-6-ethyl-3,6-dihydro-1,3,4-thiadiazin-2-one
3-(4-isonicotinoylaminobenzyl)-5-(3,4-dimethoxyphenyl)-3,6-dihydro-1,3,4-oxadiazin-2-one
3-(3-isonicotinoylaminobenzyl)-5-(3,4-dimethoxyphenyl)-3,6-dihydro-1,3,4-oxadiazin-2-one
3-(2-isonicotinoylaminobenzyl)-5-(3,4-dimethoxyphenyl)-3,6-dihydro-1,3,4-oxadiazin-2-one
3-(4-isonicotinoylaminobenzyl)-5-(3,4-dimethoxyphenyl)-6-ethyl-3,6-dihydro-1,3,4-oxadiazin-2-one
3-(3-isonicotinoylaminobenzyl)-5-(3,4-dimethoxyphenyl)-6-ethyl-3,6-dihydro-1,3,4-oxadiazin-2-one
3-(2-isonicotinoylaminobenzyl)-5-(3,4-dimethoxyphenyl)-6-ethyl-3,6-dihydro-1,3,4-oxadiazin-2-one
3-(4-isonicotinoylaminobenzyl)-5-(3-methoxy-4-trifluoromethoxyphenyl)-6-ethyl-3,6-dihydro-1,3,4-oxadiazin-2-one
3-(4-isonicotinoylaminobenzyl)-5-(3-methoxy-4-difluoromethoxyphenyl)-6-ethyl-3,6-dihydro-1,3,4-oxadiazin-2-one
3-(4-isonicotinoylaminobenzyl)-5-(3-methoxy-4-fluoromethoxyphenyl)-6-ethyl-3,6-dihydro-1,3,4-oxadiazin-2-one
3-(4-isonicotinoylaminobenzyl)-5-(3-difluoromethoxy-4-methoxyphenyl)-6-ethyl-3,6-dihydro-1,3,4-oxadiazin-2-one
3-(4-isonicotinoylaminobenzyl)-5-(3-trifluoromethoxy-4-methoxyphenyl)-6-ethyl-3,6-dihydro-1,3,4-oxadiazin-2-one
3-(4-isonicotinoylaminobenzyl)-5-(3-fluoromethoxy-4-methoxyphenyl)-6-ethyl-3,6-dihydro-1,3,4-oxadiazin-2-one
3-(4-isonicotinoylaminobenzyl)-5-(3-methoxy-4-ethoxyphenyl)-6-ethyl-3,6-dihydro-1,3,4-oxadiazin-2-one
3-(4-isonicotinoylaminobenzyl)-5-(3-ethoxy-4-methoxyphenyl)-6-ethyl-3,6-dihydro-1,3,4-oxadiazin-2-one
3-(4-isonicotinoylaminobenzyl)-5-(3-hydroxy-4-methoxyphenyl)-6-ethyl-3,6-dihydro-1,3,4-oxadiazin-2-one
3-(4-isonicotinoylaminobenzyl)-5-(4-methylsulfonylphenyl)-6-ethyl-3,6-dihydro-1,3,4-oxadiazin-2-one
3-(4-isonicotinoylaminobenzyl)-5-(4-methyleneoxyphenyl)-6-ethyl-3,6-dihydro-1,3,4-oxadiazin-2-one
3-(4-isonicotinoylaminobenzyl)-5-(3-cyclopentyloxy-4-methoxyphenyl)-6-ethyl-3,6-dihydro-1,3,4-oxadiazin-2-one
3-(3-isonicotinoylaminobenzyl)-5-(3-cyclopentyloxy-4-methoxyphenyl)-6-ethyl-3,6-dihydro-1,3,4-oxadiazin-2-one
3-(4-isonicotinoylaminophenethyl)-5-(3,4-dimethoxyphenyl)-3,6-dihydro-1,3,4-oxadiazin-2-one
3-(4-isonicotinoylaminophenethyl)-5-(3,4-dimethoxyphenyl)-6-ethyl-3,6-dihydro-1,3,4-oxadiazin-2-one.

Analogously, by reaction of the abovementioned "amine derivatives" with picolinoyl chloride the compounds below are obtained 2-(4-picolinoylaminobenzyl)-6-(3,4-dimethoxyphenyl)-2,3,4,5-tetrahydropyridazin-3-one
2-(3-picolinoylaminobenzyl)-6-(3,4-dimethoxyphenyl)-2,3,4,5-tetrahydropyridazin-3-one
2-(2-picolinoylaminobenzyl)-6-(3,4-dimethoxyphenyl)-2,3,4,5-tetrahydropyridazin-3-one
2-(4-picolinoylaminobenzyl)-6-(3,4-dimethoxyphenyl)-5-ethyl-2,3,4,5-tetrahydropyridazin-3-one;
2-(3-picolinoylaminobenzyl)-6-(3,4-dimethoxyphenyl)-5-ethyl-2,3,4,5-tetrahydropyridazin-3-one
2-(2-picolinoylaminobenzyl)-6-(3,4-dimethoxyphenyl)-5-ethyl-2,3,4,5-tetrahydropyridazin-3-one
2-(4-picolinoylaminobenzyl)-6-(3-methoxy-4-trifluoromethoxyphenyl)-5-ethyl-2,3,4,5-tetrahydropyridazin-3-one
2-(4-picolinoylaminobenzyl)-6-(3-methoxy-4-difluoromethoxyphenyl)-5-ethyl-2,3,4,5-tetrahydropyridazin-3-one
2-(4-picolinoylaminobenzyl)-6-(3-methoxy-4-fluoromethoxyphenyl)-5-ethyl-2,3,4,5-tetrahydropyridazin-3-one
2-(4-picolinoylaminobenzyl)-6-(3-difluoromethoxy-4-methoxyphenyl)-5-ethyl-2,3,4,5-tetrahydropyridazin-3-one
2-(4-picolinoylaminobenzyl)-6-(3-trifluoromethoxy-4-methoxyphenyl)-5-ethyl-2,3,4,5-tetrahydropyridazin-3-one
2-(4-picolinoylaminobenzyl)-6-(3-fluoromethoxy-4-methoxyphenyl)-5-ethyl-2,3,4,5-tetrahydropyridazin-3-one 2-(4-picolinoylaminobenzyl)-6-(3-methoxy-4-ethoxyphenyl)-5-ethyl-2,3,4,5-tetrahydropyridazin-3-one 2-(4-picolinoylaminobenzyl)-6-(3-ethoxy-4-methoxyphenyl)-5-ethyl-2,3,4,5-tetrahydropyridazin-3-one 2-(4-picolinoylaminobenzyl)-6-(3-hydroxy-4-methoxyphenyl)-5-ethyl-2,3,4,5-tetrahydropyridazin-3-one 2-(4-picolinoylaminobenzyl)-6-(4-methylsulfonylphenyl)-5-ethyl-2,3,4,5-tetrahydropyridazin-3-one 2-(4-picolinoylaminobenzyl)-6-(4-methyleneoxyphenyl)-5-ethyl-2,3,4,5-tetrahydropyridazin-3-one 2-(4-picolinoylaminobenzyl)-6-(3-cyclopentyloxy-4-methoxyphenyl)-5-ethyl-2,3,4,5-tetrahydropyridazin-3-one 2-(3-picolinoylaminobenzyl)-6-(3-cyclopentyloxy-4-methoxyphenyl)-5-ethyl-2,3,4,5-tetrahydropyridazin-3-one 2-(4-picolinoylaminophenethyl)-6-(3,4-dimethoxyphenyl)-2,3,4,5-tetrahydropyridazin-3-one 2-(4-picolinoylaminophenethyl)-6-(3,4-dimethoxyphenyl)-5-ethyl-2,3,4,5-tetrahydropyridazin-3-one 3-(4-picolinoylaminobenzyl)-5-(3,4-dimethoxyphenyl)-3,6-dihydro-1,3,4-thiadiazin-2-one 3-(3-picolinoylaminobenzyl)-5-(3,4-dimethoxyphenyl)-3,6-dihydro-1,3,4-thiadiazin-2-one 3-(2-picolinoylaminobenzyl)-5-(3,4-dimethoxyphenyl)-3,6-dihydro-1,3,4-thiadiazin-2-one 3-(4-picolinoylaminobenzyl)-5-(3,4-dimethoxyphenyl)-6-ethyl-3,6-dihydro-1,3,4-thiadiazin-2-one 3-(3-picolinoylaminobenzyl)-5-(3,4-dimethoxyphenyl)-6-ethyl-3,6-dihydro-1,3,4-thiadiazin-2-one 3-(2-picolinoylaminobenzyl)-5-(3,4-dimethoxyphenyl)-6-ethyl-3,6-dihydro-1,3,4-thiadiazin-2-one 3-(4-picolinoylaminobenzyl)-5-(3-methoxy-4-trifluoromethoxyphenyl)-6-ethyl-3,6-dihydro-1,3,4-thiadiazin-2-one 3-(4-picolinoylaminobenzyl)-5-(3-methoxy-4-difluoromethoxyphenyl)-6-ethyl-3,6-dihydro-1,3,4-thiadiazin-2-one 3-(4-picolinoylaminobenzyl)-5-(3-methoxy-4-fluoromethoxyphenyl)-6-ethyl-3,6-dihydro-1,3,4-thiadiazin-2-one 3-(4-picolinoylaminobenzyl)-5-(3-difluoromethoxy-4-methoxyphenyl)-6-ethyl-3,6-dihydro-1,3,4-thiadiazin-2-one 3-(4-picolinoylaminobenzyl)-5-(3-trifluoromethoxy-4-methoxyphenyl)-6-ethyl-3,6-dihydro-1,3,4-thiadiazin-2-one 3-(4-picolinoylaminobenzyl)-5-(3-fluoromethoxy-4-methoxyphenyl)-6-ethyl-3,6-dihydro-1,3,4-thiadiazin-2-one 3-(4-picolinoylaminobenzyl)-5-(3-methoxy-4-ethoxyphenyl)-6-ethyl-3,6-dihydro-1,3,4-thiadiazin-2-one 3-(4-picolinoylaminobenzyl)-5-(3-ethoxy-4-methoxyphenyl)-6-ethyl-3,6-dihydro-1,3,4-thiadiazin-2-one 3-(4-picolinoylaminobenzyl)-5-(3-hydroxy-4-methoxyphenyl)-6-ethyl-3,6-dihydro-1,3,4-thiadiazin-2-one 3-(4-picolinoylaminobenzyl)-5-(4-methylsulfonylphenyl)-6-ethyl-3,6-dihydro-1,3,4-thiadiazin-2-one 3-(4-picolinoylaminobenzyl)-5-(4-methyleneoxyphenyl)-6-ethyl-3,6-dihydro-1,3,4-thiadiazin-2-one 3-(4-picolinoylaminobenzyl)-5-(3-cyclopentyloxy-4-methoxyphenyl)-6-ethyl-3,6-dihydro-1,3,4-thiadiazin-2-one 3-(3-picolinoylaminobenzyl)-5-(3-cyclopentyloxy-4-methoxyphenyl)-6-ethyl-3,6-dihydro-1,3,4-thiadiazin-2-one 3-(4-picolinoylaminophenethyl)-5-(3,4-dimethoxyphenyl)-3,6-dihydro-1,3,4-thiadiazin-2-one 3-(4-picolinoylaminophenethyl)-5-(3,4-dimethoxyphenyl)-6-ethyl-3,6-dihydro-1,3,4-thiadiazin-2-one 3-(4-picolinoylaminobenzyl)-5-(3,4-dimethoxyphenyl)-3,6-dihydro-1,3,4-oxadiazin-2-one 3-(3-picolinoylaminobenzyl)-5-(3,4-dimethoxyphenyl)-3,6-dihydro-1,3,4-oxadiazin-2-one 3-(2-picolinoylaminobenzyl)-5-(3,4-dimethoxyphenyl)-3,6-dihydro-1,3,4-oxadiazin-2-one 3-(4-picolinoylaminobenzyl)-5-(3,4-dimethoxyphenyl)-6-ethyl-3,6-dihydro-1,3,4-oxadiazin-2-one 3-(3-picolinoylaminobenzyl)-5-(3,4-dimethoxyphenyl)-6-ethyl-3,6-dihydro-1,3,4-oxadiazin-2-one 3-(2-picolinoylaminobenzyl)-5-(3,4-dimethoxyphenyl)-6-ethyl-3,6-dihydro-1,3,4-oxadiazin-2-one 3-(4-picolinoylaminobenzyl)-5-(3-methoxy-4-trifluoromethoxyphenyl)-6-ethyl-3,6-dihydro-1,3,4-oxadiazin-2-one 3-(4-picolinoylaminobenzyl)-5-(3-methoxy-4-difluoromethoxyphenyl)-6-ethyl-3,6-dihydro-1,3,4-oxadiazin-2-one 3-(4-picolinoylaminobenzyl)-5-(3-methoxy-4-fluoromethoxyphenyl)-6-ethyl-3,6-dihydro-1,3,4-oxadiazin-2-one 3-(4-picolinoylaminobenzyl)-5-(3-difluoromethoxy-4-methoxyphenyl)-6-ethyl-3,6-dihydro-1,3,4-oxadiazin-2-one 3-(4-picolinoylaminobenzyl)-5-(3-trifluoromethoxy-4-methoxyphenyl)-6-ethyl-3,6-dihydro-1,3,4-oxadiazin-2-one 3-(4-picolinoylaminobenzyl)-5-(3-fluoromethoxy-4-methoxyphenyl)-6-ethyl-3,6-dihydro-1,3,4-oxadiazin-2-one 3-(4-picolinoylaminobenzyl)-5-(3-methoxy-4-ethoxyphenyl)-6-ethyl-3,6-dihydro-1,3,4-oxadiazin-2-one 3-(4-picolinoylaminobenzyl)-5-(3-ethoxy-4-methoxyphenyl)-6-ethyl-3,6-dihydro-1,3,4-oxadiazin-2-one 3-(4-picolinoylaminobenzyl)-5-(3-hydroxy-4-methoxyphenyl)-6-ethyl-3,6-dihydro-1,3,4-oxadiazin-2-one 3-(4-picolinoylaminobenzyl)-5-(4-methysulfonylphenyl)-6-ethyl-3,6-dihydro-1,3,4-oxadiazin-2-one 3-(4-picolinoylaminobenzyl)-5-(4-methyleneoxyphenyl)-6-ethyl-3,6-dihydro-1,3,4-oxadiazin-2-one 3-(4-picolinoylaminobenzyl)-5-(3-cyclopentyloxy-4-methoxyphenyl)-6-ethyl-3,6-dihydro-1,3,4-oxadiazin-2-one 3-(3-picolinoylaminobenzyl)-5-(3-cyclopentyloxy-4-methoxyphenyl)-6-ethyl-3,6-dihydro-1,3,4-oxadiazin-2-one 3-(4-picolinoylaminophenethyl)-5-(3,4-dimethoxyphenyl)-3,6-dihydro-1,3,4-oxadiazin-2-one 3-(4-picolinoylaminophenethyl)-5-(3,4-dimethoxyphenyl)-6-ethyl-3,6-dihydro-1,3,4-oxadiazin-2-one.

Analogously, by reaction of the abovementioned "amine derivatives" with furan-2-carbonyl chloride, the compounds below are obtained 2-(4-(furan-2-carbonylamino)benzyl)-6-(3,4-dimethoxyphenyl)-2,3,4,5-tetrahydropyridazin-3-one 2-(3-(furan-2-carbonylamino)benzyl)-6-(3,4-dimethoxyphenyl)-2,3,4,5-tetrahydropyridazin-3-one 2-(2-(furan-2-carbonylamino)benzyl)-6-(3,4-dimethoxyphenyl)-2,3,4,5-tetrahydropyridazin-3-one 2-(4-(furan-2-carbonylamino)benzyl)-6-(3,4-dimethoxyphenyl)-5-ethyl-2,3,4,5-tetrahydropyridazin-3-one;

2-(3-(furan-2-carbonylamino)benzyl)-6-(3,4-dimethoxyphenyl)-5-ethyl-2,3,4,5-tetrahydropyridazin-3-one 2-(2-(furan-2-carbonylamino)benzyl)-6-(3,4-dimethoxyphenyl)-5-ethyl-2,3,4,5-tetrahydropyridazin-3-one 2-(4-(furan-2-carbonylamino)benzyl)-6-(3-methoxy-4-trifluoromethoxyphenyl)-5-ethyl-2,3,4,5-tetrahydropyridazin-3-one 2-(4-(furan-2-carbonylamino)benzyl)-6-(3-methoxy-4-difluoromethoxyphenyl)-5-ethyl-2,3,4,5-tetrahydropyridazin-3-one 2-(4-(furan-2-carbonylamino)benzyl)-6-(3-methoxy-4-fluoromethoxyphenyl)-5-ethyl-2,3,4,5-tetrahydropyridazin-3-one 2-(4-(furan-2-carbonylamino)benzyl)-6-(3-difluoromethoxy-4-methoxyphenyl)-5-ethyl-2,3,4,5-tetrahydropyridazin-3-one 2-(4-(furan-2-carbonylamino)benzyl)-6-(3-trifluoromethoxy-4-methoxyphenyl)-5-ethyl-2,3,4,5-tetrahydropyridazin-3-one 2-(4-(furan-2-carbonylamino)benzyl)-6-(3-fluoromethoxy-4-methoxyphenyl)-5-ethyl-2,3,4,5-tetrahydropyridazin-3-one 2-(4-(furan-2-carbonylamino)benzyl)-6-(3-methoxy-4-ethoxyphenyl)-5-ethyl-2,3,4,5-tetrahydropyridazin-3-one 2-(4-(furan-2-carbonylamino)benzyl)-6-(3-ethoxy-4-methoxyphenyl)-5-ethyl-2,3,4,5-tetrahydropyridazin-3-one 2-(4-(furan-2-carbonylamino)benzyl)-6-(3-hydroxy-4-methoxyphenyl)-5-ethyl-2,3,4,5-tetrahydropyridazin-3-one 2-(4-(furan-2-carbonylamino)benzyl)-6-(4-methylsulfonylphenyl)-5-ethyl-2,3,4,5-tetrahydropyridazin-3-one 2-(4-(furan-2-carbonylamino)benzyl)-6-(4-methyleneoxyphenyl)-5-ethyl-2,3,4,5-tetrahydropyridazin-3-one 2-(4-(furan-2-carbonylamino)benzyl)-6-(3-cyclopentyloxy-4-methoxyphenyl)-5-ethyl-2,3,4,5-tetrahydropyridazin-3-one 2-(3-(furan-2-carbonylamino)benzyl)-6-(3-cyclopentyloxy-4-methoxyphenyl)-5-ethyl-2,3,4,5-tetrahydropyridazin-3-one 2-(4-(furan-2-carbonylamino)phenethyl)-6-(3,4-dimethoxyphenyl)-2,3,4,5-tetrahydropyridazin-3-one 2-(4-(furan-2-carbonylamino)phenethyl)-6-(3,4-dimethoxyphenyl)-5-ethyl-2,3,4,5-tetrahydropyridazin-3-one 3-(4-(furan-2-carbonylamino)benzyl)-5-(3,4-dimethoxyphenyl)-3,6-dihydro-1,3,4-thiadiazin-2-one 3-(3-(furan-2-carbonylamino)benzyl)-5-(3,4-dimethoxyphenyl)-3,6-dihydro-1,3,4-thiadiazin-2-one 3-(2-(furan-2-carbonylamino)benzyl)-5-(3,4-dimethoxyphenyl)-3,6-dihydro-1,3,4-thiadiazin-2-one 3-(4-(furan-2-carbonylamino)benzyl)-5-(3,4-dimethoxyphenyl)-6-ethyl-3,6-dihydro-1,3,4-thiadiazin-2-one 3-(3-(furan-2-carbonylamino)benzyl)-5-(3,4-dimethoxyphenyl)-6-ethyl-3,6-dihydro-1,3,4-thiadiazin-2-one 3-(2-(furan-2-carbonylamino)benzyl)-5-(3,4-dimethoxyphenyl)-6-ethyl-3,6-dihydro-1,3,4-thiadiazin-2-one 3-(4-(furan-2-carbonylamino)benzyl)-5-(3-methoxy-4-trifluoromethoxyphenyl)-6-ethyl-3,6-dihydro-1,3,4-thiadiazin-2-one 3-(4-(furan-2-carbonylamino)benzyl)-5-(3-methoxy-4-difluoromethoxyphenyl)-6-ethyl-3,6-dihydro-1,3,4-thiadiazin-2-one 3-(4-(furan-2-carbonylamino)benzyl)-5-(3-methoxy-4-fluoromethoxyphenyl)-6-ethyl-3,6-dihydro-1,3,4-thiadiazin-2-one 3-(4-(furan-2-carbonylamino)benzyl)-5-(3-difluoromethoxy-4-methoxyphenyl)-6-ethyl-3,6-dihydro-1,3,4-thiadiazin-2-one 3-(4-(furan-2-carbonylamino)benzyl)-5-(3-trifluoromethoxy-4-methoxyphenyl)-6-ethyl-3,6-dihydro-1,3,4-thiadiazin-2-one 3-(4-(furan-2-carbonylamino)benzyl)-5-(3-fluoromethoxy-4-methoxyphenyl)-6-ethyl-3,6-dihydro-1,3,4-thiadiazin-2-one 3-(4-(furan-2-carbonylamino)benzyl)-5-(3-methoxy-4-ethoxyphenyl)-6-ethyl-3,6-dihydro-1,3,4-thiadiazin-2-one 3-(4-(furan-2-carbonylamino)benzyl)-5-(3-ethoxy-4-methoxyphenyl)-6-ethyl-3,6-dihydro-1,3,4-thiadiazin-2-one 3-(4-(furan-2-carbonylamino)benzyl)-5-(3-hydroxy-4-methoxyphenyl)-6-ethyl-3,6-dihydro-1,3,4-thiadiazin-2-one 3-(4-(furan-2-carbonylamino)benzyl)-5-(4-methylsulfonylphenyl)-6-ethyl-3,6-dihydro-1,3,4-thiadiazin-2-one 3-(4-(furan-2-carbonylamino)benzyl)-5-(4-methyleneoxyphenyl)-6-ethyl-3,6-dihydro-1,3,4-thiadiazin-2-one 3-(4-(furan-2-carbonylamino)benzyl)-5-(3-cyclopentyloxy-4-methoxyphenyl)-6-ethyl-3,6-dihydro-1,3,4-thiadiazin-2-one 3-(3-(furan-2-carbonylamino)benzyl)-5-(3-cyclopentyloxy-4-methoxyphenyl)-6-ethyl-3,6-dihydro-1,3,4-thiadiazin-2-one 3-(4-(furan-2-carbonylamino)phenethyl)-5-(3,4-dimethoxyphenyl)-3,6-dihydro-1,3,4-thiadiazin-2-one 3-(4-(furan-2-carbonylamino)phenethyl)-5-(3,4-dimethoxyphenyl)-6-ethyl-3,6-dihydro-1,3,4-thiadiazin-2-one 3-(4-(furan-2-carbonylamino)benzyl)-5-(3,4-dimethoxyphenyl)-3,6-dihydro-1,3,4-oxadiazin-2-one 3-(3-(furan-2-carbonylamino)benzyl)-5-(3,4-dimethoxyphenyl)-3,6-dihydro-1,3,4-oxadiazin-2-one 3-(2-(furan-2-carbonylamino)benzyl)-5-(3,4-dimethoxyphenyl)-3,6-dihydro-1,3,4-oxadiazin-2-one 3-(4-(furan-2-carbonylamino)benzyl)-5-(3,4-dimethoxyphenyl)-6-ethyl-3,6-dihydro-1,3,4-oxadiazin-2-one 3-(3-(furan-2-carbonylamino)benzyl)-5-(3,4-dimethoxyphenyl)-6-ethyl-3,6-dihydro-1,3,4-oxadiazin-2-one 3-(2-(furan-2-carbonylamino)benzyl)-5-(3,4-dimethoxyphenyl)-6-ethyl-3,6-dihydro-1,3,4-oxadiazin-2-one 3-(4-(furan-2-carbonylamino)benzyl)-5-(3-methoxy-4-trifluoromethoxyphenyl)-6-ethyl-3,6-dihydro-1,3,4-oxadiazin-2-one 3-(4-(furan-2-carbonylamino)benzyl)-5-(3-methoxy-4-difluoromethoxyphenyl)-6-ethyl-3,6-dihydro-1,3,4-oxadiazin-2-one 3-(4-(furan-2-carbonylamino)benzyl)-5-(3-methoxy-4-fluoromethoxyphenyl)-6-ethyl-3,6-dihydro-1,3,4-oxadiazin-2-one 3-(4-(furan-2-carbonylamino)benzyl)-5-(3-difluoromethoxy-4-methoxyphenyl)-6-ethyl-3,6-dihydro-1,3,4-oxadiazin-2-one 3-(4-(furan-2-carbonylamino)benzyl)-5-(3-trifluoromethoxy-4-methoxyphenyl)-6-ethyl-3,6-dihydro-1,3,4-oxadiazin-2-one 3-(4-(furan-2-carbonylamino)benzyl)-5-(3-fluoromethoxy-4-methoxyphenyl)-6-ethyl-3,6-dihydro-1,3,4-oxadiazin-2-one 3-(4-(furan-2-carbonylamino)benzyl)-5-(3-methoxy-4-ethoxyphenyl)-6-ethyl-3,6-dihydro-1,3,4-oxadiazin-2-one 3-(4-(furan-2-carbonylamino)benzyl)-5-(3-ethoxy-4-methoxyphenyl)-6-ethyl-3,6-dihydro-1,3,4-oxadiazin-2-one 3-(4-(furan-2-carbonylamino)benzyl)-5-(3-hydroxy-4-methoxyphenyl)-6-ethyl-3,6-dihydro-1,3,4-oxadiazin-2-one 3-(4-(furan-2-carbonylamino)benzyl)-5-(4-methylsulfonylphenyl)-6-ethyl-3,6-dihydro-1,3,4-oxadiazin-2-one 3-(4-(furan-2-carbonylamino)benzyl)-5-(4-methyleneoxyphenyl)-6-ethyl-3,6-dihydro-1,3,4-oxadiazin-2-one 3-(4-(furan-2-carbonylamino)benzyl)-5-(3-cyclopentyloxy-4-methoxyphenyl)-6-ethyl-3,6-dihydro-1,3,4-oxadiazin-2-one 3-(3-(furan-2-carbonylamino)benzyl)-5-(3-cyclopentyloxy-4-methoxyphenyl)-6-ethyl-3,6-dihydro-1,3,4-oxadiazin-2-one 3-(4-(furan-2-carbonylamino)phenethyl)-5-(3,4-dimethoxyphenyl)-3,6-dihydro-1,3,4-oxadiazin-2-one 3-(4-(furan-2-carbonylamino)phenethyl)-5-(3,4-dimethoxyphenyl)6-ethyl-3,6-dihydro-1,3,4-oxadiazin-2-one.

Analogously, by reaction of the abovementioned "amine derivatives" with pyrrole-2-carbonyl, chloride the compounds below are obtained 2-(4-(pyrrole-2-carbonylamino)benzyl)-6-(3,4-dimethoxyphenyl)-2,3,4,5-tetrahydropyridazin-3-one 2-(3-(pyrrole-2-carbonylamino)benzyl)-6-(3,4-dimethoxyphenyl)-2,3,4,5-tetrahydropyridazin-3-one 2-(2-(pyrrole-2-carbonylamino)benzyl)-6-(3,4-dimethoxyphenyl)-2,3,4,5-tetrahydropyridazin-3-one 2-(4-(pyrrole-2-carbonylamino)benzyl)-6-(3,4-dimethoxyphenyl)-5-ethyl-2,3,4,5-tetrahydropyridazin-3-one;

2-(3-(pyrrole-2-carbonylamino)benzyl)-6-(3,4-dimethoxyphenyl)-5-ethyl-2,3,4,5-tetrahydropyridazin-3-one 2-(2-(pyrrole-2-carbonylamino)benzyl)-6-(3,4-dimethoxyphenyl)-5-ethyl-2,3,4,5-tetrahydropyridazin-3-one 2-(4-(pyrrole-2-carbonylamino)benzyl)-6-(3-methoxy-4-trifluoromethoxyphenyl)-5-ethyl-2,3,4,5-tetrahydropyridazin-3-one 2-(4-(pyrrole-2-carbonylamino)benzyl)-6-(3-methoxy-4-difluoromethoxyphenyl)-5-ethyl-2,3,4,5-tetrahydropyridazin-3-one 2-(4-(pyrrole-2-carbonylamino)benzyl)-6-(3-methoxy-4-fluoromethoxyphenyl)-5-ethyl-2,3,4,5-tetrahydropyridazin-3-one 2-(4-(pyrrole-2-carbonylamino)benzyl)-6-(3-difluoromethoxy-4-methoxyphenyl)-5-ethyl-2,3,4,5-tetrahydropyridazin-3-one 2-(4-(pyrrole-2-carbonylamino)benzyl)-6-(3-trifluoromethoxy-4-methoxyphenyl)-5-ethyl-2,3,4,5-tetrahydropyridazin-3-one 2-(4-(pyrrole-2-carbonylamino)benzyl)-6-(3-fluoromethoxy-4-methoxyphenyl)-5-ethyl-2,3,4,5-tetrahydropyridazin-3-one 2-(4-(pyrrole-2-carbonylamino)benzyl)-6-(3-methoxy-4-ethoxyphenyl)-5-ethyl-2,3,4,5-tetrahydropyridazin-3-one 2-(4-(pyrrole-2-carbonylamino)benzyl)-6-(3-ethoxy-4-methoxyphenyl)-5-ethyl-2,3,4,5-tetrahydropyridazin-3-one 2-(4-(pyrrole-2-carbonylamino)benzyl)-6-(3-hydroxy-4-methoxyphenyl)-5-ethyl-2,3,4,5-tetrahydropyridazin-3-one 2-(4-(pyrrole-2-carbonylamino)benzyl)-6-(4-methylsulfonylphenyl)-5-ethyl-2,3,4,5-tetrahydropyridazin-3-one 2-(4-(pyrrole-2-carbonylamino)benzyl)-6-(4-methyleneoxyphenyl)-5-ethyl-2,3,4,5-tetrahydropyridazin-3-one 2-(4-(pyrrole-2-carbonylamino)benzyl)-6-(3-cyclopentyloxy-4-methoxyphenyl)-5-ethyl-2,3,4,5-tetrahydropyridazin-3-one 2-(3-(pyrrole-2-carbonylamino)benzyl)-6-(3-cyclopentyloxy-4-methoxyphenyl)-5-ethyl-2,3,4,5-tetrahydropyridazin-3-one 2-(4-(pyrrole-2-carbonylamino)phenethyl)-6-(3,4-dimethoxyphenyl)-2,3,4,5-tetrahydropyridazin-3-one 2-(4-(pyrrole-2-carbonylamino)phenethyl)-6-(3,4-dimethoxyphenyl)-5-ethyl-2,3,4,5-tetrahydropyridazin-3-one 3-(4-(pyrrole-2-carbonylamino)benzyl)-5-(3,4-dimethoxyphenyl)-3,6-dihydro-1,3,4-thiadiazin-2-one 3-(3-(pyrrole-2-carbonylamino)benzyl)-5-(3,4,dimethoxyphenyl)-3,6-dihydro-1,3,4-thiadiazin-2-one 3-(2-(pyrrole-2-carbonylamino)benzyl)-5-(3,4,dimethoxyphenyl)-3,6-dihydro-1,3,4-thiadiazin-2-one 3-(4-(pyrrole-2-carbonylamino)benzyl)-5-(3,4,dimethoxyphenyl)-6-ethyl-3,6-dihydro-1,3,4-thiadiazin-2-one 3-(3-(pyrrole-2-carbonylamino)benzyl)-5-(3,4,dimethoxyphenyl)-6-ethyl-3,6-dihydro-1,3,4-thiadiazin-2-one 3-(2-(pyrrole-2-carbonylamino)benzyl)-5-(3,4,dimethoxyphenyl)-6-ethyl-3,6-dihydro-1,3,4-thiadiazin-2-one 3-(4-(pyrrole-2-carbonylamino)benzyl)-5-(3-methoxy-4-trifluoromethoxyphenyl)-6-ethyl-3,6-dihydro-1,3,4-thiadiazin-2-one 3-(4-(pyrrole-2-carbonylamino)benzyl)-5-(3-methoxy-4-difluoromethoxyphenyl)-6-ethyl-3,6-dihydro-1,3,4-thiadiazin-2-one 3-(4-(pyrrole-2-carbonylamino)benzyl)-5-(3-methoxy-4-fluoromethoxyphenyl)-6-ethyl-3,6-dihydro-1,3,4-thiadiazin-2-one 3-(4-(pyrrole-2-carbonylamino)benzyl)-5-(3-difluoromethoxy-4-methoxyphenyl)-6-ethyl-3,6-dihydro-1,3,4-thiadiazin-2-one 3-(4-(pyrrole-2-carbonylamino)benzyl)-5-(3-trifluoromethoxy-4-methoxyphenyl)-6-ethyl-3,6-dihydro-1,3,4-thiadiazin-2-one 3-(4-(pyrrole-2-carbonylamino)benzyl)-5-(3-fluoromethoxy-4-methoxyphenyl)-6-ethyl-3,6-dihydro-1,3,4-thiadiazin-2-one 3-(4-(pyrrole-2-carbonylamino)benzyl)-5-(3-methoxy-4-ethoxyphenyl)-6-ethyl-3,6-dihydro-1,3,4-thiadiazin-2-one
3-(4-(pyrrole-2-carbonylamino)benzyl)-5-(3-ethoxy-4-methoxyphenyl)-6-ethyl-3,6-dihydro-1,3,4-thiadiazin-2-one
3-(4-(pyrrole-2-carbonylamino)benzyl)-5-(3-hydroxy-4-methoxyphenyl)-6-ethyl-3,6-dihydro-1,3,4-thiadiazin-2-one
3-(4-(pyrrole-2-carbonylamino)benzyl)-5-(4-methylsulfonylphenyl)-6-ethyl-3,6-dihydro-1,3,4-thiadiazin-2-one
3-(4-(pyrrole-2-carbonylamino)benzyl)-5-(4-methyleneoxyphenyl)-6-ethyl-3,6-dihydro-1,3,4-thiadiazin-2-one
3-(4-(pyrrole-2-carbonylamino)benzyl)-5-(3-cyclopentyloxy-4-methoxyphenyl)-6-ethyl-3,6-dihydro-1,3,4-thiadiazin-2-one
3-(3-(pyrrole-2-carbonylamino)benzyl)-5-(3-cyclopentyloxy-4-methoxyphenyl)-6-ethyl-3,6-dihydro-1,3,4-thiadiazin-2-one
3-(4-(pyrrole-2-carbonylamino)phenethyl)-5-(3,4-dimethoxyphenyl)-3,6-dihydro-1,3,4-thiadiazin-2-one
3-(4-(pyrrole-2-carbonylamino)phenethyl)-5-(3,4-dimethoxyphenyl)-6-ethyl-3,6-dihydro-1,3,4-thiadiazin-2-one
3-(4-(pyrrole-2-carbonylamino)benzyl)-5-(3,4-dimethoxyphenyl)-3,6-dihydro-1,3,4-oxadiazin-2-one
3-(3-(pyrrole-2-carbonylamino)benzyl)-5-(3,4-dimethoxyphenyl)-3,6-dihydro-1,3,4-oxadiazin-2-one
3-(2-(pyrrole-2-carbonylamino)benzyl)-5-(3,4-dimethoxyphenyl)-3,6-dihydro-1,3,4-oxadiazin-2-one
3-(4-(pyrrole-2-carbonylamino)benzyl)-5-(3,4-dimethoxyphenyl)-6-ethyl-3,6-dihydro-1,3,4-oxadiazin-2-one
3-(3-(pyrrole-2-carbonylamino)benzyl)-5-(3,4-dimethoxyphenyl)-6-ethyl-3,6-dihydro-1,3,4-oxadiazin-2-one
3-(2-(pyrrole-2-carbonylamino)benzyl)-5-(3,4-dimethoxyphenyl)-6-ethyl-3,6-dihydro-1,3,4-oxadiazin-2-one
3-(4-(pyrrole-2-carbonylamino)benzyl)-5-(3-methoxy-4-trifluoromethoxyphenyl)-6-ethyl-3,6-dihydro-1,3,4-oxadiazin-2-one
3-(4-(pyrrole-2-carbonylamino)benzyl)-5-(3-methoxy-4-difluoromethoxyphenyl)-6-ethyl-3,6-dihydro-1,3,4-oxadiazin-2-one
3-(4-(pyrrole-2-carbonylamino)benzyl)-5-(3-methoxy-4-fluoromethoxyphenyl)-6-ethyl-3,6-dihydro-1,3,4-oxadiazin-2-one
3-(4-(pyrrole-2-carbonylamino)benzyl)-5-(3-difluoromethoxy-4-methoxyphenyl)-6-ethyl-3,6-dihydro-1,3,4-oxadiazin-2-one
3-(4-(pyrrole-2-carbonylamino)benzyl)-5-(3-trifluoromethoxy-4-methoxyphenyl)-6-ethyl-3,6-dihydro-1,3,4-oxadiazin-2-one
3-(4-(pyrrole-2-carbonylamino)benzyl)-5-(3-fluoromethoxy-4-methoxyphenyl)-6-ethyl-3,6-dihydro-1,3,4-oxadiazin-2-one
3-(4-(pyrrole-2-carbonylamino)benzyl)-5-(3-methoxy-4-ethoxyphenyl)-6-ethyl-3,6-dihydro-1,3,4-oxadiazin-2-one
3-(4-(pyrrole-2-carbonylamino)benzyl)-5-(3-ethoxy-4-methoxyphenyl)-6-ethyl-3,6-dihydro-1,3,4-oxadiazin-2-one
3-(4-(pyrrole-2-carbonylamino)benzyl)-5-(3-hydroxy-4-methoxyphenyl)-6-ethyl-3,6-dihydro-1,3,4-oxadiazin-2-one
3-(4-(pyrrole-2-carbonylamino)benzyl)-5-(4-methylsulfonylphenyl)-6-ethyl-3,6-dihydro-1,3,4-oxadiazin-2-one
3-(4-(pyrrole-2-carbonylamino)benzyl)-5-(4-methyleneoxyphenyl)-6-ethyl-3,6-dihydro-1,3,4-oxadiazin-2-one
3-(4-(pyrrole-2-carbonylamino)benzyl)-5-(3-cyclopentyloxy-4-methoxyphenyl)-6-ethyl-3,6-dihydro-1,3,4-oxadiazin-2-one
3-(3-(pyrrole-2-carbonylamino)benzyl)-5-(3-cyclopentyloxy-4-methoxyphenyl)-6-ethyl-3,6-dihydro-1,3,4-oxadiazin-2-one
3-(4-(pyrrole-2-carbonylamino)phenethyl)-5-(3,4-dimethoxyphenyl)-3,6-dihydro-1,3,4-oxadiazin-2-one
3-(4-(pyrrole-2-carbonylamino)phenethyl)-5-(3,4-dimethoxyphenyl)-6-ethyl-3,6-dihydro-1,3,4-oxadiazin-2-one.

Analogously, by reaction of the abovementioned "amine derivatives" with thiophene-2-carbonyl chloride, the compounds below are obtained 2-(4-(thiophene-2-carbonylamino)benzyl)-6-(3,4-dimethoxyphenyl)-2,3,4,5-tetrahydropyridazin-3-one
2-(3-(thiophene-2-carbonylamino)benzyl)-6-(3,4-dimethoxyphenyl)-2,3,4,5-tetrahydropyridazin-3-one
2-(2-(thiophene-2-carbonylamino)benzyl)-6-(3,4-dimethoxyphenyl)-2,3,4,5-tetrahydropyridazin-3-one
2-(4-(thiophene-2-carbonylamino)benzyl)-6-(3,4-dimethoxyphenyl)-5-ethyl-2,3,4,5-tetrahydropyridazin-3-one;
2-(3-(thiophene-2-carbonylamino)benzyl)-6-(3,4-dimethoxyphenyl)-5-ethyl-2,3,4,5-tetrahydropyridazin-3-one
2-(2-(thiophene-2-carbonylamino)benzyl)-6-(3,4-dimethoxyphenyl)-5-ethyl-2,3,4,5-tetrahydropyridazin-3-one
2-(4-(thiophene-2-carbonylamino)benzyl)-6-(3-methoxy-4-trifluoromethoxyphenyl)-5-ethyl-2,3,4,5-tetrahydropyridazin-3-one
2-(4-(thiophene-2-carbonylamino)benzyl)-6-(3-methoxy-4-difluoromethoxyphenyl)-5-ethyl-2,3,4,5-tetrahydropyridazin-3-one
2-(4-(thiophene-2-carbonylamino)benzyl)-6-(3-methoxy-4-fluoromethoxyphenyl)-5-ethyl-2,3,4,5-tetrahydropyridazin-3-one
2-(4-(thiophene-2-carbonylamino)benzyl)-6-(3-difluoromethoxy-4-methoxyphenyl)-5-ethyl-2,3,4,5-tetrahydropyridazin-3-one
2-(4-(thiophene-2-carbonylamino)benzyl)-6-(3-trifluoromethoxy-4-methoxyphenyl)-5-ethyl-2,3,4,5-tetrahydropyridazin-3-one
2-(4-(thiophene-2-carbonylamino)benzyl)-6-(3-fluoromethoxy-4-methoxyphenyl)-5-ethyl-2,3,4,5-tetrahydropyridazin-3-one
2-(4-(thiophene-2-carbonylamino)benzyl)-6-(3-methoxy-4-ethoxyphenyl)-5-ethyl-2,3,4,5-tetrahydropyridazin-3-one
2-(4-(thiophene-2-carbonylamino)benzyl)-6-(3-ethoxy-4-methoxyphenyl)-5-ethyl-2,3,4,5-tetrahydropyridazin-3-one
2-(4-(thiophene-2-carbonylamino)benzyl)-6-(3-hydroxy-4-methoxyphenyl)-5-ethyl-2,3,4,5-tetrahydropyridazin-3-one
2-(4-(thiophene-2-carbonylamino)benzyl)-6-(4-methylsulfonylphenyl)-5-ethyl-2,3,4,5-tetrahydropyridazin-3-one
2-(4-(thiophene-2-carbonylamino)benzyl)-6-(4-methyleneoxyphenyl)-5-ethyl-2,3,4,5-tetrahydropyridazin-3-one 2-(4-(thiophene-2-carbonylamino)benzyl)-6-(3-cyclopentyloxy-4-methoxyphenyl)-5-ethyl-2,3,4,5-tetrahydropyridazin-3-one
2-(3-(thiophene-2-carbonylamino)benzyl)-6-(3-cyclopentyloxy-4-methoxyphenyl)-5-ethyl-2,3,4,5-tetrahydropyridazin-3-one
2-(4-(thiophene-2-carbonylamino)phenethyl)-6-(3,4-dimethoxyphenyl)-2,3,4,5-tetrahydropyridazin-3-one
2-(4-(thiophene-2-carbonylamino)phenethyl)-6-(3,4-dimethoxyphenyl)-5-ethyl-2,3,4,5-tetrahydropyridazin-3-one
3-(4-(thiophene-2-carbonylamino)benzyl)-5-(3,4-dimethoxyphenyl)-3,6-dihydro-1,3,4-thiadiazin-2-one, m.p. 186°
3-(3-(thiophene-2-carbonylamino)benzyl)-5-(3,4-dimethoxyphenyl)-3,6-dihydro-1,3,4-thiadiazin-2-one
3-(2-(thiophene-2-carbonylamino)benzyl)-5-(3,4-dimethoxyphenyl)-3,6-dihydro-1,3,4-thiadiazin-2-one
3-(4-(thiophene-2-carbonylamino)benzyl)-5-(3,4-dimethoxyphenyl)-6-ethyl-3,6-dihydro-1,3,4-thiadiazin-2-one
3-(3-(thiophene-2-carbonylamino)benzyl)-5-(3,4-dimethoxyphenyl)-6-ethyl-3,6-dihydro-1,3,4-thiadiazin-2-one
3-(2-(thiophene-2-carbonylamino)benzyl)-5-(3,4-dimethoxyphenyl)-6-ethyl-3,6-dihydro-1,3,4-thiadiazin-2-one
3-(4-(thiophene-2-carbonylamino)benzyl)-5-(3-methoxy-4-trifluoromethoxyphenyl)-6-ethyl-3,6-dihydro-1,3,4-thiadiazin-2-one
3-(4-(thiophene-2-carbonylamino)benzyl)-5-(3-methoxy-4-difluoromethoxyphenyl)-6-ethyl-3,6-dihydro-1,3,4-thiadiazin-2-one
3-(4-(thiophene-2-carbonylamino)benzyl)-5-(3-methoxy-4-fluoromethoxyphenyl)-6-ethyl-3,6-dihydro-1,3,4-thiadiazin-2-one
3-(4-(thiophene-2-carbonylamino)benzyl)-5-(3-difluoromethoxy-4-methoxyphenyl)-6-ethyl-3,6-dihydro-1,3,4-thiadiazin-2-one
3-(4-(thiophene-2-carbonylamino)benzyl)-5-(3-trifluoromethoxy-4-methoxyphenyl)-6-ethyl,3,6-dihydro-1,3,4-thiadiazin-2-one
3-(4-(thiophene-2-carbonylamino)benzyl)-5-(3-fluoromethoxy-4-methoxyphenyl)-6-ethyl-3,6-dihydro-1,3,4-thiadiazin-2-one
3-(4-(thiophene-2-carbonylamino)benzyl)-5-(3-methoxy-4-ethoxyphenyl)-6-ethyl-3,6-dihydro-1,3,4-thiadiazin-2-one
3-(4-(thiophene-2-carbonylamino)benzyl)-5-(3-ethoxy-4-methoxyphenyl)-6-ethyl-3,6-dihydro-1,3,4-thiadiazin-2-one
3-(4-(thiophene-2-carbonylamino)benzyl)-5-(3-hydroxy-4-methoxyphenyl)-6-ethyl-3,6-dihydro-1,3,4-thiadiazin-2-one
3-(4-(thiophene-2-carbonylamino)benzyl)-5-(4-methylsulfonylphenyl)-6-ethyl-3,6-dihydro-1,3,4-thiadiazin-2-one
3-(4-(thiophene-2-carbonylamino)benzyl)-5-(4-methyleneoxyphenyl)-6-ethyl-3,6-dihydro-1,3,4-thiadiazin-2-one
3-(4-(thiophene-2-carbonylamino)benzyl)-5-(3-cyclopentyloxy-4-methoxyphenyl)-6-ethyl-3,6-dihydro-1,3,4-thiadiazin-2-one
3-(3-(thiophene-2-carbonylamino)benzyl)-5-(3-cyclopentyloxy-4-methoxyphenyl)-6-ethyl-3,6-dihydro-1,3,4-thiadiazin-2-one
3-(4-(thiophene-2-carbonylamino)phenethyl)-5-(3,4-dimethoxyphenyl)-3,6-dihydro-1,3,4-thiadiazin-2-one
3-(4-(thiophene-2-carbonylamino)phenethyl)-5-(3,4-dimethoxyphenyl)-6-ethyl-3,6-dihydro-1,3,4-thiadiazin-2-one
3-(4-(thiophene-2-carbonylamino)benzyl)-5-(3,4-dimethoxyphenyl)-3,6-dihydro-1,3,4-oxadiazin-2-one
3-(3-(thiophene-2-carbonylamino)benzyl)-5-(3,4-dimethoxyphenyl)-3,6-dihydro-1,3,4-oxadiazin-2-one
3-(2-(thiophene-2-carbonylamino)benzyl)-5-(3,4-dimethoxyphenyl)-3,6-dihydro-1,3,4-oxadiazin-2-one
3-(4-(thiophene-2-carbonylamino)benzyl)-5-(3,4-dimethoxyphenyl)-6-ethyl-3,6-dihydro-1,3,4-oxadiazin-2-one
3-(3-(thiophene-2-carbonylamino)benzyl)-5-(3,4-dimethoxyphenyl)-6-ethyl-3,6-dihydro-1,3,4-oxadiazin-2-one
3-(2-(thiophene-2-carbonylamino)benzyl)-5-(3,4-dimethoxyphenyl)-6-ethyl-3,6-dihydro-1,3,4-oxadiazin-2-one
3-(4-(thiophene-2-carbonylamino)benzyl)-5-(3-methoxy-4-trifluoromethoxyphenyl)-6-ethyl-3,6-dihydro-1,3,4-oxadiazin-2-one
3-(4-(thiophene-2-carbonylamino)benzyl)-5-(3-methoxy-4-difluoromethoxyphenyl)-6-ethyl-3,6-dihydro-1,3,4-oxadiazin-2-one
3-(4-(thiophene-2-carbonylamino)benzyl)-5-(3-methoxy-4-fluoromethoxyphenyl)-6-ethyl-3,6-dihydro-1,3,4-oxadiazin-2-one
3-(4-(thiophene-2-carbonylamino)benzyl)-5-(3-difluoromethoxy-4-methoxyphenyl)-6-ethyl-3,6-dihydro-1,3,4-oxadiazin-2-one
3-(4-(thiophene-2-carbonylamino)benzyl)-5-(3-trifluoromethoxy-4-methoxyphenyl)-6-ethyl-3,6-dihydro-1,3,4-oxadiazin-2-one
3-(4-(thiophene-2-carbonylamino)benzyl)-5-(3-fluoromethoxy-4-methoxyphenyl)-6-ethyl-3,6-dihydro-1,3,4-oxadiazin-2-one
3-(4-(thiophene-2-carbonylamino)benzyl)-5-(3-methoxy-4-ethoxyphenyl)-6-ethyl-3,6-dihydro-1,3,4-oxadiazin-2-one
3-(4-(thiophene-2-carbonylamino)benzyl)-5-(3-ethoxy-4-methoxyphenyl)-6-ethyl-3,6-dihydro-1,3,4-oxadiazin-2-one
3-(4-(thiophene-2-carbonylamino)benzyl)-5-(3-hydroxy-4-methoxyphenyl)-6-ethyl-3,6-dihydro-1,3,4-oxadiazin-2-one
3-(4-(thiophene-2-carbonylamino)benzyl)-5-(4-methylsulfonylphenyl)-6-ethyl-3,6-dihydro-1,3,4-oxadiazin-2-one
3-(4-(thiophene-2-carbonylamino)benzyl)-5-(4-methyleneoxyphenyl)-6-ethyl-3,6-dihydro-1,3,4-oxadiazin-2-one
3-(4-(thiophene-2-carbonylamino)benzyl)-5-(3-cyclopentyloxy-4-methoxyphenyl)-6-ethyl-3,6-dihydro-1,3,4-oxadiazin-2-one
3-(3-(thiophene-2-carbonylamino)benzyl)-5-(3-cyclopentyloxy-4-methoxyphenyl)-6-ethyl-3,6-dihydro-1,3,4-oxadiazin-2-one
3-(4-(thiophene-2-carbonylamino)phenethyl)-5-(3,4-dimethoxyphenyl)-3,6-dihydro-1,3,4-oxadiazin-2-one
3-(4-(thiophene-2-carbonylamino)phenethyl)-5-(3,4-dimethoxyphenyl)-6-ethyl-3,6-dihydro-1,3,4-oxadiazin-2-one.

Analogously, by reaction of the abovementioned "amine derivatives" with pyrazine-2-carbonyl chloride, the compounds below are obtained 2-(4-pyrazinecarbonylaminobenzyl)-6-(3,4-dimethoxyphenyl)-2,3,4,5-tetrahydropyridazin-3-one, m.p. 197°

2-(3-pyrazinecarbonylaminobenzyl)-6-(3,4-dimethoxyphenyl)-2,3,4,5-tetrahydropyridazin-3-one 2-(2-pyrazinecarbonylaminobenzyl)-6-(3,4-dimethoxyphenyl)-2,3,4,5-tetrahydropyridazin-3-one 2-(4-pyrazinecarbonylaminobenzyl)-6-(3,4-dimethoxyphenyl)-5-ethyl-2,3,4,5-tetrahydropyridazin-3-one;

2-(3-pyrazinecarbonylaminobenzyl)-6-(3,4-dimethoxyphenyl)-5-ethyl-2,3,4,5-tetrahydropyridazin-3-one 2-(2-pyrazinecarbonylaminobenzyl)-6-(3,4-dimethoxyphenyl)-5-ethyl-2,3,4,5-tetrahydropyridazin-3-one 2-(4-pyrazinecarbonylaminobenzyl)-6-(3-methoxy-4-trifluoromethoxyphenyl)-5-ethyl-2,3,4,5-tetrahydropyridazin-3-one 2-(4-pyrazinecarbonylaminobenzyl)-6-(3-methoxy-4-difluoromethoxyphenyl)-5-ethyl-2,3,4,5-tetrahydropyridazin-3-one 2-(4-pyrazinecarbonylaminobenzyl)-6-(3-methoxy-4-fluoromethoxyphenyl)-5-ethyl-2,3,4,5-tetrahydropyridazin-3-one 2-(4-pyrazinecarbonylaminobenzyl)-6-(3-difluoromethoxy-4-methoxyphenyl)-5-ethyl-2,3,4,5-tetrahydropyridazin-3-one 2-(4-pyrazinecarbonylaminobenzyl)-6-(3-trifluoromethoxy-4-methoxyphenyl)-5-ethyl-2,3,4,5-tetrahydropyridazin-3-one 2-(4-pyrazinecarbonylaminobenzyl)-6-(3-fluoromethoxy-4-methoxyphenyl)-5-ethyl-2,3,4,5-tetrahydropyridazin-3-one 2-(4-pyrazinecarbonylaminobenzyl)-6-(3-methoxy-4-ethoxyphenyl)-5-ethyl-2,3,4,5-tetrahydropyridazin-3-one 2-(4-pyrazinecarbonylaminobenzyl)-6-(3-ethoxy-4-methoxyphenyl)-5-ethyl-2,3,4,5-tetrahydropyridazin-3-one 2-(4-pyrazinecarbonylaminobenzyl)-6-(3-hydroxy-4-methoxyphenyl)-5-ethyl-2,3,4,5-tetrahydropyridazin-3-one 2-(4-pyrazinecarbonylaminobenzyl)-6-(4-methylsulfonylphenyl)-5-ethyl-2,3,4,5-tetrahydropyridazin-3-one 2-(4-pyrazinecarbonylaminobenzyl)-6-(4-methyleneoxyphenyl)-5-ethyl-2,3,4,5-tetrahydropyridazin-3-one 2-(4-pyrazinecarbonylaminobenzyl)-6-(3-cyclopentyloxy-4-methoxyphenyl)-5-ethyl-2,3,4,5-tetrahydropyridazin-3-one 2-(3-pyrazinecarbonylaminobenzyl)-6-(3-cyclopentyloxy-4-methoxyphenyl)-5-ethyl-2,3,4,5-tetrahydropyridazin-3-one 2-(4-pyrazinecarbonylaminophenethyl)-6-(3,4-dimethoxyphenyl)-2,3,4,5-tetrahydropyridazin-3-one 2-(4-pyrazinecarbonylaminophenethyl)-6-(3,4-dimethoxyphenyl)-5-ethyl-2,3,4,5-tetrahydropyridazin-3-one 3-(4-pyrazinecarbonylaminobenzyl)-5-(3,4-dimethoxyphenyl)-3,6-dihydro-1,3,4-thiadiazin-2-one, m.p. 202°

3-(3-pyrazinecarbonylaminobenzyl)-5-(3,4-dimethoxyphenyl)-3,6-dihydro-1,3,4-thiadiazin-2-one 3-(2-pyrazinecarbonylaminobenzyl)-5-(3,4-dimethoxyphenyl)-3,6-dihydro-1,3,4-thiadiazin-2-one 3-(4-pyrazinecarbonylaminobenzyl)-5-(3,4-dimethoxyphenyl)-6-ethyl-3,6-dihydro-1,3,4-thiadiazin-2-one 3-(3-pyrazinecarbonylaminobenzyl)-5-(3,4-dimethoxyphenyl)-6-ethyl-3,6-dihydro-1,3,4-thiadiazin-2-one 3-(2-pyrazinecarbonylaminobenzyl)-5-(3,4-dimethoxyphenyl)-6-ethyl-3,6-dihydro-1,3,4-thiadiazin-2-one 3-(4-pyrazinecarbonylaminobenzyl)-5-(3-methoxy-4-trifluoromethoxyphenyl)-6-ethyl-3,6-dihydro-1,3,4-thiadiazin-2-one 3-(4-pyrazinecarbonylaminobenzyl)-5-(3-methoxy-4-difluoromethoxyphenyl)-6-ethyl-3,6-dihydro-1,3,4-thiadiazin-2-one 3-(4-pyrazinecarbonylaminobenzyl)-5-(3-methoxy-4-fluoromethoxyphenyl)-6-ethyl-3,6-dihydro-1,3,4-thiadiazin-2-one 3-(4-pyrazinecarbonylaminobenzyl)-5-(3-difluoromethoxy-4-methoxyphenyl)-6-ethyl-3,6-dihydro-1,3,4-thiadiazin-2-one 3-(4-pyrazinecarbonylaminobenzyl)-5-(3-trifluoromethoxy-4-methoxyphenyl)-6-ethyl-3,6-dihydro-1,3,4-thiadiazin-2-one 3-(4-pyrazinecarbonylaminobenzyl)-5-(3-fluoromethoxy-4-methoxyphenyl)-6-ethyl-3,6-dihydro-1,3,4-thiadiazin-2-one 3-(4-pyrazinecarbonylaminobenzyl)-5-(3-methoxy-4-ethoxyphenyl)-6-ethyl-3,6-dihydro-1,3,4-thiadiazin-2-one 3-(4-pyrazinecarbonylaminobenzyl)-5-(3-ethoxy-4-methoxyphenyl)-6-ethyl-3,6-dihydro-1,3,4-thiadiazin-2-one 3-(4-pyrazinecarbonylaminobenzyl)-5-(3-hydroxy-4-methoxyphenyl)-6-ethyl-3,6-dihydro-1,3,4-thiadiazin-2-one 3-(4-pyrazinecarbonylaminobenzyl)-5-(4-methylsulfonylphenyl)-6-ethyl-3,6-dihydro-1,3,4-thiadiazin-2-one 3-(4-pyrazinecarbonylaminobenzyl)-5-(4-methyleneoxyphenyl)-6-ethyl-3,6-dihydro-1,3,4-thiadiazin-2-one 3-(4-pyrazinecarbonylaminobenzyl)-5-(3-cyclopentyloxy-4-methoxyphenyl)-6-ethyl-3,6-dihydro-1,3,4-thiadiazin-2-one 3-(3-pyrazinecarbonylaminobenzyl)-5-(3-cyclopentyloxy-4-methoxyphenyl)-6-ethyl-3,6-dihydro-1,3,4-thiadiazin-2-one 3-(4-pyrazinecarbonylaminophenethyl)-5-(3,4-dimethoxyphenyl)-3,6-dihydro-1,3,4-thiadiazin-2-one 3-(4-pyrazinecarbonylaminophenethyl)-5-(3,4-dimethoxyphenyl)-6-ethyl-3,6-dihydro-1,3,4-thiadiazin-2-one 3-(4-pyrazinecarbonylaminobenzyl)-5-(3,4-dimethoxyphenyl)-3,6-dihydro-1,3,4-oxadiazin-2-one 3-(3-pyrazinecarbonylaminobenzyl)-5-(3,4-dimethoxyphenyl)-3,6-dihydro-1,3,4-oxadiazin-2-one 3-(2-pyrazinecarbonylaminobenzyl)-5-(3,4-dimethoxyphenyl)-3,6-dihydro-1,3,4-oxadiazin-2-one 3-(4-pyrazinecarbonylaminobenzyl)-5-(3,4-dimethoxyphenyl)-6-ethyl-3,6-dihydro-1,3,4-oxadiazin-2-one 3-(3-pyrazinecarbonylaminobenzyl)-5-(3,4-dimethoxyphenyl)-6-ethyl-3,6-dihydro-1,3,4-oxadiazin-2-one 3-(2-pyrazinecarbonylaminobenzyl)-5-(3,4-dimethoxyphenyl)-6-ethyl-3,6-dihydro-1,3,4-oxadiazin-2-one 3-(4-pyrazinecarbonylaminobenzyl)-5-(3-methoxy-4-trifluoromethoxyphenyl)-6-ethyl-3,6-dihydro-1,3,4-oxadiazin-2-one 3-(4-pyrazinecarbonylaminobenzyl)-5-(3-methoxy-4-difluoromethoxyphenyl)-6-ethyl-3,6-dihydro-1,3,4-oxadiazin-2-one 3-(4-pyrazinecarbonylaminobenzyl)-5-(3-methoxy-4-fluoromethoxyphenyl)-6-ethyl-3,6-dihydro-1,3,4-oxadiazin-2-one 3-(4-pyrazinecarbonylaminobenzyl)-5-(3-difluoromethoxy-4-methoxyphenyl)-6-ethyl-3,6-dihydro-1,3,4-oxadiazin-2-one 3-(4-pyrazinecarbonylaminobenzyl)-5-(3-trifluoromethoxy-4-methoxyphenyl)-6-ethyl-3,6-dihydro-1,3,4-oxadiazin-2-one 3-(4-pyrazinecarbonylaminobenzyl)-5-(3-fluoromethoxy-4-methoxyphenyl)-6-ethyl-3,6-dihydro-1,3,4-oxadiazin-2-one 3-(4-pyrazinecarbonylaminobenzyl)-5-(3-methoxy-4-ethoxyphenyl)-6-ethyl-3,6-dihydro-1,3,4-oxadiazin-2-one 3-(4-pyrazinecarbonylaminobenzyl)-5-(3-ethoxy-4-methoxyphenyl)-6-ethyl-3,6-dihydro-1,3,4-oxadiazin-2-one 3-(4-pyrazinecarbonylaminobenzyl)-5-(3-hydroxy-4-methoxyphenyl)-6-ethyl-3,6-dihydro-1,3,4-oxadiazin-2-one 3-(4-pyrazinecarbonylaminobenzyl)-5-(4-methylsulfonylphenyl)-6-ethyl-3,6-dihydro-1,3,4-oxadiazin-2-one 3-(4-pyrazinecarbonylaminobenzyl)-5-(4-methyleneoxyphenyl)-6-ethyl-3,6-dihydro-1,3,4-oxadiazin-2-one 3-(4-pyrazinecarbonylaminobenzyl)-5-(3-cyclopentyloxy-4-methoxyphenyl)-6-ethyl-3,6-dihydro-1,3,4-oxadiazin-2-one 3-(3-pyrazinecarbonylaminobenzyl)-5-(3-cyclopentyloxy-4-methoxyphenyl)-6-ethyl-3,6-dihydro-1,3,4-oxadiazin-2-one 3-(4-pyrazinecarbonylaminophenethyl)-5-(3,4-dimethoxyphenyl)-3,6-dihydro-1,3,4-oxadiazin-2-one 3-(4-pyrazinecarbonylaminophenethyl)-5-(3,4-dimethoxyphenyl)-6-ethyl-3,6-dihydro-1,3,4-oxadiazin-2-one.

Analogously, by reaction of the abovementioned "amine derivatives" with 6-chloropyridazine-3-carbonyl chloride, the compounds below are obtained 2-(4-(6-chloropyridazine-3-carbonylamino)benzyl)-6-(3,4-dimethoxyphenyl)-2,3,4,5-tetrahydropyridazin-3-one 2-(3-(6-chloropyridazine-3-carbonylamino)benzyl)-6-(3,4-dimethoxyphenyl)-2,3,4,5-tetrahydropyridazin-3-one 2-(2-(6-chloropyridazine-3-carbonylamino)benzyl)-6-(3,4-dimethoxyphenyl)-2,3,4,5-tetrahydropyridazin-3-one 2-(4-(6-chloropyridazine-3-carbonylamino)benzyl)-6-(3,4-dimethoxyphenyl)-5-ethyl-2,3,4,5-tetrahydropyridazin-3-one;

2-(3-(6-chloropyridazine-3-carbonylamino)benzyl)-6-(3,4-dimethoxyphenyl)-5-ethyl-2,3,4,5-tetrahydropyridazin-3-one 2-(2-(6-chloropyridazine-3-carbonylamino)benzyl)-6-(3,4-dimethoxyphenyl)-5-ethyl-2,3,4,5-tetrahydropyridazin-3-one 2-(4-(6-chloropyridazine-3-carbonylamino)benzyl)-6-(3-ethoxy-4-trifluoromethoxyphenyl)-5-ethyl-2,3,4,5-tetrahydropyridazin-3-one 2-(4-(6-chloropyridazine-3-carbonylamino)benzyl)-6-(3-methoxy-4-difluoromethoxyphenyl)-5-ethyl-2,3,4,5-tetrahydropyridazin-3-one 2-(4-(6-chloropyridazine-3-carbonylamino)benzyl)-6-(3-methoxy-4-fluoromethoxyphenyl)-5-ethyl-2,3,4,5-tetrahydropyridazin-3-one 2-(4-(6-chloropyridazine-3-carbonylamino)benzyl)-6-(3-difluoromethoxy-4-methoxyphenyl)-5-ethyl-2,3,4,5-tetrahydropyridazin-3-one 2-(4-(6-chloropyridazine-3-carbonylamino)benzyl)-6-(3-trifluoromethoxy-4-methoxyphenyl)-5-ethyl-2,3,4,5-tetrahydropyridazin-3-one 2-(4-(6-chloropyridazine-3-carbonylamino)benzyl)-6-(3-fluoromethoxy-4-methoxyphenyl)-5-ethyl-2,3,4,5-tetrahydropyridazin-3-one 2-(4-(6-chloropyridazine-3-carbonylamino)benzyl)-6-(3-methoxy-4-ethoxyphenyl)-5-ethyl-2,3,4,5-tetrahydropyridazin-3-one 2-(4-(6-chloropyridazine-3-carbonylamino)benzyl)-6-(3-ethoxy-4-methoxyphenyl)-5-ethyl-2,3,4,5-tetrahydropyridazin-3-one 2-(4-(6-chloropyridazine-3-carbonylamino)benzyl)-6-(3-hydroxy-4-methoxyphenyl)-5-ethyl-2,3,4,5-tetrahydropyridazin-3-one 2-(4-(6-chloropyridazine-3-carbonylamino)benzyl)-6-(4-methylsulfonylphenyl)-5-ethyl-2,3,4,5-tetrahydropyridazin-3-one 2-(4-(6-chloropyridazine-3-carbonylamino)benzyl)-6-(4-methyleneoxyphenyl)-5-ethyl-2,3,4,5-tetrahydropyridazin-3-one 2-(4-(6-chloropyridazine-3-carbonylamino)benzyl)-6-(3-cyclopentyloxy-4-methoxyphenyl)-5-ethyl-2,3,4,5-tetrahydropyridazin-3-one 2-(3-(6-chloropyridazine-3-carbonylamino)benzyl)-6-(3-cyclopentyloxy-4-methoxyphenyl)-5-ethyl-2,3,4,5-tetrahydropyridazin-3-one 2-(4-(6-chloropyridazine-3-carbonylamino)phenethyl)-6-(3,4-dimethoxyphenyl)-2,3,4,5-tetrahydropyridazin-3-one 2-(4-(6-chloropyridazine-3-carbonylamino)phenethyl)-6-(3,4-dimethoxyphenyl)-5-ethyl-2,3,4,5-tetrahydropyridazin-3-one 3-(4-(6-chloropyridazine-3-carbonylamino)benzyl)-5-(3,4-dimethoxyphenyl)-3,6-dihydro-1,3,4-thiadiazin-2-one 3-(3-(6-chloropyridazine-3-carbonylamino)benzyl)-5-(3,4-dimethoxyphenyl)-3,6-dihydro-1,3,4-thiadiazin-2-one 3-(2-(6-chloropyridazine-3-carbonylamino)benzyl)-5-(3,4-dimethoxyphenyl)-3,6-dihydro-1,3,4-thiadiazin-2-one 3-(4-(6-chloropyridazine-3-carbonylamino)benzyl)-5-(3,4-dimethoxyphenyl)-6-ethyl-3,6-dihydro-1,3,4-thiadiazin-2-one 3-(3-(6-chloropyridazine-3-carbonylamino)benzyl)-5-(3,4-dimethoxyphenyl)-6-ethyl-3,6-dihydro-1,3,4-thiadiazin-2-one 3-(2-(6-chloropyridazine-3-carbonylamino)benzyl)-5-(3,4-dimethoxyphenyl)-6-ethyl-3,6-dihydro-1,3,4-thiadiazin-2-one 3-(4-(6-chloropyridazine-3-carbonylamino)benzyl)-5-(3-methoxy-4-trifluoromethoxyphenyl)-6-ethyl-3,6-dihydro-1,3,4-thiadiazin-2-one 3-(4-(6-chloropyridazine-3-carbonylamino)benzyl)-5-(3-methoxy-4-difluoromethoxyphenyl)-6-ethyl-3,6-dihydro-1,3,4-thiadiazin-2-one 3-(4-(6-chloropyridazine-3-carbonylamino)benzyl)-5-(3-methoxy-4-fluoromethoxyphenyl)-6-ethyl-3,6-dihydro-1,3,4-thiadiazin-2-one 3-(4-(6-chloropyridazine-3-carbonylamino)benzyl)-5-(3-difluoromethoxy-4-methoxyphenyl)-6-ethyl-3,6-dihydro-1,3,4-thiadiazin-2-one 3-(4-(6-chloropyridazine-3-carbonylamino)benzyl)-5-(3-trifluoromethoxy-4-methoxyphenyl)-6-ethyl-3,6-dihydro-1,3,4-thiadiazin-2-one 3-(4-(6-chloropyridazine-3-carbonylamino)benzyl)-5-(3-fluoromethoxy-4-methoxyphenyl)-6-ethyl-3,6-dihydro-1,3,4-thiadiazin-2-one
3-(4-(6-chloropyridazine-3-carbonylamino)benzyl)-5-(3-methoxy-4-ethoxyphenyl)-6-ethyl-3,6-dihydro-1,3,4-thiadiazin-2-one
3-(4-(6-chloropyridazine-3-carbonylamino)benzyl)-5-(3-ethoxy-4-methoxyphenyl)-6-ethyl-3,6-dihydro-1,3,4-thiadiazin-2-one
3-(4-(6-chloropyridazine-3-carbonylamino)benzyl)-5-(3-hydroxy-4-methoxyphenyl)-6-ethyl-3,6-dihydro-1,3,4-thiadiazin-2-one
3-(4-(6-chloropyridazine-3-carbonylamino)benzyl)-5-(4-methylsulfonylphenyl)-6-ethyl-3,6-dihydro-1,3,4-thiadiazin-2-one
3-(4-(6-chloropyridazine-3-carbonylamino)benzyl)-5-(4-methyleneoxyphenyl)-6-ethyl-3,6-dihydro-1,3,4-thiadiazin-2-one
3-(4-(6-chloropyridazine-3-carbonylamino)benzyl)-5-(3-cyclopentyloxy-4-methoxyphenyl)-6-ethyl-3,6-dihydro-1,3,4-thiadiazin-2-one
3-(3-(6-chloropyridazine-3-carbonylamino)benzyl)-5-(3-cyclopentyloxy-4-methoxyphenyl)-6-ethyl-3,6-dihydro-1,3,4-thiadiazin-2-one
3-(4-(6-chloropyridazine-3-carbonylamino)phenethyl)-5-(3,4-dimethoxyphenyl)-3,6-dihydro-1,3,4-thiadiazin-2-one
3-(4-(6-chloropyridazine-3-carbonylamino)phenethyl)-5-(3,4-dimethoxyphenyl)-6-ethyl-3,6-dihydro-1,3,4-thiadiazin-2-one
3-(4-(6-chloropyridazine-3-carbonylamino)benzyl)-5-(3,4-dimethoxyphenyl)-3,6-dihydro-1,3,4-oxadiazin-2-one
3-(3-(6-chloropyridazine-3-carbonylamino)benzyl)-5-(3,4-dimethoxyphenyl)-3,6-dihydro-1,3,4-oxadiazin-2-one
3-(2-(6-chloropyridazine-3-carbonylamino)benzyl)-5-(3,4-dimethoxyphenyl)-3,6-dihydro-1,3,4-oxadiazin-2-one
3-(4-(6-chloropyridazine-3-carbonylamino)benzyl)-5-(3,4-dimethoxyphenyl)-6-ethyl-3,6-dihydro-1,3,4-oxadiazin-2-one
3-(3-(6-chloropyridazine-3-carbonylamino)benzyl)-5-(3,4-dimethoxyphenyl)-6-ethyl-3,6-dihydro-1,3,4-oxadiazin-2-one
3-(2-(6-chloropyridazine-3-carbonylamino)benzyl)-5-(3,4-dimethoxyphenyl)-6-ethyl-3,6-dihydro-1,3,4-oxadiazin-2-one
3-(4-(6-chloropyridazine-3-carbonylamino)benzyl)-5-(3-methoxy-4-trifluoromethoxyphenyl)-6-ethyl-3,6-dihydro-1,3,4-oxadiazin-2-one
3-(4-(6-chloropyridazine-3-carbonylamino)benzyl)-5-(3-methoxy-4-difluoromethoxyphenyl)-6-ethyl-3,6-dihydro-1,3,4-oxadiazin-2-one
3-(4-(6-chloropyridazine-3-carbonylamino)benzyl)-5-(3-methoxy-4-fluoromethoxyphenyl)-6-ethyl-3,6-dihydro-1,3,4-oxadiazin-2-one
3-(4-(6-chloropyridazine-3-carbonylamino)benzyl)-5-(3-difluoromethoxy-4-methoxyphenyl)-6-ethyl-3,6-dihydro-1,3,4-oxadiazin-2-one
3-(4-(6-chloropyridazine-3-carbonylamino)benzyl)-5-(3-trifluoromethoxy-4-methoxyphenyl)-6-ethyl-3,6-dihydro-1,3,4-oxadiazin-2-one
3-(4-(6-chloropyridazine-3-carbonylamino)benzyl)-5-(3-fluoromethoxy-4-methoxyphenyl)-6-ethyl-3,6-dihydro-1,3,4-oxadiazin-2-one
3-(4-(6-chloropyridazine-3-carbonylamino)benzyl)-5-(3-methoxy-4-ethoxyphenyl)-6-ethyl-3,6-dihydro-1,3,4-oxadiazin-2-one
3-(4-(6-chloropyridazine-3-carbonylamino)benzyl)-5-(3-ethoxy-4-methoxyphenyl)-6-ethyl-3,6-dihydro-1,3,4-oxadiazin-2-one
3-(4-(6-chloropyridazine-3-carbonylamino)benzyl)-5-(3-hydroxy-4-methoxyphenyl)-6-ethyl-3,6-dihydro-1,3,4-oxadiazin-2-one
3-(4-(6-chloropyridazine-3-carbonylamino)benzyl)-5-(4-methylsulfonylphenyl)-6-ethyl-3,6-dihydro-1,3,4-oxadiazin-2-one
3-(4-(6-chloropyridazine-3-carbonylamino)benzyl)-5-(4-methyleneoxyphenyl)-6-ethyl-3,6-dihydro-1,3,4-oxadiazin-2-one
3-(4-(6-chloropyridazine-3-carbonylamino)benzyl)-5-(3-cyclopentyloxy-4-methoxyphenyl)-6-ethyl-3,6-dihydro-1,3,4-oxadiazin-2-one
3-(3-(6-chloropyridazine-3-carbonylamino)benzyl)-5-(3-cyclopentyloxy-4-methoxyphenyl)-6-ethyl-3,6-dihydro-1,3,4-oxadiazin-2-one
3-(4-(6-chloropyridazine-3-carbonylamino)phenethyl)-5-(3,4-dimethoxyphenyl)-3,6-dihydro-1,3,4-oxadiazin-2-one
3-(4-(6-chloropyridazine-3-carbonylamino)phenethyl)-5-(3,4-dimethoxyphenyl)-6-ethyl-3,6-dihydro-1,3,4-oxadiazin-2-one.

Analogously, by reaction of the abovementioned "amine derivatives" with imidazole-4-carbonyl chloride, the compounds below are obtained 2-(4-(imidazole-4-carbonylamino)benzyl)-6-(3,4-dimethoxyphenyl)-2,3,4,5-tetrahydropyridazin-3-one
2-(3-(imidazole-4-carbonylamino)benzyl)-6-(3,4-dimethoxyphenyl)-2,3,4,5-tetrahydropyridazin-3-one
2-(2-(imidazole-4-carbonylamino)benzyl)-6-(3,4-dimethoxyphenyl)-2,3,4,5-tetrahydropyridazin-3-one
2-(4-(imidazole-4-carbonylamino)benzyl)-6-(3,4-dimethoxyphenyl)-5-ethyl-2,3,4,5-tetrahydropyridazin-3-one;
2-(3-(imidazole-4-carbonylamino)benzyl)-6-(3,4-dimethoxyphenyl)-5-ethyl-2,3,4,5-tetrahydropyridazin-3-one
2-(2-(imidazole-4-carbonylamino)benzyl)-6-(3,4-dimethoxyphenyl)-5-ethyl-2,3,4,5-tetrahydropyridazin-3-one
2-(4-(imidazole-4-carbonylamino)benzyl)-6-(3-methoxy-4-trifluoromethoxyphenyl)-5-ethyl-2,3,4,5-tetrahydropyridazin-3-one
2-(4-(imidazole-4-carbonylamino)benzyl)-6-(3-methoxy-4-difluoromethoxyphenyl)-5-ethyl-2,3,4,5-tetrahydropyridazin-3-one
2-(4-(imidazole-4-carbonylamino)benzyl)-6-(3-methoxy-4-fluoromethoxyphenyl)-5-ethyl-2,3,4,5-tetrahydropyridazin-3-one
2-(4-(imidazole-4-carbonylamino)benzyl)-6-(3-difluoromethoxy-4-methoxyphenyl)-5-ethyl-2,3,4,5-tetrahydropyridazin-3-one
2-(4-(imidazole-4-carbonylamino)benzyl)-6-(3-trifluoromethoxy-4-methoxyphenyl)-5-ethyl-2,3,4,5-tetrahydropyridazin-3-one
2-(4-(imidazole-4-carbonylamino)benzyl)-6-(3-fluoromethoxy-4-methoxyphenyl)-5-ethyl-2,3,4,5-tetrahydropyridazin-3-one
2-(4-(imidazole-4-carbonylamino)benzyl)-6-(3-methoxy-4-ethoxyphenyl)-5-ethyl-2,3,4,5-tetrahydropyridazin-3-one
2-(4-(imidazole-4-carbonylamino)benzyl)-6-(3-ethoxy-4-methoxyphenyl)-5-ethyl-2,3,4,5-tetrahydropyridazin-3-one
2-(4-(imidazole-4-carbonylamino)benzyl)-6-(3-hydroxy-4-methoxyphenyl)-5-ethyl-2,3,4,5-tetrahydropyridazin-3-one
2-(4-(imidazole-4-carbonylamino)benzyl)-6-(4-methysulfonylphenyl)-5-ethyl-2,3,4,5-tetrahydropyridazin-3-one 2-(4-(imidazole-4-carbonylamino)benzyl)-6-(4-methyleneoxyphenyl)-5-ethyl-2,3,4,5-tetrahydropyridazin-3-one 2-(4-(imidazole-4-carbonylamino)benzyl)-6-(3-cyclopentyloxy-4-methoxyphenyl)-5-ethyl-2,3,4,5-tetrahydropyridazin-3-one 2-(3-(imidazole-4-carbonylamino)benzyl)-6-(3-cyclopentyloxy-4-methoxyphenyl)-5-ethyl-2,3,4,5-tetrahydropyridazin-3-one 2-(4-(imidazole-4-carbonylamino)phenethyl)-6-(3,4-dimethoxyphenyl)-2,3,4,5-tetrahydropyridazin-3-one 2-(4-(imidazole-4-carbonylamino)phenethyl)-6-(3,4-dimethoxyphenyl)-5-ethyl-2,3,4,5-tetrahydropyridazin-3-one 3-(4-(imidazole-4-carbonylamino)benzyl)-5-(3,4-dimethoxyphenyl)-3,6-dihydro-1,3,4-thiadiazin-2-one 3-(3-(imidazole-4-carbonylamino)benzyl)-5-(3,4-dimethoxyphenyl)-3,6-dihydro-1,3,4-thiadiazin-2-one 3-(2-(imidazole-4-carbonylamino)benzyl)-5-(3,4-dimethoxyphenyl)-3,6-dihydro-1,3,4-thiadiazin-2-one 3-(4-(imidazole-4-carbonylamino)benzyl)-5-(3,4-dimethoxyphenyl)-6-ethyl-3,6-dihydro-1,3,4-thiadiazin-2-one 3-(3-(imidazole-4-carbonylamino)benzyl)-5-(3,4-dimethoxyphenyl)-6-ethyl-3,6-dihydro-1,3,4-thiadiazin-2-one 3-(2-(imidazole-4-carbonylamino)benzyl)-5-(3,4-dimethoxyphenyl)-6-ethyl-3,6-dihydro-1,3,4-thiadiazin-2-one 3-(4-(imidazole-4-carbonylamino)benzyl)-5-(3-methoxy-4-trifluoromethoxyphenyl)-6-ethyl-3,6-dihydro-1,3,4-thiadiazin-2-one 3-(4-(imidazole-4-carbonylamino)benzyl)-5-(3-methoxy-4-difluoromethoxyphenyl)-6-ethyl-3,6-dihydro-1,3,4-thiadiazin-2-one 3-(4-(imidazole-4-carbonylamino)benzyl)-5-(3-methoxy-4-fluoromethoxyphenyl)-6-ethyl-3,6-dihydro-1,3,4-thiadiazin-2-one 3-(4-(imidazole-4-carbonylamino)benzyl)-5-(3-difluoromethoxy-4-methoxyphenyl)-6-ethyl-3,6-dihydro-1,3,4-thiadiazin-2-one 3-(4-(imidazole-4-carbonylamino)benzyl)-5-(3-trifluoromethoxy-4-methoxyphenyl)-6-ethyl-3,6-dihydro-1,3,4-thiadiazin-2-one 3-(4-(imidazole-4-carbonylamino)benzyl-5-(3-fluoromethoxy-4-methoxyphenyl)-6-ethyl-3,6-dihydro-1,3,4-thiadiazin-2-one 3-(4-(imidazole-4-carbonylamino)benzyl)-5-(3-methoxy-4-ethoxyphenyl)-6-ethyl-3,6-dihydro-1,3,4-thiadiazin-2-one 3-(4-(imidazole-4-carbonylamino)benzyl)-5-(3-ethoxy-4-methoxyphenyl)-6-ethyl-3,6-dihydro-1,3,4-thiadiazin-2-one 3-(4-(imidazole-4-carbonylamino)benzyl)-5-(3-hydroxy-4-methoxyphenyl)-6-ethyl-3,6-dihydro-1,3,4-thiadiazin-2-one 3-(4-(imidazole-4-carbonylamino)benzyl)-5-(4-methylsulfonylphenyl)-6-ethyl-3,6-dihydro-1,3,4-thiadiazin-2-one 3-(4-(imidazole-4-carbonylamino)benzyl)-5-(4-methyleneoxyphenyl)-6-ethyl-3,6-dihydro-1,3,4-thiadiazin-2-one 3-(4-(imidazole-4-carbonylamino)benzyl)-5-(3-cyclopentyloxy-4-methoxyphenyl)-6-ethyl-3,6-dihydro-1,3,4-thiadiazin-2-one 3-(3-(imidazole-4-carbonylamino)benzyl)-5-(3-cyclopentyloxy-4-methoxyphenyl)-6-ethyl-3,6-dihydro-1,3,4-thiadiazin-2-one 3-(4-(imidazole-4-carbonylamino)phenethyl)-5-(3,4-dimethoxyphenyl)-3,6-dihydro-1,3,4-oxadiazin-2-one 3-(4-(imidazole-4-carbonylamino)phenethyl)-5-(3,4-dimethoxyphenyl)-6-ethyl-3,6-dihydro-1,3,4-oxadiazin-2-one 3-(4-(imidazole-4-carbonylamino)benzyl)-5-(3,4-dimethoxyphenyl)-3,6-dihydro-1,3,4-oxadiazin-2-one 3-(3-(imidazole-4-carbonylamino)benzyl)-5-(3,4-dimethoxyphenyl)-3,6-dihydro-1,3,4-oxadiazin-2-one 3-(2-(imidazole-4-carbonylamino)benzyl)-5-(3,4-dimethoxyphenyl)-3,6-dihydro-1,3,4-oxadiazin-2-one 3-(4-(imidazole-4-carbonylamino)benzyl)-5-(3,4-dimethoxyphenyl)-6-ethyl-3,6-dihydro-1,3,4-oxadiazin-2-one 3-(3-(imidazole-4-carbonylamino)benzyl)-5-(3,4-dimethoxyphenyl)-6-ethyl-3,6-dihydro-1,3,4-oxadiazin-2-one 3-(2-(imidazole-4-carbonylamino)benzyl)-5-(3,4-dimethoxyphenyl)-6-ethyl-3,6-dihydro-1,3,4-oxadiazin-2-one 3-(4-(imidazole-4-carbonylamino)benzyl)-5-(3-methoxy-4-trifluoromethoxyphenyl)-6-ethyl-3,6-dihydro-1,3,4-oxadiazin-2-one 3-(4-(imidazole-4-carbonylamino)benzyl)-5-(3-methoxy-4-difluoromethoxyphenyl)-6-ethyl-3,6-dihydro-1,3,4-oxadiazin-2-one 3-(4-(imidazole-4-carbonylamino)benzyl)-5-(3-methoxy-4-fluoromethoxyphenyl)-6-ethyl-3,6-dihydro-1,3,4-oxadiazin-2-one 3-(4-(imidazole-4-carbonylamino)benzyl)-5-(3-difluoromethoxy-4-methoxyphenyl)-6-ethyl-3,6-dihydro-1,3,4-oxadiazin-2-one 3-(4-(imidazole-4-carbonylamino)benzyl)-5-(3-trifluoromethoxy-4-methoxyphenyl)-6-ethyl-3,6-dihydro-1,3,4-oxadiazin-2-one 3-(4-(imidazole-4-carbonylamino)benzyl)-5-(3-fluoromethoxy-4-methoxyphenyl)-6-ethyl-3,6-dihydro-1,3,4-oxadiazin-2-one 3-(4-(imidazole-4-carbonylamino)benzyl)-5-(3-methoxy-4-ethoxyphenyl)-6-ethyl-3,6-dihydro-1,3,4-oxadiazin-2-one 3-(4-(imidazole-4-carbonylamino)benzyl)-5-(3-ethoxy-4-methoxyphenyl)-6-ethyl-3,6-dihydro-1,3,4-oxadiazin-2-one 3-(4-(imidazole-4-carbonylamino)benzyl)-5-(3-hydroxy-4-methoxyphenyl)-6-ethyl-3,6-dihydro-1,3,4-oxadiazin-2-one 3-(4-(imidazole-4-carbonylamino)benzyl)-5-(4-methylsulfonylphenyl)-6-ethyl-3,6-dihydro-1,3,4-oxadiazin-2-one 3-(4-(imidazole-4-carbonylamino)benzyl)-5-(4-methyleneoxyphenyl)-6-ethyl-3,6-dihydro-1,3,4-oxadiazin-2-one 3-(4-(imidazole-4-carbonylamino)benzyl)-5-(3-cyclopentyloxy-4-methoxyphenyl)-6-ethyl-3,6-dihydro-1,3,4-oxadiazin-2-one 3-(3-(imidazole-4-carbonylamino)benzyl)-5-(3-cyclopentyloxy-4-methoxyphenyl)-6-ethyl-3,6-dihydro-1,3,4-oxadiazin-2-one 3-(4-(imidazole-4-carbonylamino)phenethy)-5-(3,4-dimethoxyphenyl)-3,6-dihydro-1,3,4-oxadiazin-2-one 3-(4-(imidazole-4-carbonylamino)phenethyl-5-(3,4-dimethoxyphenyl)-6-ethyl-3,6-dihydro-1,3,4-oxadiazin-2-one.

Analogously, by reaction of the abovementioned "amine derivatives" with 2,4-dimethylthiazole-5-carbonyl chloride, the compounds below are obtained 2-(4-(2,4-dimethylthiazole-5-carbonylamino)benzyl)-6-(3,4-dimethoxyphenyl)-2,3,4,5-tetrahydropyridazin-3-one 2-(3-(2,4-dimethylthiazole-5-carbonylamino)benzyl)-6-(3,4-dimethoxyphenyl)-2,3,4,5-tetrahydropyridazin-3-one 2-(2-(2,4-dimethylthiazole-5-carbonylamino)benzyl)-6-(3,4-dimethoxyphenyl)-2,3,4,5-tetrahydropyridazin-3-one 2-(4-(2,4-dimethylthiazole-5-carbonylamino)benzyl)-6-(3,4-dimethoxyphenyl)-5-ethyl-2,3,4,5-tetrahydropyridazin-3-one;

2-(3-(2,4-dimethylthiazole-5-carbonylamino)benzyl)-6-(3,4-dimethoxyphenyl)-5-ethyl-2,3,4,5-tetrahydropyridazin-3-one 2-(2-(2,4-dimethylthiazole-5-carbonylamino)benzyl)-6-(3,4-dimethoxyphenyl)-5-ethyl-2,3,4,5-tetrahydropyridazin-3-one 2-(4-(2,4-dimethylthiazole-5-carbonylamino)benzyl)-6-(3-methoxy-4-trifluoromethoxyphenyl)-5-ethyl-2,3,4,5-tetrahydropyridazin-3-one 2-(4-(2,4-dimethylthiazole-5-carbonylamino)benzyl)-6-(3-methoxy-4-difluoromethoxyphenyl)-5-ethyl-2,3,4,5-tetrahydropyridazin-3-one 2-(4-(2,4-dimethylthiazole-5-carbonylamino)benzyl)-6-(3-methoxy-4-fluoromethoxyphenyl)-5-ethyl-2,3,4,5-tetrahydropyridazin-3-one 2-(4-(2,4-dimethylthiazole-5-carbonylamino)benzyl)-6-(3-difluoromethoxy-4-methoxyphenyl)-5-ethyl-2,3,4,5-tetrahydropyridazin-3-one 2-(4-(2,4-dimethylthiazole-5-carbonylamino)benzyl)-6-(3-trifluoromethoxy-4-methoxyphenyl)-5-ethyl-2,3,4,5-tetrahydropyridazin-3-one 2-(4-(2,4-dimethylthiazole-5-carbonylamino)benzyl)-6-(3-fluoromethoxy-4-methoxyphenyl)-5-ethyl-2,3,4,5-tetrahydropyridazin-3-one 2-(4-(2,4-dimethylthiazole-5-carbonylamino)benzyl)-6-(3-methoxy-4-ethoxyphenyl)-5-ethyl-2,3,4,5-tetrahydropyridazin-3-one 2-(4-(2,4-dimethylthiazole-5-carbonylamino)benzyl)-6-(3-ethoxy-4-methoxyphenyl)-5-ethyl-2,3,4,5-tetrahydropyridazin-3-one 2-(4-(2,4-dimethylthiazole-5-carbonylamino)benzyl)-6-(3-hydroxy-4-methoxyphenyl)-5-ethyl-2,3,4,5-tetrahydropyridazin-3-one 2-(4-(2,4-dimethylthiazole-5-carbonylamino)benzyl)-6-(4-methylsulfonylphenyl)-5-ethyl-2,3,4,5-tetrahydropyridazin-3-one 2-(4-(2,4-dimethylthiazole-5-carbonylamino)benzyl)-6-(4-methyleneoxyphenyl)-5-ethyl-2,3,4,5-tetrahydropyridazin-3-one 2-(4-(2,4-dimethylthiazole-5-carbonylamino)benzyl)-6-(3-cyclopentyloxy-4-methoxyphenyl)-5-ethyl-2,3,4,5-tetrahydropyridazin-3-one 2-(3-(2,4-dimethylthiazole-5-carbonylamino)benzyl)-6-(3-cyclopentyloxy-4-methoxyphenyl)-5-ethyl-2,3,4,5-tetrahydropyridazin-3-one 2-(4-(2,4-dimethylthiazole-5-carbonylamino)phenethyl)-6-(3,4-dimethoxyphenyl)-2,3,4,5-tetrahydropyridazin-3-one 2-(4-(2,4-dimethylthiazole-5-carbonylamino)phenethyl)-6-(3,4-dimethoxyphenyl)-5-ethyl-2,3,4,5-tetrahydropyridazin-3-one 3-(4-(2,4-dimethylthiazole-5-carbonylamino)benzyl)-5-(3,4-dimethoxyphenyl)-3,6-dihydro-1,3,4-thiadiazin-2-one 3-(3-(2,4-dimethylthiazole-5-carbonylamino)benzyl)-5-(3,4-dimethoxyphenyl)-3,6-dihydro-1,3,4-thiadiazin-2-one 3-(2-(2,4-dimethylthiazole-5-carbonylamino)benzyl)-5-(3,4-dimethoxyphenyl)-3,6-dihydro-1,3,4-thiadiazin-2-one 3-(4-(2,4-dimethylthiazole-5-carbonylamino)benzyl)-5-(3,4-dimethoxyphenyl)-6-ethyl-3,6-dihydro-1,3,4-thiadiazin-2-one 3-(3-(2,4-dimethylthiazole-5-carbonylamino)benzyl)-5-(3,4-dimethoxyphenyl)-6-ethyl-3,6-dihydro-1,3,4-thiadiazin-2-one 3-(2-(2,4-dimethylthiazole-5-carbonylamino)benzyl)-5-(3,4-dimethoxyphenyl)-6-ethyl-3,6-dihydro-1,3,4-thiadiazin-2-one 3-(4-(2,4-dimethylthiazole-5-carbonylamino)benzyl)-5-(3-methoxy-4-trifluoromethoxyphenyl)-6-ethyl-3,6-dihydro-1,3,4-thiadiazin-2-one 3-(4-(2,4-dimethylthiazole-5-carbonylamino)benzyl)-5-(3-methoxy-4-difluoromethoxyphenyl)-6-ethyl-3,6-dihydro-1,3,4-thiadiazin-2-one 3-(4-(2,4-dimethylthiazole-5-carbonylamino)benzyl)-5-(3-methoxy-4-fluoromethoxyphenyl)-6-ethyl-3,6-dihydro-1,3,4-thiadiazin-2-one 3-(4-(2,4-dimethylthiazole-5-carbonylamino)benzyl)-5-(3-difluoromethoxy-4-methoxyphenyl)-6-ethyl-3,6-dihydro-1,3,4-thiadiazin-2-one 3-(4-(2,4-dimethylthiazole-5-carbonylamino)benzyl)-5-(3-trifluoromethoxy-4-methoxyphenyl)-6-ethyl-3,6-dihydro-1,3,4-thiadiazin-2-one 3-(4-(2,4-dimethylthiazole-5-carbonylamino)benzyl)-5-(3-fluoromethoxy-4-methoxyphenyl)-6-ethyl-3,6-dihydro-1,3,4-thiadiazin-2-one 3-(4-(2,4-dimethylthiazole-5-carbonylamino)benzyl)-5-(3-methoxy-4-ethoxyphenyl)-6-ethyl-3,6-dihydro-1,3,4-thiadiazin-2-one 3-(4-(2,4-dimethylthiazole-5-carbonylamino)benzyl)-5-(3-ethoxy-4-methoxyphenyl)-6-ethyl-3,6-dihydro-1,3,4-thiadiazin-2-one 3-(4-(2,4-dimethylthiazole-5-carbonylamino)benzyl)-5-(3-hydroxy-4-methoxyphenyl)-6-ethyl-3,6-dihydro-1,3,4-thiadiazin-2-one 3-(4-(2,4-dimethylthiazole-5-carbonylamino)benzyl)-5-(4-methylsulfonylphenyl)-6-ethyl-3,6-dihydro-1,3,4-thiadiazin-2-one 3-(4-(2,4-dimethylthiazole-5-carbonylamino)benzyl)-5-(4-methyleneoxyphenyl)-6-ethyl-3,6-dihydro-1,3,4-thiadiazin-2-one 3-(4-(2,4-dimethylthiazole-5-carbonylamino)benzyl)-5-(3-cyclopentyloxy-4-methoxyphenyl)-6-ethyl-3,6-dihydro-1,3,4-thiadiazin-2-one 3-(4-(2,4-dimethylthiazole-5-carbonylamino)phenethyl)-5-(3,4-dimethoxyphenyl)-3,6-dihydro-1,3,4-thiadiazin-2-one 3-(4-(2,4-dimethylthiazole-5-carbonylamino)phenethyl)-5-(3,4-dimethoxyphenyl)-6-ethyl-3,6-dihydro-1,3,4-thiadiazin-2-one 3-(4-(2,4-dimethylthiazole-5-carbonylamino)benzyl)-5-(3,4-dimethoxyphenyl)-3,6-dihydro-1,3,4-oxadiazin-2-one 3-(3-(imidazole-4-carbonylamino)benzyl)-5-(3,4-dimethoxyphenyl)-3,6-dihydro-1,3,4-oxadiazin-2-one 3-(2-(2,4-dimethylthiazole-5-carbonylamino)benzyl)-5-(3,4-dimethoxyphenyl)-3,6-dihydro-1,3,4-oxadiazin-2-one 3-(4-(2,4-dimethylthiazole-5-carbonylamino)benzyl)-5-(3,4-dimethoxyphenyl)-6-ethyl-3,6-dihydro-1,3,4-oxadiazin-2-one 3-(3-(2,4-dimethylthiazole-5-carbonylamino)benzyl)-5-(3,4-dimethoxyphenyl)-6-ethyl-3,6-dihydro-1,3,4-oxadiazin-2-one 3-(2-(2,4-dimethylthiazole-5-carbonylamino)benzyl)-5-(3,4-dimethoxyphenyl)-6-ethyl-3,6-dihydro-1,3,4-oxadiazin-2-one 3-(4-(2,4-dimethylthiazole-5-carbonylamino)benzyl)-5-(3-methoxy-4-trifluoromethoxyphenyl)-6-ethyl-3,6-dihydro-1,3,4-oxadiazin-2-one 3-(4-(2,4-dimethylthiazole-5-carbonylamino)benzyl)-5-(3-methoxy-4-difluoromethoxyphenyl)-6-ethyl-3,6-dihydro-1,3,4-oxadiazin-2-one 3-(4-(2,4-dimethylthiazole-5-carbonylamino)benzyl)-5-(3-methoxy-4-fluoromethoxyphenyl)-6-ethyl-3,6-dihydro-1,3,4-oxadiazin-2-one 3-(4-(2,4-dimethylthiazole-5-carbonylamino)benzyl)-5-(3-difluoromethoxy-4-methoxyphenyl)-6-ethyl-3,6-dihydro-1,3,4-oxadiazin-2-one 3-(4-(2,4-dimethylthiazole-5-carbonylamino)benzyl)-5-(3-trifluoromethoxy-4-methoxyphenyl)-6-ethyl-3,6-dihydro-1,3,4-oxadiazin-2-one 3-(4-(2,4-dimethylthiazole-5-carbonylamino)benzyl)-5-(3-fluoromethoxy-4-methoxyphenyl)-6-ethyl-3,6-dihydro-1,3,4-oxadiazin-2-one 3-(4-(2,4-dimethylthiazole-5-carbonylamino)benzyl)-5-(3-methoxy-4-ethoxyphenyl)-6-ethyl-3,6-dihydro-1,3,4-oxadiazin-2-one 3-(4-(2,4-dimethylthiazole-5-carbonylamino)benzyl)-5-(3-ethoxy-4-methoxyphenyl)-6-ethyl-3,6-dihydro-1,3,4-oxadiazin-2-one 3-(4-(2,4-dimethylthiazole-5-carbonylamino)benzyl)-5-(3-hydroxy-4-methoxyphenyl)-6-ethyl-3,6-dihydro-1,3,4-oxadiazin-2-one 3-(4-(2,4-dimethylthiazole-5-carbonylamino)benzyl)-5-(4-methylsulfonylphenyl)-6-ethyl-3,6-dihydro-1,3,4-oxadiazin-2-one 3-(4-(2,4-dimethylthiazole-5-carbonylamino)benzyl)-5-(4-methyleneoxyphenyl)-6-ethyl-3,6-dihydro-1,3,4-oxadiazin-2-one 3-(4-(2,4-dimethylthiazole-5-carbonylamino)benzyl)-5-(3-cyclopentyloxy-4-methoxyphenyl)-6-ethyl-3,6-dihydro-1,3,4-oxadiazin-2-one 3-(3-(2,4-dimethylthiazole-5-carbonylamino)benzyl)-5-(3-cyclopentyloxy-4-methoxyphenyl)-6-ethyl-3,6-dihydro-1,3,4-oxadiazin-2-one 3-(4-(2,4-dimethylthiazole-5-carbonylamino)phenethyl)-5-(3,4-dimethoxyphenyl)-3,6-dihydro-1,3,4-oxadiazin-2-one 3-(4-(2,4-dimethylthiazole-5-carbonylamino)phenethyl)-5-(3,4-dimethoxyphenyl)-6-ethyl-3,6-dihydro-1,3,4-oxadiazin-2-one.

Analogously, by reaction of the abovementioned "amine derivatives" with isoxazole-5-carbonyl chloride, the compounds below are obtained 2-(4-(isoxazole-5-carbonylamino)benzyl)-6-(3,4-dimethoxyphenyl)-2,3,4,5-tetrahydropyridazin-3-one, m.p. 217°

2-(3-(isoxazole-5-carbonylamino)benzyl)-6-(3,4-dimethoxyphenyl)-2,3,4,5-tetrahydropyridazin-3-one 2-(2-(isoxazole-5-carbonylamino)benzyl)-6-(3,4-dimethoxyphenyl)-2,3,4,5-tetrahydropyridazin-3-one 2-(4-(isoxazole-5-carbonylamino)benzyl)-6-(3,4-dimethoxyphenyl)-5-ethyl-2,3,4,5-tetrahydropyridazin-3-one;

2-(3-(isoxazole-5-carbonylamino)benzyl)-6-(3,4-dimethoxyphenyl)-5-ethyl-2,3,4,5-tetrahydropyridazin-3-one 2-(2-(isoxazole-5-carbonylamino)benzyl)-6-(3,4-dimethoxyphenyl)-5-ethyl-2,3,4,5-tetrahydropyridazin-3-one 2-(4-(isoxazole-5-carbonylamino)benzyl)-6-(3-methoxy-4-trifluoromethoxyphenyl)-5-ethyl-2,3,4,5-tetrahydropyridazin-3-one 2-(4-(isoxazole-5-carbonylamino)benzyl)-6-(3-methoxy-4-difluoromethoxyphenyl)-5-ethyl-2,3,4,5-tetrahydropyridazin-3-one 2-(4-(isoxazole-5-carbonylamino)benzyl)-6-(3-methoxy-4-fluoromethoxyphenyl)-5-ethyl-2,3,4,5-tetrahydropyridazin-3-one 2-(4-(isoxazole-5-carbonylamino)benzyl)-6-(3-difluoromethoxy-4-methoxyphenyl)-5-ethyl-2,3,4,5-tetrahydropyridazin-3-one 2-(4-(isoxazole-5-carbonylamino)benzyl)-6-(3-trifluoromethoxy-4-methoxyphenyl)-5-ethyl-2,3,4,5-tetrahydropyridazin-3-one 2-(4-(isoxazole-5-carbonylamino)benzyl)-6-(3-fluoromethoxy-4-methoxyphenyl)-5-ethyl-2,3,4,5-tetrahydropyridazin-3-one 2-(4-(isoxazole-5-carbonylamino)benzyl)-6-(3-methoxy-4-ethoxyphenyl)-5-ethyl-2,3,4,5-tetrahydropyridazin-3-one 2-(4-(isoxazole-5-carbonylamino)benzyl)-6-(3-ethoxy-4-methoxyphenyl)-5-ethyl-2,3,4,5-tetrahydropyridazin-3-one 2-(4-(isoxazole-5-carbonylamino)benzyl)-6-(3-hydroxy-4-methoxyphenyl)-5-ethyl-2,3,4,5-tetrahydropyridazin-3-one 2-(4-(isoxazole-5-carbonylamino)benzyl)-6-(4-methylsulfonylphenyl)-5-ethyl-2,3,4,5-tetrahydropyridazin-3-one 2-(4-(isoxazole-5-carbonylamino)benzyl)-6-(4-methyleneoxyphenyl)-5-ethyl-2,3,4,5-tetrahydropyridazin-3-one 2-(4-(isoxazole-5-carbonylamino)benzyl)-6-(3-cyclopentyloxy-4-methoxyphenyl)-5-ethyl-2,3,4,5-tetrahydropyridazin-3-one 2-(3-(isoxazole-5-carbonylamino)benzyl)-6-(3-cyclopentyloxy-4-methoxyphenyl)-5-ethyl-2,3,4,5-tetrahydropyridazin-3-one 2-(4-(isoxazole-5-carbonylamino)phenethyl)-6-(3,4-dimethoxyphenyl)-2,3,4,5-tetrahydropyridazin-3-one 2-(4-(isoxazole-5-carbonylamino)phenethyl)-6-(3,4-dimethoxyphenyl)-5-ethyl-2,3,4,5-tetrahydropyridazin-3-one 3-(4-(isoxazole-5-carbonylamino)benzyl)-5-(3,4-dimethoxyphenyl)-3,6-dihydro-1,3,4-thiadiazin-2-one, m.p. 196°

3-(3-(isoxazole-5-carbonylamino)benzyl)-5-(3,4-dimethoxyphenyl)-3,6-dihydro-1,3,4-thiadiazin-2-one 3-(2-(isoxazole-5-carbonylamino)benzyl)-5-(3,4-dimethoxyphenyl)-3,6-dihydro-1,3,4-thiadiazin-2-one 3-(4-(isoxazole-5-carbonylamino)benzyl)-5-(3,4-dimethoxyphenyl)-6-ethyl-3,6-dihydro-1,3,4-thiadiazin-2-one 3-(3-(isoxazole-5-carbonylamino)benzyl)-5-(3,4-dimethoxyphenyl)-6-ethyl-3,6-dihydro-1,3,4-thiadiazin-2-one 3-(2-(isoxazole-5-carbonylamino)benzyl)-5-(3,4-dimethoxyphenyl)-6-ethyl-3,6-dihydro-1,3,4-thiadiazin-2-one 3-(4-(isoxazole-5-carbonylamino)benzyl)-5-(3-methoxy-4-trifluoromethoxyphenyl)-6-ethyl-3,6-dihydro-1,3,4-thiadiazin-2-one 3-(4-(isoxazole-5-carbonylamino)benzyl)-5-(3-methoxy-4-difluoromethoxyphenyl)-6-ethyl-3,6-dihydro-1,3,4-thiadiazin-2-one 3-(4-(isoxazole-5-carbonylamino)benzyl)-5-(3-methoxy-4-fluoromethoxyphenyl)-6-ethyl-3,6-dihydro-1,3,4-thiadiazin-2-one 3-(4-(isoxazole-5-carbonylamino)benzyl)-5-(3-difluoromethoxy-4-methoxyphenyl)-6-ethyl-3,6-dihydro-1,3,4-thiadiazin-2-one 3-(4-(isoxazole-5-carbonylamino)benzyl)-5-(3-trifluoromethoxy-4-methoxyphenyl)-6-ethyl-3,6-dihydro-1,3,4-thiadiazin-2-one 3-(4-(isoxazole-5-carbonylamino)benzyl)-5-(3-fluoromethoxy-4-methoxyphenyl)-6-ethyl-3,6-dihydro-1,3,4-thiadiazin-2-one 3-(4-(isoxazole-5-carbonylamino)benzyl)-5-(3-methoxy-4-ethoxyphenyl)-6-ethyl-3,6-dihydro-1,3,4-thiadiazin-2-one 3-(4-(isoxazole-5-carbonylamino)benzyl)-5-(3-ethoxy-4-methoxyphenyl)-6-ethyl-3,6-dihydro-1,3,4-thiadiazin-2-one 3-(4-(isoxazole-5-carbonylamino)benzyl)-5-(3-hydroxy-4-methoxyphenyl)-6-ethyl-3,6-dihydro-1,3,4-thiadiazin-2-one 3-(4-(isoxazole-5-carbonylamino)benzyl)-5-(4-methylsulfonylphenyl)-6-ethyl-3,6-dihydro-1,3,4-thiadiazin-2-one 3-(4-(isoxazole-5-carbonylamino)benzyl)-5-(4-methyleneoxyphenyl)-6-ethyl-3,6-dihydro-1,3,4-thiadiazin-2-one 3-(4-(isoxazole-5-carbonylamino)benzyl)-5-(3-cyclopentyloxy-4-methoxyphenyl)-6-ethyl-3,6-dihydro-1,3,4-thiadiazin-2-one 3-(3-(isoxazole-5-carbonylamino)benzyl)-5-(3-cyclopentyloxy-4-methoxyphenyl)-6-ethyl-3,6-dihydro-1,3,4-thiadiazin-2-one 3-(4-(isoxazole-5-carbonylamino)phenethyl)-5-(3,4-dimethoxyphenyl)-3,6-dihydro-1,3,4-thiadiazin-2-one 3-(4-(isoxazole-5-carbonylamino)phenethyl)-5-(3,4-dimethoxyphenyl)-6-ethyl-3,6-dihydro-1,3,4-thiadiazin-2-one 3-(4-(isoxazole-5-carbonylamino)benzyl)-5-(3,4-dimethoxyphenyl)-3,6-dihydro-1,3,4-oxadiazin-2-one 3-(3-(isoxazole-5-carbonylamino)benzyl)-5-(3,4-dimethoxyphenyl)-3,6-dihydro-1,3,4-oxadiazin-2-one 3-(2-(isoxazole-5-carbonylamino)benzyl)-5-(3,4-dimethoxyphenyl)-3,6-dihydro-1,3,4-oxadiazin-2-one 3-(4-(isoxazole-5-carbonylamino)benzyl)-5-(3,4-dimethoxyphenyl)-6-ethyl-3,6-dihydro-1,3,4-oxadiazin-2-one 3-(3-(isoxazole-5-carbonylamino)benzyl)-5-(3,4-dimethoxyphenyl)-6-ethyl-3,6-dihydro-1,3,4-oxadiazin-2-one 3-(2-(isoxazole-5-carbonylamino)benzyl)-5-(3,4-dimethoxyphenyl)-6-ethyl-3,6-dihydro-1,3,4-oxadiazin-2-one 3-(4-(isoxazole-5-carbonylamino)benzyl)-5-(3-methoxy-4-trifluoromethoxyphenyl)-6-ethyl-3,6-dihydro-1,3,4-oxadiazin-2-one 3-(4-(isoxazole-5-carbonylamino)benzyl)-5-(3-methoxy-4-difluoromethoxyphenyl)-6-ethyl-3,6-dihydro-1,3,4-oxadiazin-2-one 3-(4-(isoxazole-5-carbonylamino)benzyl)-5-(3-methoxy-4-fluoromethoxyphenyl)-6-ethyl-3,6-dihydro-1,3,4-oxadiazin-2-one 3-(4-(isoxazole-5-carbonylamino)benzyl)-5-(3-difluoromethoxy-4-methoxyphenyl)-6-ethyl-3,6-dihydro-1,3,4-oxadiazin-2-one 3-(4-(isoxazole-5-carbonylamino)benzyl)-5-(3-trifluoromethoxy-4-methoxyphenyl)-6-ethyl-3,6-dihydro-1,3,4-oxadiazin-2-one 3-(4-(isoxazole-5-carbonylamino)benzyl)-5-(3-fluoromethoxy-4-methoxyphenyl)-6-ethyl-3,6-dihydro-1,3,4-oxadiazin-2-one 3-(4-(isoxazole-5-carbonylamino)benzyl)-5-(3-methoxy-4-ethoxyphenyl)-6-ethyl-3,6-dihydro-1,3,4-oxadiazin-2-one 3-(4-isoxazole-5-carbonylamino)benzyl)-5-(3-ethoxy-4-methoxyphenyl)-6-ethyl-3,6-dihydro-1,3,4-oxadiazin-2-one 3-(4-isoxazole-5-carbonylamino)benzyl)-5-(3-hydroxy-4-methoxyphenyl)-6-ethyl-3,6-dihydro-1,3,4-oxadiazin-2-one 3-(4-(isoxazole-5-carbonylamino)benzyl)-5-(4-methylsulfonylphenyl)-6-ethyl-3,6-dihydro-1,3,4-oxadiazin-2-one 3-(4-(isoxazole-5-carbonylamino)benzyl)-5-(4-methyleneoxyphenyl)-6-ethyl-3,6-dihydro-1,3,4-oxadiazin-2-one 3-(4-(isoxazole-5-carbonylamino)benzyl)-5-(3-cyclopentyloxy-4-methoxyphenyl)-6-ethyl-3,6-dihydro-1,3,4-oxadiazin-2-one 3-(3-isoxazole-5-carbonylamino)benzyl)-5-(3-cyclopentyloxy-4-methoxyphenyl)-6-ethyl-3,6-dihydro-1,3,4-oxadiazin-2-one 3-(4-isoxazole-5-carbonylamino)phenethy)-5-(3,4-dimethoxyphenyl)-3,6-dihydro-1,3,4-oxadiazin-2-one 3-(4-isoxazole-5-carbonylamino)phenethy)-5-(3,4-dimethoxyphenyl)-6-ethyl-3,6-dihydro-1,3,4-oxadiazin-2-one.

Analogously, by reaction of the abovementioned "amine derivatives" with oxazole-5-carbonyl chloride, the compounds below are obtained 2-(4-(oxazole-5-carbonylamino)benzyl)-6-(3,4-dimethoxyphenyl)-2,3,4,5-tetrahydropyridazin-3-one 2-(3-(oxazole-5-carbonylamino)benzyl)-6-(3,4-dimethoxyphenyl)-2,3,4,5-tetrahydropyridazin-3-one 2-(2-(oxazole-5-carbonylamino)benzyl)-6-(3,4-dimethoxyphenyl)-2,3,4,5-tetrahydropyridazin-3-one 2-(4-(oxazole-5-carbonylamino)benzyl)-6-(3,4-dimethoxyphenyl)-5-ethyl-2,3,4,5-tetrahydropyridazin-3-one;

2-(3-(oxazole-5-carbonylamino)benzyl)-6-(3,4-dimethoxyphenyl)-5-ethyl-2,3,4,5-tetrahydropyridazin-3-one 2-(2-(oxazole-5-carbonylamino)benzyl)-6-(3,4-dimethoxyphenyl)-5-ethyl-2,3,4,5-tetrahydropyridazin-3-one 2-(4-(oxazole-5-carbonylamino)benzyl)-6-(3-methoxy-4-trifluoromethoxyphenyl)-5-ethyl-2,3,4,5-tetrahydropyridazin-3-one 2-(4-(oxazole-5-carbonylamino)benzyl)-6-(3-methoxy-4-difluoromethoxyphenyl)-5-ethyl-2,3,4,5-tetrahydropyridazin-3-one 2-(4-(oxazole-5-carbonylamino)benzyl)-6-(3-methoxy-4-fluromethoxyphenyl)-5-ethyl-2,3,4,5-tetrahydropyridazin-3-one 2-(4-(oxazole-5-carbonylamino)benzyl)-6-(3-difluoromethoxy-4-methoxyphenyl)-5-ethyl-2,3,4,5-tetrahydropyridazin-3-one 2-(4-(oxazole-5-carbonylamino)benzyl)-6-(3-trifluoromethoxy-4-methoxyphenyl)-5-ethyl-2,3,4,5-tetrahydropyridazin-3-one 2-(4-(oxazole-5-carbonylamino)benzyl)-6-(3-fluoromethoxy-4-methoxyphenyl)-5-ethyl-2,3,4,5-tetrahydropyridazin-3-one 2-(4-(oxazole-5-carbonylamino)benzyl)-6-(3-methoxy-4-ethoxyphenyl)-5-ethyl-2,3,4,5-tetrahydropyridazin-3-one 2-(4-(oxazole-5-carbonylamino)benzyl)-6-(3-ethoxy-4-methoxyphenyl)-5-ethyl-2,3,4,5-tetrahydropyridazin-3-one 2-(4-(oxazole-5-carbonylamino)benzyl)-6-(3-hydroxy-4-methoxyphenyl)-5-ethyl-2,3,4,5-tetrahydropyridazin-3-one 2-(4-(oxazole-5-carbonylamino)benzyl)-6-(4-methylsulfonylphenyl)-5-ethyl-2,3,4,5-tetrahydropyridazin-3-one 2-(4-(oxazole-5-carbonylamino)benzyl)-6-(4-methyleneoxyphenyl)-5-ethyl-2,3,4,5-tetrahydropyridazin-3-one
2-(4-(oxazole-5-carbonylamino)benzyl)-6-(3-cyclopentyloxy-4-methoxyphenyl)-5-ethyl-2,3,4,5-tetrahydropyridazin-3-one
2-(3-(oxazole-5-carbonylamino)benzyl)-6-(3-cyclopentyloxy-4-methoxyphenyl)-5-ethyl-2,3,4,5-tetrahydropyridazin-3-one
2-(4-(oxazole-5-carbonylamino)phenethyl)-6-(3,4-dimethoxyphenyl)-2,3,4,5-tetrahydropyridazin-3-one
2-(4-(oxazole-5-carbonylamino)phenethyl)-6-(3,4-dimethoxyphenyl)-5-ethyl-2,3,4,5-tetrahydropyridazin-3-one
3-(4-(oxazole-5-carbonylamino)benzyl)-5-(3,4-dimethoxyphenyl)-3,6-dihydro-1,3,4-thiadiazin-2-one
3-(3-(oxazole-5-carbonylamino)benzyl)-5-(3,4-dimethoxyphenyl)-3,6-dihydro-1,3,4-thiadiazin-2-one
3-(2-(oxazole-5-carbonylamino)benzyl)-5-(3,4-dimethoxyphenyl)-3,6-dihydro-1,3,4-thiadiazin-2-one
3-(4-(oxazole-5-carbonylamino)benzyl)-5-(3,4-dimethoxyphenyl)-6-ethyl-3,6-dihydro-1,3,4-thiadiazin-2-one
3-(3-(oxazole-5-carbonylamino)benzyl)-5-(3,4-dimethoxyphenyl)-6-ethyl-3,6-dihydro-1,3,4-thiadiazin-2-one
3-(2-(oxazole-5-carbonylamino)benzyl)-5-(3,4-dimethoxyphenyl)-6-ethyl-3,6-dihydro-1,3,4-thiadiazin-2-one
3-(4-(oxazole-5-carbonylamino)benzyl)-5-(3-methoxy-4-trifluoromethoxyphenyl)-6-ethyl-3,6-dihydro-1,3,4-thiadiazin-2-one
3-(4-(oxazole-5-carbonylamino)benzyl)-5-(3-methoxy-4-difluoromethoxyphenyl)-6-ethyl-3,6-dihydro-1,3,4-thiadiazin-2-one
3-(4-(oxazole-5-carbonylamino)benzyl)-5-(3-methoxy-4-fluoromethoxyphenyl)-6-ethyl-3,6-dihydro-1,3,4-thiadiazin-2-one
3-(4-(oxazole-5-carbonylamino)benzyl)-5-(3-difluoromethoxy-4-methoxyphenyl)-6-ethyl-3,6-dihydro-1,3,4-thiadiazin-2-one
3-(4-(oxazole-5-carbonylamino)benzyl)-5-(3-trifluoromethoxy-4-methoxyphenyl)-6-ethyl-3,6-dihydro-1,3,4-thiadiazin-2-one
3-(4-(oxazole-5-carbonylamino)benzyl)-5-(3-fluoromethoxy-4-methoxyphenyl)-6-ethyl-3,6-dihydro-1,3,4-thiadiazin-2-one
3-(4-(oxazole-5-carbonylamino)benzyl)-5-(3-methoxy-4-ethoxyphenyl)-6-ethyl-3,6-dihydro-1,3,4-thiadiazin-2-one
3-(4-(oxazole-5-carbonylamino)benzyl)-5-(3-ethoxy-4-methoxyphenyl)-6-ethyl-3,6-dihydro-1,3,4-thiadiazin-2-one
3-(4-(oxazole-5-carbonylamino)benzyl)-5-(3-hydroxy-4-methoxyphenyl)-6-ethyl-3,6-dihydro-1,3,4-thiadiazin-2-one
3-(4-(oxazole-5-carbonylamino)benzyl)-5-(4-methylsulfonylphenyl)-6-ethyl-3,6-dihydro-1,3,4-thiadiazin-2-one
3-(4-(oxazole-5-carbonylamino)benzyl)-5-(4-methyleneoxyphenyl)-6-ethyl-3,6-dihydro-1,3,4-thiadiazin-2-one
3-(4-(oxazole-5-carbonylamino)benzyl)-5-(3-cyclopentyloxy-4-methoxyphenyl)-6-ethyl-3,6-dihydro-1,3,4-thiadiazin-2-one
3-(3-(oxazole-5-carbonylamino)benzyl)-5-(3-cyclopentyloxy-4-methoxyphenyl)-6-ethyl-3,6-dihydro-1,3,4-thiadiazin-2-one
3-(4-(oxazole-5-carbonylamino)phenethyl)-5-(3,4-dimethoxyphenyl)-3,6-dihydro-1,3,4-thiadiazin-2-one
3-(4-(oxazole-5-carbonylamino)phenethyl)-5-(3,4-dimethoxyphenyl)-6-ethyl-3,6-dihydro-1,3,4-thiadiazin-2-one
3-(4-(oxazole-5-carbonylamino)benzyl)-5-(3,4-dimethoxyphenyl)-3,6-dihydro-1,3,4-oxadiazin-2-one
3-(3-(oxazole-5-carbonylamino)benzyl)-5-(3,4-dimethoxyphenyl)-3,6-dihydro-1,3,4-oxadiazin-2-one
3-(2-(oxazole-5-carbonylamino)benzyl)-5-(3,4-dimethoxyphenyl)-3,6-dihydro-1,3,4-oxadiazin-2-one
3-(4-(oxazole-5-carbonylamino)benzyl)-5-(3,4-dimethoxyphenyl)-6-ethyl-3,6-dihydro-1,3,4-oxadiazin-2-one
3-(3-(oxazole-5-carbonylamino)benzyl)-5-(3,4-dimethoxyphenyl)-6-ethyl-3,6-dihydro-1,3,4-oxadiazin-2-one
3-(2-(oxazole-5-carbonylamino)benzyl)-5-(3,4-dimethoxyphenyl)-6-ethyl-3,6-dihydro-1,3,4-oxadiazin-2-one
3-(4-(oxazole-5-carbonylamino)benzyl)-5-(3-methoxy-4-trifluoromethoxyphenyl)-6-ethyl-3,6-dihydro-1,3,4-oxadiazin-2-one
3-(4-(oxazole-5-carbonylamino)benzyl)-5-(3-methoxy-4-difluoromethoxyphenyl)-6-ethyl-3,6-dihydro-1,3,4-oxadiazin-2-one
3-(4-(oxazole-5-carbonylamino)benzyl)-5-(3-methoxy-4-fluoromethoxyphenyl)-6-ethyl-3,6-dihydro-1,3,4-oxadiazin-2-one
3-(4-(oxazole-5-carbonylamino)benzyl)-5-(3-difluoromethoxy-4-methoxyphenyl)-6-ethyl-3,6-dihydro-1,3,4-oxadiazin-2-one
3-(4-(oxazole-5-carbonylamino)benzyl)-5-(3-trifluoromethoxy-4-methoxyphenyl)-6-ethyl-3,6-dihydro-1,3,4-oxadiazin-2-one
3-(4-(oxazole-5-carbonylamino)benzyl)-5-(3-fluoromethoxy-4-methoxyphenyl)-6-ethyl-3,6-dihydro-1,3,4-oxadiazin-2-one
3-(4-(oxazole-5-carbonylamino)benzyl)-5-(3-methoxy-4-ethoxyphenyl)-6-ethyl-3,6-dihydro-1,3,4-oxadiazin-2-one
3-(4-(oxazole-5-carbonylamino)benzyl)-5-(3-ethoxy-4-methoxyphenyl)-6-ethyl-3,6-dihydro-1,3,4-oxadiazin-2-one
3-(4-(oxazole-5-carbonylamino)benzyl)-5-(3-hydroxy-4-methoxyphenyl)-6-ethyl-3,6-dihydro-1,3,4-oxadiazin-2-one
3-(4-(oxazole-5-carbonylamino)benzyl)-5-(4-methylsulfonylphenyl)-6-ethyl-3,6-dihydro-1,3,4-oxadiazin-2-one
3-(4-(oxazole-5-carbonylamino)benzyl)-5-(4-methyleneoxyphenyl)-6-ethyl-3,6-dihydro-1,3,4-oxadiazin-2-one
3-(4-(oxazole-5-carbonylamino)benzyl)-5-(3-cyclopentyloxy-4-methoxyphenyl)-6-ethyl-3,6-dihydro-1,3,4-oxadiazin-2-one
3-(3-(oxazole-5-carbonylamino)benzyl)-5-(3-cyclopentyloxy-4-methoxyphenyl)-6-ethyl-3,6-dihydro-1,3,4-oxadiazin-2-one
3-(4-(oxazole-5-carbonylamino)phenethy)-5-(3,4-dimethoxyphenyl)-3,6-dihydro-1,3,4-oxadiazin-2-one
3-(4-(oxazole-5-carbonylamino)phenethy)-5-(3,4-dimethoxyphenyl)-6-ethyl-3,6-dihydro-1,3,4-oxadiazin-2-one.

Analogously, by reaction of the abovementioned "amine derivatives" with pyrimidine-2-carbonyl chloride, the compounds below are obtained 2-(4-(pyrimidine-2-carbonylamino)benzyl)-6-(3,4-dimethoxyphenyl)-2,3,4,5-tetrahydropyridazin-3-one 2-(3-(pyrimidine-2-carbonylamino)benzyl)-6-(3,4-dimethoxyphenyl)-2,3,4,5-tetrahydropyridazin-3-one 2-(2-(pyrimidine-2-carbonylamino)benzyl)-6-(3,4-dimethoxyphenyl)-2,3,4,5-tetrahydropyridazin-3-one 2-(4-(pyrimidine-2-carbonylamino)benzyl)-6-(3,4-dimethoxyphenyl)-5-ethyl-2,3,4,5-tetrahydropyridazin-3-one;

2-(3-(pyrimidine-2-carbonylamino)benzyl)-6-(3,4-dimethoxyphenyl)-5-ethyl-2,3,4,5-tetrahydropyridazin-3-one 2-(2-(pyrimidine-2-carbonylamino)benzyl)-6-(3,4-dimethoxyphenyl)-5-ethyl-2,3,4,5-tetrahydropyridazin-3-one 2-(4-(pyrimidine-2-carbonylamino)benzyl)-6-(3-methoxy-4-trifluoromethoxyphenyl)-5-ethyl-2,3,4,5-tetrahydropyridazin-3-one 2-(4-(pyrimidine-2-carbonylamino)benzyl)-6-(3-methoxy-4-difluoromethoxyphenyl)-5-ethyl-2,3,4,5-tetrahydropyridazin-3-one 2-(4-(pyrimidine-2-carbonylamino)benzyl)-6-(3-methoxy-4-fluoromethoxyphenyl)-5-ethyl-2,3,4,5-tetrahydropyridazin-3-one 2-(4-(pyrimidine-2-carbonylamino)benzyl)-6-(3-difluoromethoxy-4-methoxyphenyl)-5-ethyl-2,3,4,5-tetrahydropyridazin-3-one 2-(4-(pyrimidine-2-carbonylamino)benzyl)-6-(3-trifluoromethoxy-4-methoxyphenyl)-5-ethyl-2,3,4,5-tetrahydropyridazin-3-one 2-(4-(pyrimidine-2-carbonylamino)benzyl)-6-(3-fluoromethoxy-4-methoxyphenyl)-5-ethyl-2,3,4,5-tetrahydropyridazin-3-one 2-(4-(pyrimidine-2-carbonylamino)benzyl)-6-(3-methoxy-4-ethoxyphenyl)-5-ethyl-2,3,4,5-tetrahydropyridazin-3-one 2-(4-(pyrimidine-2-carbonylamino)benzyl)-6-(3-ethoxy-4-methoxyphenyl)-5-ethyl-2,3,4,5-tetrahydropyridazin-3-one 2-(4-(pyrimidine-2-carbonylamino)benzyl)-6-(3-hydroxy-4-methoxyphenyl)-5-ethyl-2,3,4,5-tetrahydropyridazin-3-one 2-(4-(pyrimidine-2-carbonylamino)benzyl)-6-(4-methylsulfonylphenyl)-5-ethyl-2,3,4,5-tetrahydropyridazin-3-one 2-(4-(pyrimidine-2-carbonylamino)benzyl)-6-(4-methyleneoxyphenyl)-5-ethyl-2,3,4,5-tetrahydropyridazin-3-one 2-(4-(pyrimidine-2-carbonylamino)benzyl)-6-(3-cyclopentyloxy-4-methoxyphenyl)-5-ethyl-2,3,4,5-tetrahydropyridazin-3-one 2-(3-(pyrimidine-2-carbonylamino)benzyl)-6-(3-cyclopentyloxy-4-methoxyphenyl)-5-ethyl-2,3,4,5-tetrahydropyridazin-3-one 2-(4-(pyrimidine-2-carbonylamino)phenethyl)-6-(3,4-dimethoxyphenyl)-2,3,4,5-tetrahydropyridazin-3-one 2-(4-(pyrimidine-2-carbonylamino)phenethyl)-6-(3,4-dimethoxyphenyl)-5-ethyl-2,3,4,5-tetrahydropyridazin-3-one 3-(4-(pyrimidine-2-carbonylamino)benzyl)-5-(3,4-dimethoxyphenyl)-3,6-dihydro-1,3,4-thiadiazin-2-one 3-(3-(pyrimidine-2-carbonylamino)benzyl)-5-(3,4-dimethoxyphenyl)-3,6-dihydro-1,3,4-thiadiazin-2-one 3-(2-(pyrimidine-2-carbonylamino)benzyl)-5-(3,4-dimethoxyphenyl)-3,6-dihydro-1,3,4-thiadiazin-2-one 3-(4-(pyrimidine-2-carbonylamino)benzyl)-5-(3,4-dimethoxyphenyl)-6-ethyl-3,6-dihydro-1,3,4-thiadiazin-2-one 3-(3-(pyrimidine-2-carbonylamino)benzyl)-5-(3,4-dimethoxyphenyl)-6-ethyl-3,6-dihydro-1,3,4-thiadiazin-2-one 3-(2-(pyrimidine-2-carbonylamino)benzyl)-5-(3,4-dimethoxyphenyl)-6-ethyl-3,6-dihydro-1,3,4-thiadiazin-2-one 3-(4-(pyrimidine-2-carbonylamino)benzyl)-5-(3-methoxy-4-trifluoromethoxyphenyl)-6-ethyl-3,6-dihydro-1,3,4-thiadiazin-2-one 3-(4-(pyrimidine-2-carbonylamino)benzyl)-5-(3-methoxy-4-difluoromethoxyphenyl)-6-ethyl-3,6-dihydro-1,3,4-thiadiazin-2-one 3-(4-(pyrimidine-2-carbonylamino)benzyl)-5-(3-methoxy-4-fluoromethoxyphenyl)-6-ethyl-3,6-dihydro-1,3,4-thiadiazin-2-one 3-(4-(pyrimidine-2-carbonylamino)benzyl)-5-(3-difluoromethoxy-4-methoxyphenyl)-6-ethyl-3,6-dihydro-1,3,4-thiadiazin-2-one 3-(4-(pyrimidine-2-carbonylamino)benzyl)-5-(3-trifluoromethoxy-4-methoxyphenyl)-6-ethyl-3,6-dihydro-1,3,4-thiadiazin-2-one 3-(4-(pyrimidine-2-carbonylamino)benzyl)-5-(3-fluoromethoxy-4-methoxyphenyl)-6-ethyl-3,6-dihydro-1,3,4-thiadiazin-2-one 3-(4-(pyrimidine-2-carbonylamino)benzyl)-5-(3-methoxy-4-ethoxyphenyl)-6-ethyl-3,6-dihydro-1,3,4-thiadiazin-2-one 3-(4-(pyrimidine-2-carbonylamino)benzyl)-5-(3-ethoxy-4-methoxyphenyl)-6-ethyl-3,6-dihydro-1,3,4-thiadiazin-2-one 3-(4-(pyrimidine-2-carbonylamino)benzyl)-5-(3-hydroxy-4-methoxyphenyl)-6-ethyl-3,6-dihydro-1,3,4-thiadiazin-2-one 3-(4-(pyrimidine-2-carbonylamino)benzyl)-5-(4-methylsulfonylphenyl)-6-ethyl-3,6-dihydro-1,3,4-thiadiazin-2-one 3-(4-(pyrimidine-2-carbonylamino)benzyl)-5-(4-methyleneoxyphenyl)-6-ethyl-3,6-dihydro-1,3,4-thiadiazin-2-one 3-(4-(pyrimidine-2-carbonylamino)benzyl)-5-(3-cyclopentyloxy-4-methoxyphenyl)-6-ethyl-3,6-dihydro-1,3,4-thiadiazin-2-one 3-(3-(pyrimidine-2-carbonylamino)benzyl)-5-(3-cyclopentyloxy-4-methoxyphenyl)-6-ethyl-3,6-dihydro-1,3,4-thiadiazin-2-one 3-(4-(pyrimidine-2-carbonylamino)phenethyl)-5-(3,4-dimethoxyphenyl)-3,6-dihydro-1,3,4-thiadiazin-2-one 3-(4-(pyrimidine-2-carbonylamino)phenethyl)-5-(3,4-dimethoxyphenyl)-6-ethyl-3,6-dihydro-1,3,4-thiadiazin-2-one 3-(4-(pyrimidine-2-carbonylamino)benzyl)-5-(3,4-dimethoxyphenyl)-3,6-dihydro-1,3,4-oxadiazin-2-one 3-(3-(pyrimidine-2-carbonylamino)benzyl)-5-(3,4-dimethoxyphenyl)-3,6-dihydro-1,3,4-oxadiazin-2-one 3-(2-(pyrimidine-2-carbonylamino)benzyl)-5-(3,4-dimethoxyphenyl)-3,6-dihydro-1,3,4-oxadiazin-2-one 3-(4-(pyrimidine-2-carbonylamino)benzyl)-5-(3,4-dimethoxyphenyl)-6-ethyl-3,6-dihydro-1,3,4-oxadiazin-2-one 3-(3-(pyrimidine-2-carbonylamino)benzyl)-5-(3,4-dimethoxyphenyl)-6-ethyl-3,6-dihydro-1,3,4-oxadiazin-2-one 3-(2-(pyrimidine-2-carbonylamino)benzyl)-5-(3,4-dimethoxyphenyl)-6-ethyl-3,6-dihydro-1,3,4-oxadiazin-2-one 3-(4-(pyrimidine-2-carbonylamino)benzyl)-5-(3-methoxy-4-trifluoromethoxyphenyl)-6-ethyl-3,6-dihydro-1,3,4-oxadiazin-2-one 3-(4-(pyrimidine-2-carbonylamino)benzyl)-5-(3-methoxy-4-difluoromethoxyphenyl)-6-ethyl-3,6-dihydro-1,3,4-oxadiazin-2-one 3-(4-(pyrimidine-2-carbonylamino)benzyl)-5-(3-methoxy-4-fluoromethoxyphenyl)-6-ethyl-3,6-dihydro-1,3,4-oxadiazin-2-one 3-(4-(pyrimidine-2-carbonylamino)benzyl)-5-(3-difluoromethoxy-4-methoxyphenyl)-6-ethyl-3,6-dihydro-1,3,4-oxadiazin-2-one 3-(4-(pyrimidine-2-carbonylamino)benzyl)-5-(3-trifluoromethoxy-4-methoxyphenyl)-6-ethyl-3,6-dihydro-1,3,4-oxadiazin-2-one 3-(4-(pyrimidine-2-carbonylamino)benzyl)-5-(3-fluoromethoxy-4-methoxyphenyl)-6-ethyl-3,6-dihydro-1,3,4-oxadiazin-2-one 3-(4-(pyrimidine-2-carbonylamino)benzyl)-5-(3-methoxy-4-ethoxyphenyl)-6-ethyl-3,6-dihydro-1,3,4-oxadiazin-2-one 3-(4-pyrimidine-2-carbonylamino)benzyl)-5-(3-ethoxy-4-methoxyphenyl)-6-ethyl-3,6-dihydro-1,3,4-oxadiazin-2-one 3-(4-pyrimidine-2-carbonylamino)benzyl)-5-(3-hydroxy-4-methoxyphenyl)-6-ethyl-3,6-dihydro-1,3,4-oxadiazin-2-one 3-(4-pyrimidine-2-carbonylamino)benzyl)-5-(4-methylsulfonylphenyl)-6-ethyl-3,6-dihydro-1,3,4-oxadiazin-2-one 3-(4-pyrimidine-2-carbonylamino)benzyl)-5-(4-methyleneoxyphenyl)-6-ethyl-3,6-dihydro-1,3,4-oxadiazin-2-one 3-(4-pyrimidine-2-carbonylamino)benzyl)-5-(3-cyclopentyloxy-4-methoxyphenyl)-6-ethyl-3,6-dihydro-1,3,4-oxadiazin-2-one 3-(3-pyrimidine-2-carbonylamino)benzyl)-5-(3-cyclopentyloxy-4-methoxyphenyl)-6-ethyl-3,6-dihydro-1,3,4-oxadiazin-2-one 3-(4-pyrimidine-2-carbonylamino)phenethy)-5-(3,4-dimethoxyphenyl)-3,6-dihydro-1,3,4-oxadiazin-2-one 3-(4-pyrimidine-2-carbonylamino)phenethy)-5-(3,4-dimethoxyphenyl)-6-ethyl-3,6-dihydro-1,3,4-oxadiazin-2-one.

Analogously, by reaction of the abovementioned "amine derivatives" with pyrazole-3-carbonyl chloride, the compounds below are obtained 2-(4-(pyrazole-3-carbonylamino)benzyl)-6-(3,4-dimethoxyphenyl)-2,3,4,5-tetrahydropyridazin-3-one 2-(3-(pyrazole-3-carbonylamino)benzyl)-6-(3,4-dimethoxyphenyl)-2,3,4,5-tetrahydropyridazin-3-one 2-(2-(pyrazole-3-carbonylamino)benzyl)-6-(3,4-dimethoxyphenyl)-2,3,4,5-tetrahydropyridazin-3-one 2-(4-(pyrazole-3-carbonylamino)benzyl)-6-(3,4-dimethoxyphenyl)-5-ethyl-2,3,4,5-tetrahydropyridazin-3-one;

2-(3-(pyrazole-3-carbonylamino)benzyl)-6-(3,4-dimethoxyphenyl)-5-ethyl-2,3,4,5-tetrahydropyridazin-3-one 2-(2-(pyrazole-3-carbonylamino)benzyl)-6-(3,4-dimethoxyphenyl)-5-ethyl-2,3,4,5-tetrahydropyridazin-3-one 2-(4-(pyrazole-3-carbonylamino)benzyl)-6-(3-methoxy-4-trifluoromethoxyphenyl)-5-ethyl-2,3,4,5-tetrahydropyridazin-3-one 2-(4-(pyrazole-3-carbonylamino)benzyl)-6-(3-methoxy-4-difluoromethoxyphenyl)-5-ethyl-2,3,4,5-tetrahydropyridazin-3-one 2-(4-(pyrazole-3-carbonylamino)benzyl)-6-(3-methoxy-4-fluoromethoxyphenyl)-5-ethyl-2,3,4,5-tetrahydropyridazin-3-one 2-(4-(pyrazole-3-carbonylamino)benzyl)-6-(3-difluoromethoxy-4-methoxyphenyl)-5-ethyl-2,3,4,5-tetrahydropyridazin-3-one 2-(4-(pyrazole-3-carbonylamino)benzyl)-6-(3-trifluoromethoxy-4-methoxyphenyl)-5-ethyl-2,3,4,5-tetrahydropyridazin-3-one 2-(4-(pyrazole-3-carbonylamino)benzyl)-6-(3-fluoromethoxy-4-methoxyphenyl)-5-ethyl-2,3,4,5-tetrahydropyridazin-3-one 2-(4-(pyrazole-3-carbonylamino)benzyl)-6-(3-methoxy-4-ethoxyphenyl)-5-ethyl-2,3,4,5-tetrahydropyridazin-3-one 2-(4-(pyrazole-3-carbonylamino)benzyl)-6-(3-ethoxy-4-methoxyphenyl)-5-ethyl-2,3,4,5-tetrahydropyridazin-3-one 2-(4-(pyrazole-3-carbonylamino)benzyl)-6-(3-hydroxy-4-methoxyphenyl)-5-ethyl-2,3,4,5-tetrahydropyridazin-3-one 2-(4-(pyrazole-3-carbonylamino)benzyl)-6-(4-methylsulfonylphenyl)-5-ethyl-2,3,4,5-tetrahydropyridazin-3-one 2-(4-(pyrazole-3-carbonylamino)benzyl)-6-(4-methyleneoxyphenyl)-5-ethyl-2,3,4,5-tetrahydropyridazin-3-one 2-(4-(pyrazole-3-carbonylamino)benzyl)-6-(3-cyclopentyloxy-4-methoxyphenyl)-5-ethyl-2,3,4,5-tetrahydropyridazin-3-one 2-(3-(pyrazole-3-carbonylamino)benzyl)-6-(3-cyclopentyloxy-4-methoxyphenyl)-5-ethyl-2,3,4,5-tetrahydropyridazin-3-one 2-(4-(pyrazole-3-carbonylamino)phenethyl)-6-(3,4-dimethoxyphenyl)-2,3,4,5-tetrahydropyridazin-3-one 2-(4-(pyrazole-3-carbonylamino)phenethyl)-6-(3,4-dimethoxyphenyl)-5-ethyl-2,3,4,5-tetrahydropyridazin-3-one 3-(4-(pyrazole-3-carbonylamino)benzyl)-5-(3,4-dimethoxyphenyl)-3,6-dihydro-1,3,4-thiadiazin-2-one 3-(3-(pyrazole-3-carbonylamino)benzyl)-5-(3,4-dimethoxyphenyl)-3,6-dihydro-1,3,4-thiadiazin-2-one 3-(2-(pyrazole-3-carbonylamino)benzyl)-5-(3,4-dimethoxyphenyl)-3,6-dihydro-1,3,4-thiadiazin-2-one 3-(4-(pyrazole-3-carbonylamino)benzyl)-5-(3,4-dimethoxyphenyl)-6-ethyl-3,6-dihydro-1,3,4-thiadiazin-2-one 3-(3-(pyrazole-3-carbonylamino)benzyl)-5-(3,4-dimethoxyphenyl)-6-ethyl-3,6-dihydro-1,3,4-thiadiazin-2-one 3-(2-(pyrazole-3-carbonylamino)benzyl)-5-(3,4-dimethoxyphenyl)-6-ethyl-3,6-dihydro-1,3,4-thiadiazin-2-one 3-(4-(pyrazole-3-carbonylamino)benzyl)-5-(3-methoxy-4-trifluoromethoxyphenyl)-6-ethyl-3,6-dihydro-1,3,4-thiadiazin-2-one 3-(4-(pyrazole-3-carbonylamino)benzyl)-5-(3-methoxy-4-difluoromethoxyphenyl)-6-ethyl-3,6-dihydro-1,3,4-thiadiazin-2-one 3-(4-(pyrazole-3-carbonylamino)benzyl)-5-(3-methoxy-4-fluoromethoxyphenyl)-6-ethyl-3,6-dihydro-1,3,4-thiadiazin-2-one 3-(4-(pyrazole-3-carbonylamino)benzyl)-5-(3-difluoromethoxy-4-methoxyphenyl)-6-ethyl-3,6-dihydro-1,3,4-thiadiazin-2-one 3-(4-(pyrazole-3-carbonylamino)benzyl)-5-(3-trifluoromethoxy-4-methoxyphenyl)-6-ethyl-3,6-dihydro-1,3,4-thiadiazin-2-one 3-(4-(pyrazole-3-carbonylamino)benzyl)-5-(3-fluoromethoxy-4-methoxyphenyl)-6-ethyl-3,6-dihydro-1,3,4-thiadiazin-2-one 3-(4-(pyrazole-3-carbonylamino)benzyl)-5-(3-methoxy-4-ethoxyphenyl)-6-ethyl-3,6-dihydro-1,3,4-thiadiazin-2-one 3-(4-(pyrazole-3-carbonylamino)benzyl)-5-(3-ethoxy-4-methoxyphenyl)-6-ethyl-3,6-dihydro-1,3,4-thiadiazin-2-one 3-(4-(pyrazole-3-carbonylamino)benzyl)-5-(3-hydroxy-4-methoxyphenyl)-6-ethyl-3,6-dihydro-1,3,4-thiadiazin-2-one 3-(4-(pyrazole-3-carbonylamino)benzyl)-5-(4-methylsulfonylphenyl)-6-ethyl-3,6-dihydro-1,3,4-thiadiazin-2-one 3-(4-(pyrazole-3-carbonylamino)benzyl)-5-(4-methyleneoxyphenyl)-6-ethyl-3,6-dihydro-1,3,4-thiadiazin-2-one 3-(4-(pyrazole-3-carbonylamino)benzyl)-5-(3-cyclopentyloxy-4-methoxyphenyl)-6-ethyl-3,6-dihydro-1,3,4-thiadiazin-2-one 3-(3-(pyrazole-3-carbonylamino)benzyl)-5-(3-cyclopentyloxy-4-methoxyphenyl)-6-ethyl-3,6-dihydro-1,3,4-thiadiazin-2-one 3-(4-(pyrazole-3-carbonylamino)phenethyl)-5-(3,4-dimethoxyphenyl)-3,6-dihydro-1,3,4-thiadiazin-2-one 3-(4-(pyrazole-3-carbonylamino)phenethyl)-5-(3,4-dimethoxyphenyl)-6-ethyl-3,6-dihydro-1,3,4-thiadiazin-2-one 3-(4-(pyrazole-3-carbonylamino)benzyl)-5-(3,4-dimethoxyphenyl)-3,6-dihydro-1,3,4-oxadiazin-2-one 3-(3-(pyrazole-3-carbonylamino)benzyl)-5-(3,4-dimethoxyphenyl)-3,6-dihydro-1,3,4-oxadiazin-2-one 3-(2-(pyrazole-3-carbonylamino)benzyl)-5-(3,4-dimethoxyphenyl)-3,6-dihydro-1,3,4-oxadiazin-2-one 3-(4-(pyrazole-3-carbonylamino)benzyl)-5-(3,4-dimethoxyphenyl)-6-ethyl-3,6-dihydro-1,3,4-oxadiazin-2-one 3-(3-(pyrazole-3-carbonylamino)benzyl)-5-(3,4-dimethoxyphenyl)-6-ethyl-3,6-dihydro-1,3,4-oxadiazin-2-one 3-(2-(pyrazole-3-carbonylamino)benzyl)-5-(3,4-dimethoxyphenyl)-6-ethyl-3,6-dihydro-1,3,4-oxadiazin-2-one 3-(4-(pyrazole-3-carbonylamino)benzyl)-5-(3-methoxy-4-trifluoromethoxyphenyl)-6-ethyl-3,6-dihydro-1,3,4-oxadiazin-2-one 3-(4-(pyrazole-3-carbonylamino)benzyl)-5-(3-methoxy-4-difluoromethoxyphenyl)-6-ethyl-3,6-dihydro-1,3,4-oxadiazin-2-one 3-(4-(pyrazole-3-carbonylamino)benzyl)-5-(3-methoxy-4-fluoromethoxyphenyl)-6-ethyl-3,6-dihydro-1,3,4-oxadiazin-2-one 3-(4-(pyrazole-3-carbonylamino)benzyl)-5-(3-difluoromethoxy-4-methoxyphenyl)-6-ethyl-3,6-dihydro-1,3,4-oxadiazin-2-one 3-(4-(pyrazole-3-carbonylamino)benzyl)-5-(3-trifluoromethoxy-4-methoxyphenyl)-6-ethyl-3,6-dihydro-1,3,4-oxadiazin-2-one 3-(4-(pyrazole-3-carbonylamino)benzyl)-5-(3-fluoromethoxy-4-methoxyphenyl)-6-ethyl-3,6-dihydro-1,3,4-oxadiazin-2-one 3-(4-(pyrazole-3-carbonylamino)benzyl)-5-(3-methoxy-4-ethoxyphenyl)-6-ethyl-3,6-dihydro-1,3,4-oxadiazin-2-one 3-(4-pyrazole-3-carbonylamino)benzyl)-5-(3-ethoxy-4-methoxyphenyl)-6-ethyl-3,6-dihydro-1,3,4-oxadiazin-2-one 3-(4-pyrazole-3-carbonylamino)benzyl)-5-(3-hydroxy-4-methoxyphenyl)-6-ethyl-3,6-dihydro-1,3,4-oxadiazin-2-one 3-(4-pyrazole-3-carbonylamino)benzyl)-5-(4-methylsulfonylphenyl)-6-ethyl-3,6-dihydro-1,3,4-oxadiazin-2-one 3-(4-pyrazole-3-carbonylamino)benzyl)-5-(4-methyleneoxyphenyl)-6-ethyl-3,6-dihydro-1,3,4-oxadiazin-2-one 3-(4-pyrazole-3-carbonylamino)benzyl)-5-(3-cyclopentyloxy-4-methoxyphenyl)-6-ethyl-3,6-dihydro-1,3,4-oxadiazin-2-one 3-(3-pyrazole-3-carbonylamino)benzyl)-5-(3-cyclopentyloxy-4-methoxyphenyl)-6-ethyl-3,6-dihydro-1,3,4-oxadiazin-2-one 3-(4-pyrazole-3-carbonylamino)phenethy)-5-(3,4-dimethoxyphenyl)-3,6-dihydro-1,3,4-oxadiazin-2-one 3-(4-pyrazole-3-carbonylamino)phenethy)-5-(3,4-dimethoxyphenyl)-6-ethyl-3,6-dihydro-1,3,4-oxadiazin-2-one.

The following are obtained analogously by reaction of 2-(3-aminobenzyl)-6-(3-ethoxy-4-methoxyphenyl)-2,3,4,5-tetrahydropyridazin-3-one with nicotinoyl chloride
2-(3-nicotinoylaminobenzyl)-6-(3-ethoxy-4-methoxyphenyl)-2,3,4,5-tetrahydropyridazin-3-one, m.p. 204° of 2-(4-aminobenzyl)-6-(3-ethoxy-4-methoxyphenyl)-2,3,4,5-tetrahydropyridazin-3-one
with isonicotinoyl chloride
2-(4-isonicotinoylaminobenzyl)-6-(3-ethoxy-4-methoxyphenyl)-2,3,4,5-tetrahydropyridazin-3-one, hydrochloride, m.p. 252° with pyrazine-2-carbonyl chloride
2-(4-pyrazinecarbonylaminobenzyl)-6-(3-ethoxy-4-methoxyphenyl)-2,3,4,5-tetrahydropyridazin-3-one, m.p. 202° with isoxazole-5-carbonyl chloride
2-(4-(isoxazole-5-carbonylamino)benzyl)-6-(3-ethoxy-4-methoxyphenyl)-2,3,4,5-tetrahydropyridazin-3-one, m.p. 192° of 2-(4-aminobenzyl)-6-(3-cyclopentyloxy-4-methoxyphenyl)-2,3,4,5-tetrahydropyridazin-3-one with nicotinoyl chloride
2-(4-nicotinoylaminobenzyl)-6-(3-cyclopentyloxy-4-methoxyphenyl)-2,3,4,5-tetrahydropyridazin-3-one, m.p. 205° of 2-(4-aminobenzyl)-6-(3,4-dimethoxyphenyl)-2,3,4,5-tetrahydropyridazin-3-one with nicotinoyl chloride
2-(4-nicotinoylaminobenzyl)-6-(3,4-dimethoxyphenyl)-2,3,4,5-tetrahydropyridazin-3-one, hydrochloride, m.p. 212°.

The following examples relate to pharmaceutical preparations:

EXAMPLE A

Injection Vials

A solution of 100 g of an active compound of the formula I and 5 g of disodium hydrogen phosphate is adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The mixture is adjusted to pH 6.8, made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed in the customary manner to give tablets such that each tablet contains 10 mg of active compound.

EXAMPLE F

Coated Tablets

Analogously to Example E, tablets are pressed which are then coated in a customary manner with a coating of sucrose, potato starch, talc, tragacanth and colourant.

EXAMPLE G

Capsules 2 kg of active compound of the formula I are filled into hard gelatin capsules in a customary manner such that each capsule contains 20 mg of the active compound.

EXAMPLE H

Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

EXAMPLE I

Inhalation Spray 14 g of active compound of the formula I are dissolved in 10 l of isotonic NaCl solution and the solution is filled into commercially available spray containers having a pump mechanism. The solution can be sprayed into the mouth or nose. A burst or spray (approximately 0.1 ml) corresponds to a dose of approximately 0.14 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound of formula I

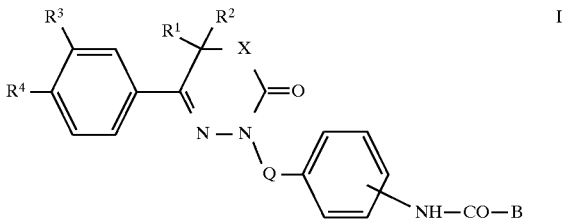

wherein

B is an aromatic heterocycle having 1 to 4 N, O and/or S atoms, bonded via N or C, which can be unsubstituted or mono-, di- or trisubstituted by Hal, A and/or OA, and can also be fused to a benzene or pyridine ring, Q is absent or is alkylene having 1–6 C atoms, X is $CH_2$, S or O, $R^1$ and $R^2$ in each case independently of one another are H or A, $R^3$ and $R^4$ in each case independently of *one another are —OH, $OR^5$, —S—$R^5$, —SO—$R^5$, —$SO_2$—$R^5$, Hal, methylenedioxy, —$NO_2$, —$NH_2$, —$NHR^5$ or —$NR^5R^6$, $R^5$ and $R^6$ in each case independently of one another are A, cycloalkyl having 3–7 C atoms, methylenecycloalkyl having 4–8 C atoms or alkenyl having 2–8 C atoms, A is alkyl having 1 to 10 C atoms, which can be substituted by 1 to 5 F and/or Cl atoms and Hal is F, Cl, Br or I or a physiologically acceptable salt thereof.

2. An enantiomer of a compound of the formula I according to claim 1.

3. A compound according to claim 1, wherein $R^1$ is H, $R^2$ is H or A, $R^3$ is OA and X is S.

4. A compound according to claim 1, wherein $R^1$ is H, $R^2$ is methyl or ethyl, $R^3$ and $R^4$ in each case independently of one another are OA and X is S.

5. A compound according to claim 1, wherein $R^1$ is H, $R^2$ is methyl or ethyl $R^3$ is OA $R^4$ is mono-, di- or trifl substituted alkyl having 1 atoms and X is S.

6. A compound according to claim 1, wherein $R^1$ is H, $R^2$ is methyl or ethyl, $R^3$ and $R^4$ in each case independently of one another are $OR^5$ and B is pyridyl.

7. A compound according to claim 1, wherein
R$^1$ and R$^2$ are H,
R$^3$ and R$^4$ in each case independently of one another are OA
B is pyridyl and
X is S or CH$_2$.

8. A compound according to claim 1, which is
(a) 3-(4-picolinoylaminobenzyl)-5-(3,4-dimethoxyphenyl)-6-ethyl-3,6-dihydro-1,3,4-thiadiazin-2-one;
(b) 3-(4-picolinoylaminobenzyl)-5-(3,4-dimethoxyphenyl-3,6-dihydro-1,3,4-thiadiazin-2-one;
(c) 3-(4-nicotinoylaminobenzyl)-5-(3,4-dimethoxyphenyl)-3,6-dihydro-1,3,4-thiadiazin-2-one;
(d) 3-(4-isonicotinoylaminobenzyl)-5-(3,4-dimethoxyphenyl)-3,6-dihydro-1,3,4-thiadiazin-2-one;
(e) 3-(4-nicotinoylaminobenzyl)-5-(3,4-dimethoxyphenyl)-6-ethyl-3,6-dihydro-1,3,4-oxadiazin-2-one; or
(f) 2-(4-nicotinoylaminobenzyl)-6-(3,4-dimethoxyphenyl)-5-ethyl-2,3,4,5-tetrahydropyridazin-3-one.

9. A pharmaceutical composition, comprising at least one compound of formula I according to claim 1 or a physiologically acceptable salt thereof and a pharmaceutically acceptable carrier.

10. A process for the preparation of a compound of formula I according to claim 1, or salt thereof, comprising
(a) reacting a compound of formula II

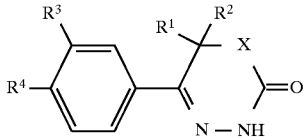

with a compound of the formula III

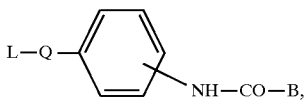

in which
L is Cl, Br, OH or a reactive esterified OH group;
(b) reacting a compound of the formula IV

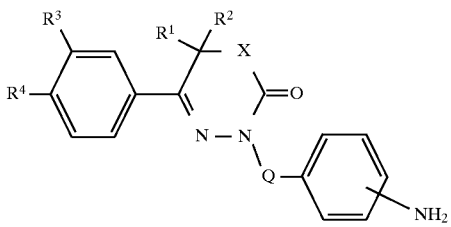

with a compound of the formula V

L-CO-B         V in which
L is Cl, Br, OH or a reactive esterified OH group,
or (c) converting a basic compound of the formula I into one of its salts by treating with an acid.

11. A process for the production of a pharmaceutical preparation, comprising bringing a compound of formula I according to claim 1 or one of its physiologically acceptable salts into a suitable dose form together with at least one solid, liquid or semiliquid excipient or auxiliary.

12. A method for the treatment of asthma, allergy, or inflammatory illnesses, comprising administering a compound of formula I according to claim 1, or a physiologically acceptable salt thereof.

13. A method of inhibiting phosphodiesterase IV, comprising administering a compound of formula I according to claim 1 or a physiologically acceptable salt thereof.

14. A method for the treatment of asthma, multiple sclerosis, rheumatoid arthritis, atopic dermatitis, or psoriasis, comprising administering a compound of formula I according to claim 1, or a physiologically acceptable salt thereof.

15. A method for the treatment of autoimmune disorders or transplant rejection, comprising administering a compound of formula I according to claim 1, or a physiologically acceptable salt thereof.

16. A method for the treatment of acquired immune deficiency syndrome, or transplant rejection reactions, comprising administering a compound of formula I according to claim 1, or a physiologically acceptable salt thereof.

17. A compound of formula I

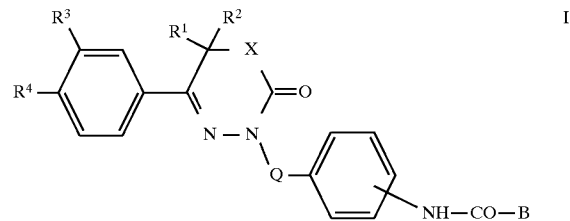

wherein
B is 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl,
Q is absent or is alkylene having 1–6 C atoms,
X is CH$_2$, S or O,
R$^1$ and R$^2$ in each case independently of one another are H or A,
R$^3$ and R$^4$ in each case independently of one another are —OH, OR$^5$, —S—R$^5$, —SO—R$^5$, —SO$_2$—R$^5$, Hal, methylenedioxy, —NO$_2$, —NH$_2$, —NHR$^5$ or —NR$^5$R$^6$,
R$^5$ and R$^6$ in each case independently of one another are A, cycloalkyl having 3–7 C atoms, methylenecycloalkyl having 4–8 C atoms or alkenyl having 2–8 C atoms,
A is alkyl having 1 to 10 C atoms, which can be substituted by 1 to 5 F and/or Cl atoms and Hal is F, Cl, Br or I
or a physiologically acceptable salt thereof.

18. A compound of formula I

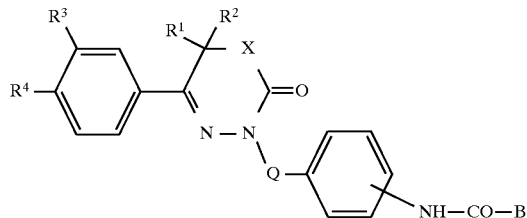 I wherein
B is nicotine or isonicotine,
Q is absent or is alkylene having 1–6 C atoms,
X is CH$_2$, S or O, R$^1$ and R$^2$ in each case independently of one another are H or A, R$^3$ and R$^4$ in each case independently of one another are —OH, OR$^5$, —S—R$^5$, —SO—R$^5$, —SO$_2$—R$^5$, Hal, methylenedioxy, —NO$_2$, —NH$_2$, —NHR$^5$ or —NR$^5$R$^6$, R$^5$ and R$^6$ in each case independently of one another are A, cycloalkyl having 3–7 C atoms, methylenecycloalkyl having 4–8 C atoms or alkenyl having 2–8 C atoms, A is alkyl having 1 to 10 C atoms, which can be substituted by 1 to 5 F and/or Cl atoms and Hal is F, Cl, Br or I
or a physiologically acceptable salt thereof.

* * * * *